US009688760B2

(12) United States Patent
Kufer et al.

(10) Patent No.: US 9,688,760 B2
(45) Date of Patent: *Jun. 27, 2017

(54) ANTI-LEUKOCYTE ADHESION FOR THE MITIGATION OF POTENTIAL ADVERSE EVENTS CAUSED BY CD3-SPECIFIC BINDING DOMAINS

(71) Applicant: AMGEN RESEARCH (MUNICH) GMBH, Munich (DE)

(72) Inventors: Peter Kufer, Munich (DE); Dirk Nagorsen, Munich (DE); Juergen Scheele, Munich (DE); Gerhard Zugmaier, Munich (DE); Matthias Klinger, Gilching (DE); Patrick Hoffmann, Bad Heilbrunn (DE); Virginie Naegele, Munich (DE); Elaine-Pashupati Dopfer, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 209 days.

This patent is subject to a terminal disclaimer.

(21) Appl. No.: 14/176,091

(22) Filed: Feb. 8, 2014

(65) Prior Publication Data

US 2014/0227272 A1 Aug. 14, 2014

Related U.S. Application Data

(60) Provisional application No. 61/811,526, filed on Apr. 12, 2013, provisional application No. 61/762,718, filed on Feb. 8, 2013.

(51) Int. Cl.
| | | |
|---|---|---|
| *C07H 21/04* | (2006.01) |
| *C07C 43/00* | (2006.01) |
| *C07C 49/00* | (2006.01) |
| *C07C 237/26* | (2006.01) |
| *C07C 331/00* | (2006.01) |
| *C12P 21/08* | (2006.01) |
| *A01N 37/18* | (2006.01) |
| *A61K 31/65* | (2006.01) |
| *A01N 31/00* | (2006.01) |
| *A61K 31/095* | (2006.01) |
| *G01N 33/00* | (2006.01) |
| *C12N 5/071* | (2010.01) |
| *C07K 16/28* | (2006.01) |
| *A61K 31/10* | (2006.01) |
| *A61K 39/395* | (2006.01) |
| *C07K 16/18* | (2006.01) |
| *G01N 33/50* | (2006.01) |
| *A61K 39/00* | (2006.01) |

(52) U.S. Cl.
CPC .......... *C07K 16/2809* (2013.01); *A61K 31/10* (2013.01); *A61K 31/65* (2013.01); *A61K 39/3955* (2013.01); *C07K 16/18* (2013.01); *G01N 33/5008* (2013.01); *C07K 2317/70* (2013.01); *G01N 2500/04* (2013.01)

(58) Field of Classification Search
CPC ............... C07K 16/18; C07K 16/2809; C07K 2317/17; G01N 33/5008; G01N 2500/04; A61K 31/10; A61K 31/65; A61K 39/3955
See application file for complete search history.

(56) References Cited

U.S. PATENT DOCUMENTS

| | | | |
|---|---|---|---|
| 2,689,848 A | 9/1954 | Husemann et al. | |
| 9,486,475 B2 * | 11/2016 | Kufer | A61K 31/737 |
| 2009/0047243 A1 * | 2/2009 | Rickles et al. | 424/85.2 |
| 2009/0053168 A1 * | 2/2009 | Rickles et al. | 424/85.2 |
| 2010/0105889 A1 | 4/2010 | Deshpande et al. | |
| 2014/0099254 A1 * | 4/2014 | Chang et al. | 424/1.11 |
| 2014/0227272 A1 * | 8/2014 | Kufer et al. | 424/135.1 |
| 2014/0228316 A1 * | 8/2014 | Kufer | A61K 31/737 |
| | | | 514/54 |

FOREIGN PATENT DOCUMENTS

| | | |
|---|---|---|
| EP | 623679 A1 | 11/1994 |
| WO | WO9954440 A1 | 10/1999 |

(Continued)

OTHER PUBLICATIONS (R) Merck Index, 14th. Ed., 2006, Merck & Co., Whitehouse Station, New Jersey, see p. 1231, Entry No. 7134 ; see "Pentosan Polysulfate" and the sodium salt thereof.*
Baaten et al., Regulation of Antigen-Experienced T Cells: Lessons from the Quintessential Memory Marker CD44. *Front Immunol.* 3: 23 (2012).

(Continued)

*Primary Examiner* — Lawrence E Crane
(74) *Attorney, Agent, or Firm* — Marshall, Gerstein & Borun LLP

(57) ABSTRACT

The present invention relates in essence to use of a compound, which decreases or inhibits the binding of mammalian T-cells to mammalian endothelial cells for use in a method of prophylaxis and/or amelioration and/or treatment of clinical adverse events caused by a therapy which comprises re-directing of T-cells against target cells in a patient. Such a therapy includes, but is not limited to, treatment with an antibody comprising a CD3 binding domain, such as a CD20×CD3 or a CD19×CD3 bispecific single chain antibody, e.g., blinatumomab (MT-103). Methods of treatment of patients having or being at risk of clinical adverse events caused by therapy which comprises re-directing of T-cells against target cells are also contemplated, as are methods of identifying a compound for administration in the methods of prophylaxis, amelioration and/or treatment. Such anti-adhesive type compounds include, but are not limited to, antibodies, like natalizumab, efalizumab, and etrolizumab; minocycline, (acetyl-)salicyclic acid, astilbin, and flavonoids; and thrombin and pentosanpolysulfate (PPS), or a pharmaceutically acceptable salt thereof.

10 Claims, 20 Drawing Sheets

(56) References Cited

FOREIGN PATENT DOCUMENTS

| WO | WO-2004/106381 A1 | 12/2004 |
|---|---|---|
| WO | WO-2007/068354 A1 | 6/2007 |
| WO | WO-2007/131092 A2 | 11/2007 |
| WO | WO-2007/147090 A2 | 12/2007 |
| WO | WO-2008/119565 A2 | 10/2008 |
| WO | WO-2008/119566 A2 | 10/2008 |
| WO | WO-2008/119567 A2 | 10/2008 |
| WO | WO-2011/051307 A1 | 5/2011 |
| WO | WO-2012/146394 A1 | 11/2012 |

OTHER PUBLICATIONS

Bargou et al., Tumor regression in cancer patients by very low doses of a T cell-engaging antibody. *Science* 321: 974-7 (2008).

Bucolo et al., New coumarin-based anti-inflammatory drug: Putative antagonist of the integrins alphaLbeta2 and alphaMbeta2. *J. Pharm. Pharmacol.* 60(11): 1473-9 (2008).

Crick, Codon—anticodon pairing: The wobble hypothesis. *J. Mol. Biol.* 19: 548-55 (1966).

Curley et al., Integrin antagonists. *Cell. Mol. Life Sci.* 56: 427-41 (1999).

Ding et al., Regulation of chemokine-induced transendothelial migration of T lymphocytes by endothelial activation: differential effects on naive and memory T cells. *J. Leukoc. Biol.* 67(6): 825-33 (2000).

Eylar et al., Sustained levels of ascorbic acid are toxic and immunosuppressive for human T cells. *P R Health Sci. J.* 15: 21-6 (1996).

Fabene et al., A role for leukocyte-endothelial adhesion mechanisms in epilepsy. *Nat. Med.* 14: 1377-83 (2008).

Fagan et al., Minocycline to improve neurologic outcome in stroke (MINOS): A dose-finding study. *Stroke* 41: 2283-7 (2010).

Feigelson et al., The Src kinase p56(lck) up-regulates VLA-4 integrin affinity. Implications for rapid spontaneous and chemokine-triggered T cell adhesion to VCAM-1 and fibronectin. *J. Biol. Chem.* 276: 13891-901 (2001).

Feng et al., Endogenous PMN sialidase activity exposes activation epitope on CD11b/CD18 which enhances its binding interaction with ICAM-1. *J. Leukoc. Biol.* 90: 313-21 (2011).

Fiedler et al., Angiopoietins: A link between angiogenesis and inflammation. *Trends Immunol.* 27: 552-8 (2006).

GenBank Accession No. AAA69966, CD19 [*Homo sapiens*], dated Jul. 18, 1995.

GenBank Accession No. NM_000733, Homo sapiens CD3e molecule, epsilon (CD3-TCR complex) (CD3E), mRNA, dated Mar. 24, 1999.

Gerli et al., Salicylates inhibit T cell adhesion on endothelium under nonstatic conditions: Induction of L-selectin shedding by a tyrosine kinase-dependent mechanism. *J. Immunol.* 166(2): 832-40 (2001).

Grupp et al., Chimeric antigen receptor-modified T cells for acute lymphoid leukemia. *N. Engl. J. Med.* 368(16): 1509-18 (2013).

Haanstra et al., Antagonizing the α4β1 integrin, but not α4β7, inhibits leukocytic infiltration of the central nervous system in rhesus monkey experimental autoimmune encephalomyelitis. *J. Immunol.* 190(5): 1961-73 (2013).

Hirota-Takahata et al., F-19848 A, a novel inhibitor of hyaluronic acid binding to cellular receptor CD44. *J. Antibiot.*(Tokyo), 60: 633-9 (2007).

Höpfner et al., Selectin-blocking semisynthetic sulfated polysaccharides as promising anti-inflammatory agents. *J. Pharm. Pharmacol.* 55: 697-706 (2003).

Hosse et al., A new generation of protein display scaffolds for molecular recognition. *Protein Sci.* 15:14-27 (2006).

Kabat et al., Sequences of Proteins of Immunological Interest, 5th Ed. U.S. Department of Health and Human Services, Public Health Services National Institutes of Health (1991).

Kivisäkk et al., Human cerebrospinal fluid central memory CD4+ T cells: Evidence for trafficking through choroid plexus and meninges via P-selectin. *Proc. Natl. Acad. Sci. USA*, 100: 8389-94 (2003).

Kling et al., Pharmacological control of platelet-leukocyte interactions by the human anti-P-selectin antibody inclacumab—preclinical and clinical studies. *Thromb. Res.* 131(5): 401-10 (2013).

Kochenderfer et al., Treating B-cell cancer with T cells expressing anti-CD19 chimeric antigen receptors. *Nat. Rev. Clin. Oncol.* 10(5): 267-76 (2013).

Koszik et al., Efalizumab modulates T cell function both in vivo and in vitro. *J. Dermatol. Sci.* 60: 159-66 (2010).

Ku et al., Concentration dependent anti-inflammatory effects thrombin on polyphosphate-mediated inflammatory responses in vitro and in vivo. *Inflamm. Res.* 62(6): 609-16 (2013).

Lampl et al., Minocycline treatment in acute stroke: An open-label, evaluator-blinded study. *Neurology* 69: 1404-10 (2007).

Lefer, Pharmacology of selectin inhibitors in ischemia/reperfusion states. *Ann. Rev. Pharmacol. Toxicol.* 40: 283-94 (2010).

Mobley et al., Measurement of cellular adhesion under static conditions. *Curr. Protoc. Immunol.* Chapter 7: Unit 7.28 (2001).

Moore, Structure and function of P-selectin glycoprotein ligand-1. *Leuk. Lymphoma*, 29: 1-15 (1998).

Murai et al., CD44-chondroitin sulfate interactions mediate leukocyte rolling under physiological flow conditions. *Immunol. Lett.* 93: 163-70 (2004).

Needleman et al., A general method applicable to the search for similarities in the amino acid sequence of two proteins. *J. Mol. Biol.* 48: 443-53 (1970).

Nicaise et al., Affinity transfer by CDR grafting on a nonimmunoglobulin scaffold. *Protein Sci.* 13: 1882-91 (2004).

Nikodemova et al., Minocycline attenuates experimental autoimmune encephalomyelitis in rats by reducing T cell infiltration into the spinal cord. *J. Neuroimmunol.* 219: 33-7 (2010).

Nygren et al., Scaffolds for engineering novel binding sites in proteins. *Curr. Opin. Struct. Biol.* 7: 463-9 (1997).

Offner et al., Induction of regular cytolytic T cell synapses by bispecific single-chain antibody constructs on MHC class I-negative tumor cells. *Mol. Immunol.* 43: 763-71 (2006).

Osaka et al., In vivo imaging of leukocyte recruitment to the atheroprone femoral artery reveals anti-inflammatory effects of rosuvastatin. *Biomed. Res. Int.* 2013: 962369 (2013).

Porter et al., Chimeric antigen receptor-modified T cells in chronic lymphoid leukemia. *N. Engl. J. Med.* 365: 725-33 (2011).

Pullen et al., Pharmacological characterization of PF-00547659, an anti-human MAdCAM monoclonal antibody. *Br. J. Pharmacol.* 157: 281-93 (2009).

Rao et al., Delivery of SAR 1118 to the retina via ophthalmic drops and its effectiveness in a rat streptozotocin (STZ) model of diabetic retinopathy (DR). *Invest. Ophthalmol. Vis. Sci.* 51: 5198-204 (2010).

Rohnelt et al., Immunosurveillance modelled in vitro: naive and memory T cells spontaneously migrate across unstimulated microvascular endothelium. *Int. Immunol.* 9(3): 435-50 (1997).

Skerra, Alternative non-antibody scaffolds for molecular recognition. *Curr. Opin. Biotechnol.* 18: 295-304 (2007).

Smith et al., Comparison of biosequences. *Adv. Appl. Math.* 2: 482-9 (1981).

Stefanich et al., A humanized monoclonal antibody targeting the β7 integrin selectively blocks intestinal homing of T lymphocytes. *Br. J. Pharmacol.* 162: 1855-70 (2011).

Thomas et al., Targeting leukocyte migration and adhesion in Crohn's disease and ulcerative colitis. *Inflammopharmacology* 20: 1-18 (2012).

Topp et al., Targeted therapy with the T-cell-engaging antibody blinatumomab of chemotherapy-refractory minimal residual disease in B-lineage acute lymphoblastic leukemia patients results in high response rate and prolonged leukemia-free survival. *J. Clin. Oncol.* 29: 2493-8 (2011).

Valignat et al., T lymphocytes orient against the direction of fluid flow during LFA-1-mediated migration. *Biophys. J.* 104(2): 322-31 (2013).

Van Deventer et al., A phase II dose ranging, double-blind, placebo-controlled study of alicaforsen enema in subjects with acute exacerbation of mild to moderate left-sided ulcerative colitis. *Aliment. Pharmacol. Ther.* 23: 1415-25 (2006).

(56) References Cited

OTHER PUBLICATIONS

Weeks et al., Natramune and PureWay-C reduce xenobiotic-induced human T-cell alpha5beta1 integrin-mediated adhesion to fibronectin. *Med. Sci. Monit.* 14: BR279-85 (2008).
Welzenbach et al., Small molecule inhibitors induce conformational changes in the I domain and the I-like domain of lymphocyte function-associated antigen-1. Molecular insights into integrin inhibition. *J. Biol. Chem.* 277: 10590-8 (2002).
Yi et al., Astilbin inhibits the adhesion of T lymphocytes via decreasing TNF-alpha and its associated MMP-9 activity and CD44 expression. *Int. Immunopharmacol.* 8: 1467-74 (2008).
Zhang et al., Pilot study of minocycline in relapsing-remitting multiple sclerosis. *Can. J. Neurol. Sci.* 35: 185-91 (2008).
Kadmiel et al., Glucocorticoid receptor signaling in health and disease. *Trends Pharmacol. Sci.* 34(9): 518-30 (2013).
Lee et al., Current concepts in the diagnosis and management of cytokine release syndrome. *Blood* 124(2): 188-95 (2014).

* cited by examiner

Patients without PPS co-medication:

A. Patient 109-026

B. Patient 153-001 without PPS co-medication

C. Patient 109-033 without PPS co-medication

Patients with PPS co-medication

D. Patient 109-042

E. Patient 109-036

F. Patient 109-040

SEQUENCE LISTING

```
<160> NUMBER OF SEQ ID NOS: 22

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160
```

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
        180                 185                 190

Lys Ala Thr Leu Thr Ala Asp Glu Ser Ser Ser Thr Ala Tyr Met Gln
    195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
            420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc      60
atctcctgca aggccagcca aagtgttgat tatgatggtg atagttattt gaactggtac     120

```
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg gagggaccaa gctcgagatc aaaggtggtg gtggttctgg cggcggcggc    360
tccggtggtg gtggttctca ggtgcagctg cagcagtctg ggctgagct ggtgaggcct     420 gggtcctcag tgaagatttc ctgcaaggct tctggctatg cattcagtag ctactggatg    480
aactgggtga agcagaggcc tggacagggt cttgagtgga ttggacagat ttggcctgga    540
gatggtgata ctaactacaa tggaaagttc aagggtaaag ccactctgac tgcagacgaa    600
tcctccagca cagcctacat gcaactcagc agcctagcat ctgaggactc tgcggtctat    660
ttctgtgcaa gacgggagac tacgacggta ggccgttatt actatgctat ggactactgg    720
ggccaaggga ccacggtcac cgtctcctcc ggaggtggtg gatccgatat caaactgcag    780
cagtcagggg ctgaactggc aagacctggg gcctcagtga agatgtcctg caagacttct    840
ggctacacct ttactaggta cacgatgcac tgggtaaaac agaggcctgg acagggtctg    900
gaatggattg gatacattaa tcctagccgt ggttatacta attacaatca gaagttcaag    960
gacaaggcca cattgactac agacaaatcc tccagcacag cctacatgca actgagcagc   1020
ctgacatctg aggactctgc agtctattac tgtgcaagat attatgatga tcattactgc   1080
cttgactact ggggccaagg caccactctc acagtctcct cagtcgaagg tggaagtgga   1140
ggttctggtg aagtggagg ttcaggtgga gtcgacgaca ttcagctgac ccagtctcca    1200
gcaatcatgt ctgcatctcc aggggagaag gtcaccatga cctgcagagc cagttcaagt   1260
gtaagttaca tgaactggta ccagcagaag tcaggcacct cccccaaaag atggatttat   1320
gacacatcca agtggcttc tggagtccct tatcgcttca gtggcagtgg gtctgggacc    1380
tcatactctc tcacaatcag cagcatggag gctgaagatg ctgccactta ttactgccaa   1440
cagtggagta gtaacccgct cacgttcggt gctgggacca agctggagct gaaa         1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4

```
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtgaa tactaactac     180
aatggaaagt tcaagggtaa agccactctg actgcagacg aatcctccag cacagcctac     240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372
```

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110
```

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                   333
```

```
<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8
gatatcaaac tgcagcagtc aggggctgaa ctggcaagac ctggggcctc agtgaagatg      60
tcctgcaaga cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca aatcctccag cacagcctac     240
atgcaactga gcagcctgac atctgaggac tctgcagtct attactgtgc aagatattat     300
gatgatcatt actgccttga ctactggggc caaggcacca ctctcacagt ctcctca       357

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80
```

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys
        100                 105

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10
gacattcagc tgacccagtc tccagcaatc atgtctgcat ctccagggga gaaggtcacc        60
atgacctgca gagccagttc aagtgtaagt tacatgaact ggtaccagca gaagtcaggc       120
acctccccca aaagatggat ttatgacaca tccaaagtgg cttctggagt cccttatcgc       180
ttcagtggca gtgggtctgg gacctcatac tctctcacaa tcagcagcat ggaggctgaa       240
gatgctgcca cttattactg ccaacagtgg agtagtaacc cgctcacgtt cggtgctggg       300
accaagctgg agctgaaa                                                     318

<210> SEQ ID NO 11
<211> LENGTH: 10
<212> TYPE: PRT
<213> ORGANISM: artificial
<220> FEATURE:
<223> OTHER INFORMATION: CD3 CDR-H1

<400> SEQUENCE: 11

Gly Tyr Thr Phe Thr Arg Tyr Thr Met His
1               5                   10

<210> SEQ ID NO 12
<211> LENGTH: 17
<212> TYPE: PRT
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

```
<400> SEQUENCE: 14

Arg Ala Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1

<400> SEQUENCE: 17

Gly Tyr Ala Phe Ser Ser Tyr Trp Met Asn
1               5                   10

<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1
```

```
<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5
```

ANTI-LEUKOCYTE ADHESION FOR THE MITIGATION OF POTENTIAL ADVERSE EVENTS CAUSED BY CD3-SPECIFIC BINDING DOMAINS

CROSS REFERENCE TO RELATED APPLICATIONS

This application claims the priority benefit of Provisional U.S. Patent Application No. 61/762,718, filed Feb. 8, 2013 and Provisional U.S. Patent Application No. 61/811,526, filed Apr. 12, 2013.

The entire contents of the ASCII text entitled "48363_seq_Listing.txt," created on Feb. 8, 2014, and having a size of 16 kilobytes is incorporated herein by reference.

FIELD OF THE INVENTION

The present invention relates in essence to a compound which decreases or inhibits the binding of mammalian T-cells to mammalian endothelial cells for use in a method of prophylaxis and/or amelioration and/or treatment of clinical adverse events caused by therapy which comprises re-directing of T-cells against target cells in a patient. Methods of treatment of patients having or being at risk of clinical adverse events caused by therapy which comprises re-directing of T-cells against target cells are also contemplated. Moreover, this invention relates to kits which comprise any of these compounds or a combination thereof, a CD3-specific binding domain or a nucleic acid which encodes a chimeric antigen receptor (CAR), and an enclosed label or package insert indicating that the compound or the combination is to be employed for the prophylaxis or amelioration of clinical adverse events caused by a therapy which comprises re-directing of T cells against target cells.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

BACKGROUND OF THE INVENTION

In 2012, B cell-malignancies constituted approximately 5% of newly diagnosed cancers in the US. Age-adjusted incidence rates for acute lymphocytic leukemia (ALL), chronic lymphocytic leukemia (CLL), and B-cell non-Hodgkin lymphoma (B-NHL) were 1.6, 4.2, and 16.5 per 100,000 men and women per year, respectively (Howlader N, Noone A M, Krapcho M, Neyman N, Aminou R, Altekruse S F, Kosary C L, Ruhl J, Tatalovich Z, Cho H, Mariotto A, Eisner M P, Lewis D R, Chen H S, Feuer E J, Cronin K A (eds). *SEER Cancer Statistics Review*, 1975-2009 (*Vintage* 2009 *Populations*), National Cancer Institute. Bethesda, Md., http://seer.cancer.gov/csr/1975_2009_pops09/, based on November 2011 SEER data submission, posted to the SEER web site, 2012). Despite repeated intensive standard treatments B cell-malignancies may become refractory to or relapse after therapy and frequently remain incurable. Therefore, a high medical need exists for innovative treatment modalities to improve the outcome in these patient populations.

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. This situation provides the basis for a therapeutic window in which a defined amount of the antibody-based therapeutic effectively hits cancer cells but spares normal cells.

Monoclonal antibodies were first added to standard chemotherapy about 20 years ago, yet this combination has not proved to be completely curative in B cell-malignancies. In recent years, a novel therapeutic approach with bispecific single-chain antibodies has entered clinical studies and shown promising initial results. Multispecific antibodies, such as bispecific antibodies, which re-direct T-cells, are of special interest for the treatment of cancer target cells. Re-directing of T cells comprises that T cells are equipped with an antigen receptor specificity which differs from the T cells' clonotypic natural antigen receptor specificity, i.e. the re-directed T-cells comprise for example a binding domain recognizing said cancer target cells. This can e.g. be achieved by T cell engaging bi- or multi-functional antibodies or antibody derivatives, such as bispecific antibodies comprising inter alia a CD3-specific binding domain, or by transduction of T cells with chimeric antigen receptors (CARs) such as CARs recognizing CD19 (see Knochenderfer et al., Nature Reviews 2013; Clinical Oncology; "Treating B-cell cancer with T cells expressing anti-CD19 chimeric antigen receptors"). Bispecific antibodies targeting CD19 or CD20 on B cells and CD3 on T cells are of special interest for the treatment of B cell-malignancies. Blinatumomab (sometimes also denoted as AMG 103 or MT103) is a recombinant CD19×CD3 bispecific scFv antibody consisting of four immunoglobulin variable domains assembled into a single polypeptide chain. Two of the variable domains form the binding site for CD19 which is a cell surface antigen expressed on most normal and malignant B cells. The other two variable domains form the binding site for CD3 which is part of the T cell-receptor complex on T cells. By binding to CD19 on a normal or malignant B cell and concomitantly engaging a T cell via CD3, Blinatumomab induces the formation of a cytolytic synapse (Offner et al. *Mol. Immunol.* 2006; 43:763-71), thereby leading to the eradication of the bound B cell. Blinatumomab is designed to polyclonally redirect the body's cytotoxic T cells against multiple B tumor cells.

Various clinical studies evaluating the safety and efficacy of Blinatumomab have been conducted both in B-NHL (Bargou et al. *Science*. 2008; 321:974-7) and B-precursor ALL (Topp et al. *J Clin Oncol*. 2011; 29:2493-8). These studies established clinical proof of concept for the high therapeutic potential of the bispecific single-chain antibody format in general and of Blinatumomab in special and validated its further development in B-NHL, ALL and CLL.

Though antibodies are an effective means in treating many disorders, in particular cancer, their administration is not necessarily devoid of side effects. A "side effect" which is sometimes also denoted as "adverse effect" or more frequently as "adverse event" (sometimes also denoted as "AE") in clinical studies, is a harmful and undesired effect resulting from medication in the treatment of a patient with a re-directed T-cell for example by way of a multispecific antibody or more preferably a bispecific antibody comprising a CD3-specific binding domain. Adverse effects may cause a reversible or irreversible change in the health status of a patient. As adverse effects could be harmful and potentially even life-threatening it is highly desirable to avoid them.

However, it is difficult to design a therapy which comprises re-directing of T-cells against target cells in a patient (for example a CD19×CD3 bispecific single-chain antibody-based therapy) which does not cause neurological symptoms, or to put it differently, it is desired to provide such a therapy, for example a CD19×CD3 bispecific single-chain antibody-based therapy with increased patient tolerability, i.e. reduced or even no harmful side effects such as CNS AEs. It is particularly desired to mitigate CNS AEs to an extent avoiding discontinuation of treatment due to CNS AEs thus allowing the patients to fully benefit from the treatment.

There is thus a strong need in the art to provide means and methods which attenuate or even avoid the above mentioned side effects that typically accompany a therapy that is based on re-directed T-cells (such as a therapy that makes use of a CD19×CD3 bispecific single-chain antibody).

The present invention addresses this need and thus provides, as a solution to the technical problem, a compound which decreases or inhibits the binding of mammalian T-cells to mammalian endothelial cells for use in a method of prophylaxis and/or amelioration and/or treatment of clinical adverse events caused by therapy which comprises re-directing of T-cells against target cells in a patient.

Further embodiments of the present invention are characterized and described herein and also reflected in the claims.

SUMMARY OF THE INVENTION

The present invention provides a compound which decreases or inhibits the binding of mammalian T-cells to mammalian endothelial cells for use in a method of prophylaxis and/or amelioration and/or treatment of clinical adverse events caused by therapy which comprises re-directing of T-cells against target cells in a patient.
In one embodiment, said compound is a compound which
  (a) is capable of binding to a T-cell adhesion molecule,
  (b) is capable of blocking the binding site of a T-cell adhesion molecule, and/or
  (c) inhibits or reduces the expression of a T-cell adhesion molecule,
and which decreases or inhibits the binding of mammalian T-cells to mammalian endothelial cells, for use in a method of prophylaxis and/or amelioration and/or treatment of clinical adverse events caused by therapy which comprises re-directing of T-cells against target cells in a patient.
In a further embodiment, said compound is a compound which
  (a) is capable of binding to an endothelial adhesion molecule,
  (b) is capable of blocking the binding site of an endothelial adhesion molecule, and/or
  (c) inhibits or reduces the expression of an endothelial adhesion molecule,
and which decreases or inhibits the binding of mammalian T-cells to mammalian endothelial cells, for use in a method of prophylaxis and/or amelioration and/or treatment of clinical adverse events caused by therapy which comprises re-directing of T-cells against target cells in a patient.

The present invention also provides a method of identifying a compound for use in a method of prophylaxis and/or amelioration and/or treatment of clinical adverse events caused by therapy which comprises re-directing of T-cells against target cells in a patient, comprising:
  (a) contacting said compound with a mammalian T-cell, a mammalian endothelial cell, a T-cell adhesion molecule and/or an endothelial adhesion molecule; and
  (b) evaluating whether said compound:
    (i) decreases or inhibits the binding of mammalian T-cells to mammalian endothelial cells;
    (ii) is capable of binding to a T-cell adhesion molecule,
    (iii) is capable of blocking the binding site of a T-cell adhesion molecule,
    (iv) inhibits or reduces the expression of a T-cell adhesion molecule,
    (v) is capable of binding to an endothelial adhesion molecule,
    (vi) is capable of blocking the binding site of an endothelial adhesion molecule, and/or
    (vii) inhibits or reduces the expression of an endothelial adhesion molecule.

It is envisaged in one embodiment that said therapy which comprises re-directing of T-cells against target cells in a patient, includes a CD3 binding domain.

In another embodiment it is envisaged that said therapy which comprises re-directing of T-cells against target cells in a patient, includes a genetically engineered T-cell having a chimeric antigen receptor (CAR).

It is also envisaged that the compound which is to be used in accordance with the present invention, is to be administered prior to and/or concomitantly with an initial dosing, a re-exposure (i.e. a re-dosing, such as for example a subsequent dosage step) and/or an increase of the dosage of said therapy (which is common practice when administering for example an antibody) which comprises re-directing of T-cells against target cells in a patient.

The present invention further provides a kit comprising a compound as defined or identified in accordance with the present invention, together with a CD3 binding domain.

The present invention also provides a kit comprising a compound as defined or identified in accordance with the present invention, together with a nucleic acid which encodes a chimeric antigen receptor (CAR).

A pharmaceutical composition comprising a compound as defined or identified in accordance with the present invention together with a CD3 binding domain.

The present invention further relates to a CD3 binding domain for use in a method of re-directing of T-cells against target cells in a patient, wherein said patient is subject to therapy comprising the compound as defined herein.

In one embodiment, the present invention relates to a nucleic acid which encodes a chimeric antigen receptor (CAR) for use in a method of re-directing of T-cells against target cells in a patient, wherein said patient is subject to therapy comprising the compound as defined herein.

In one embodiment said clinical adverse events comprise neurological adverse events.

In a further embodiment, said neurological adverse event is/are one or more of (i) cognitive disorder comprising disorientation/confusion and/or word finding problems/aphasia, (ii) seizure, (iii) cerebellar symptoms partly observed as an optional prodromal phase of (i) or (ii) comprising kinetic tremor, ataxia, dysarthria and handwriting problems.

In the context of the present invention, it is particularly envisaged that said CD3 binding domain is a bispecific single chain antibody.

Said bispecific single chain antibody comprises in a further embodiment of the present invention a binding domain which is specific for B-cells, preferably specific for a CD-marker that can be found on B-cell lymphoma such as CD19, CD22, CD20 or CD79a, CD19 being preferred.

In one embodiment, said bispecific single chain antibody is a CD19×CD3 or CD20×CD3 bispecific single chain antibody.

In further embodiments of the present invention, said chimeric antigen receptor (CAR) comprises a binding domain which is specific for B-cells, preferably specific for a CD-marker that can be found on B-cell lymphoma such as CD19, CD22, CD20 or CD79a, CD19 being preferred.

In a particularly preferred embodiment of the present invention, said CD19×CD3 bispecific single chain antibody is Blinatumomab (sometimes also denoted as MT103 or AMG103).

In a further preferred embodiment of the present invention, said patient is characterized by a B/T-cell ratio of less than 1:5 or a B-cell number of less than about 50 B-cells per µl peripheral blood.

It is envisaged that the compound that is to be used in the context of the present invention is selected from the compounds disclosed herein.

The present invention also relates to a method for prophylaxis, amelioration and/or treatment of clinical adverse events caused by therapy which comprises re-directing of T-cells against target cells in a patient, said method comprising administering a therapeutically effective amount of a compound defined herein.

In one embodiment of the present invention, said mammalian T-cells, whose binding to mammalian endothelial cells is decreased or inhibited by the compound defined herein, are re-directed mammalian T-cells.

It is also contemplated that the mammalian endothelial cells mentioned in the context of the present invention as described herein, are isolated from large blood vessels or capillaries.

In one embodiment, said mammalian endothelial cells are selected from Human Umbilical Vein Endothelial Cells (HUVEC) or Human Brain Microvascular Endothelial Cells (HBMEC), HBMECs being preferred.

The T-cell adhesion molecule is, in the context of the present invention, selected from integrins (such as alpha4-integrins; alphaL-beta2-integrins, alphaL-integrins, beta7-integrins), selectins (such as L-selectin), and/or CD44.

The endothelial adhesion molecule is, in the context of the present invention, selected from selectins (such as E- or P-selectin); cell adhesion molecules CAMs (such as ICAM-1, MAdCAM, VCAM-1) and/or PAR-1.

It is also envisaged that in the context of the present invention, said patient is a mammal, preferably a primate, and most preferably a human being.

Cell counts/percentage and protein concentration in peripheral blood and serum are shown, respectively. A. T cell-redistribution characterized by a rapid T cell-disappearance from peripheral blood immediately (i.e. already at 45 minutes) after start of infusion. B. Increased T cell-numbers with intermediate-affinity (i.e. activated) LFA-1 on its cell surface peaking concurrently with T cell-redistribution. C. Increased serum concentrations of Ang-2 released by activated endothelial cells during T cell-redistribution. D. T cell-redistribution is accompanied by disappearance of other mononuclear cells (as shown for e.g. monocytes) from peripheral blood with prolonged recovery to baseline counts.

Figure 2:
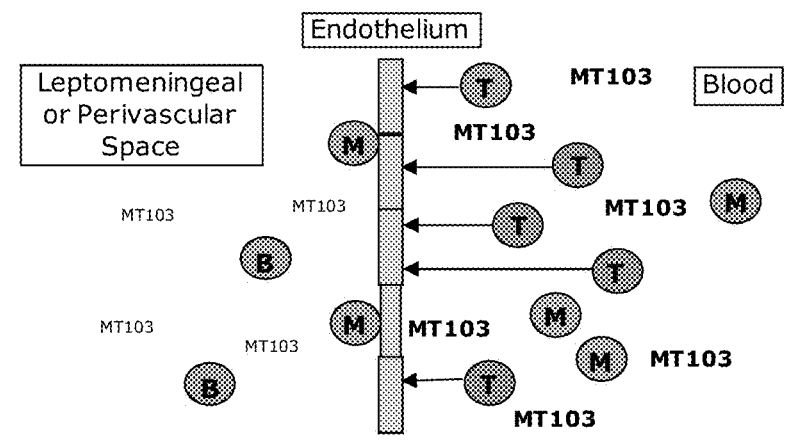
Figure 2:
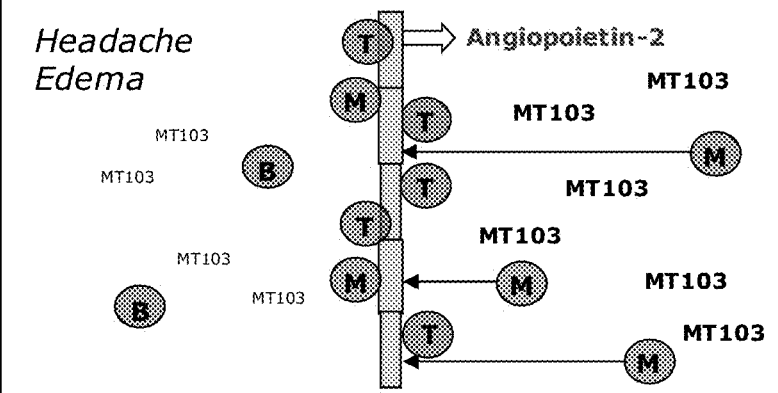

FIG. 2. Current hypothesis of the multi-step pathomechanism leading to central nervous system adverse events caused by Blinatumomab.

A. Start of infusion or stepwise dose increase of Blinatumomab increase T cell-adhesion to blood vessel endothelium. B. Adherent T cells activate the endothelium and start to extravasate. Activated endothelial cells attract other peripheral blood leukocytes, e.g. monocytes. Extravasated T cells secrete cytokines and chemokines which in turn cause transient neuroinflammation and pertubation of the blood-CSF-barrier.

Figure 3:
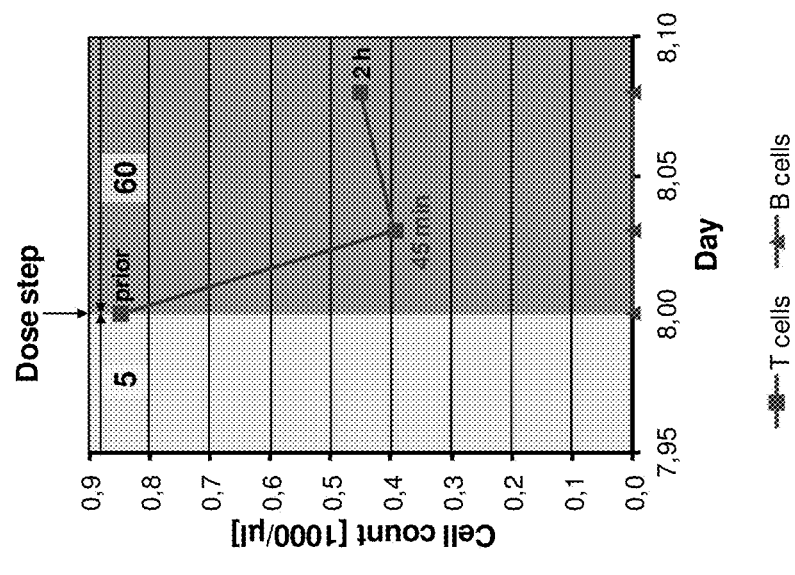
Figure 3:
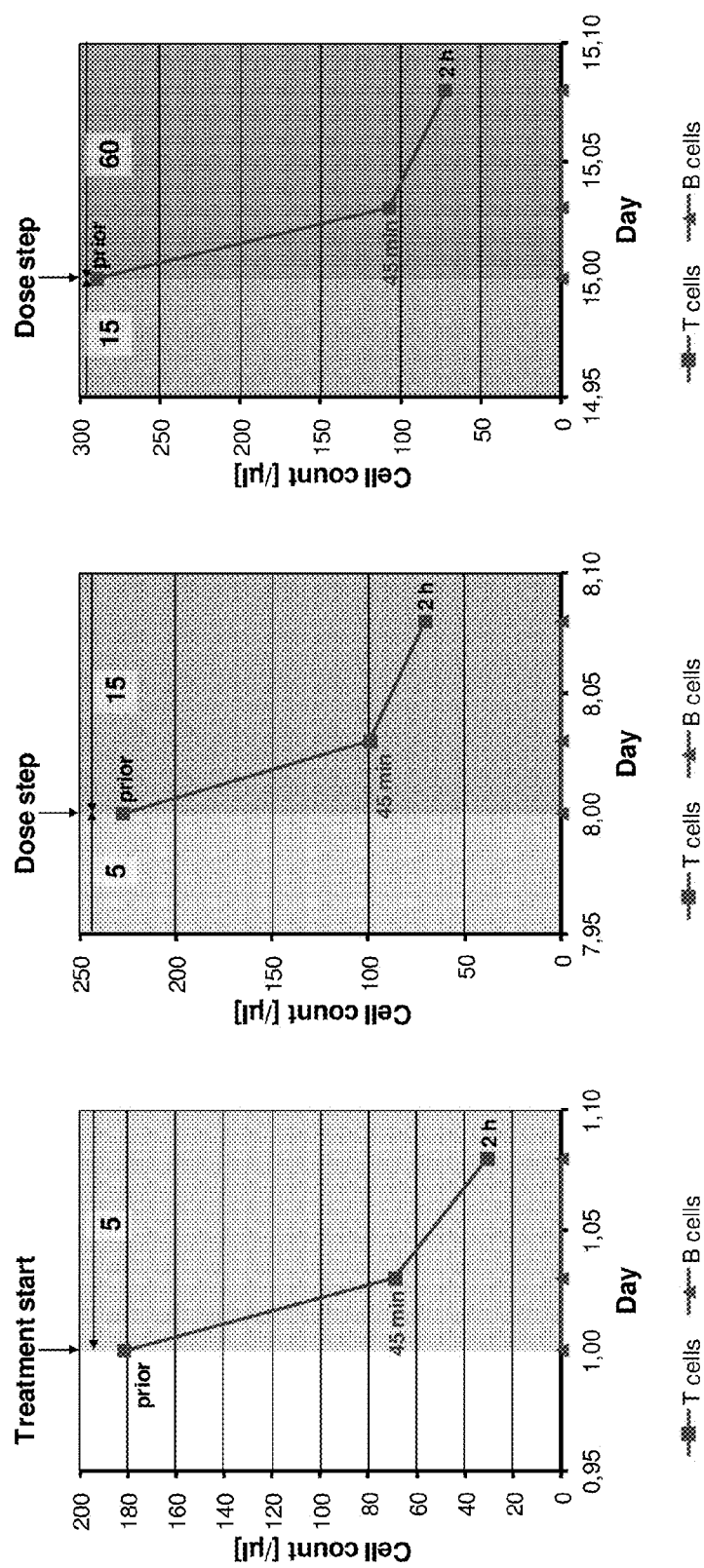
Figure 3:
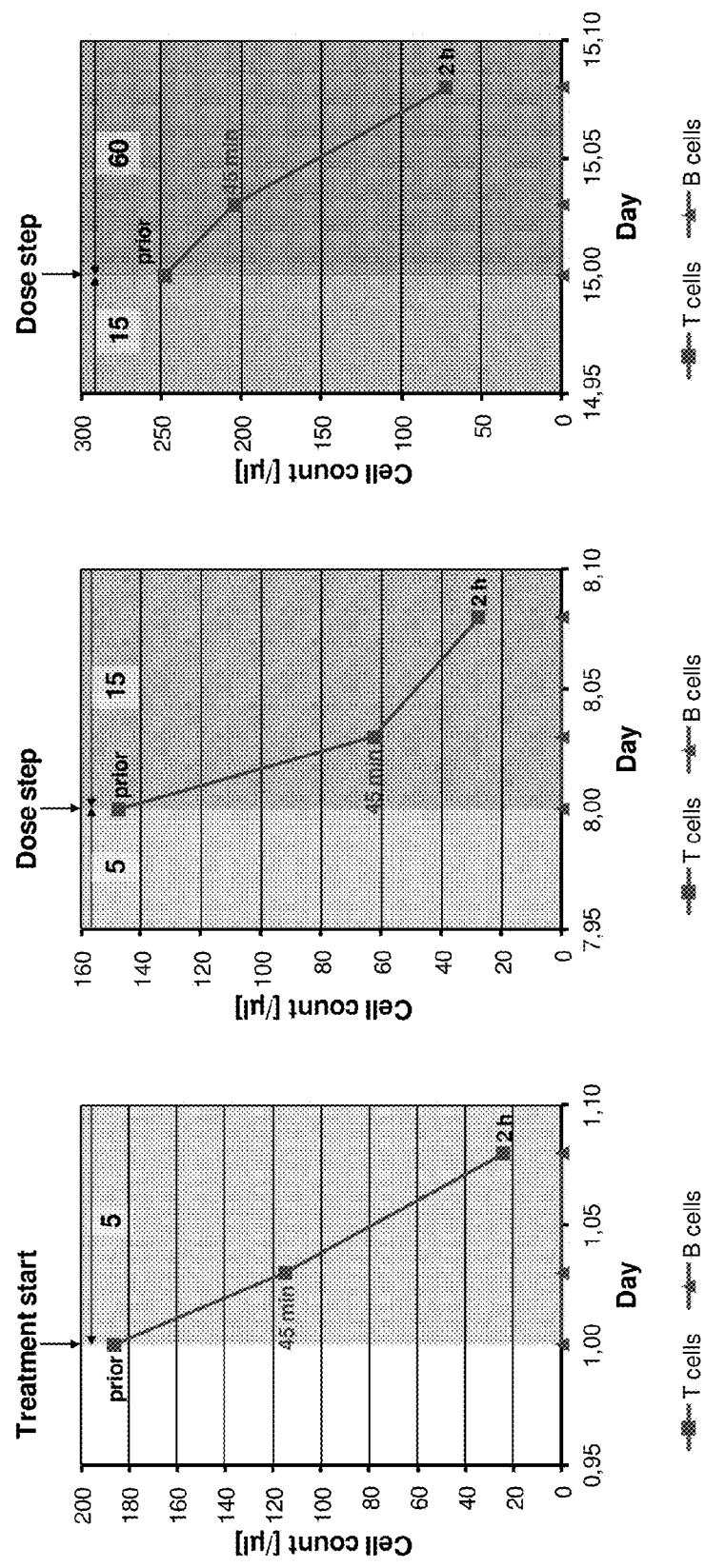
Figure 3:
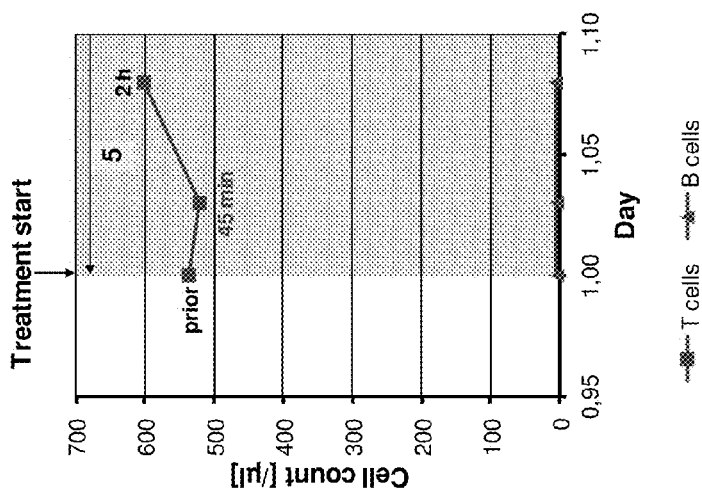
Figure 3:
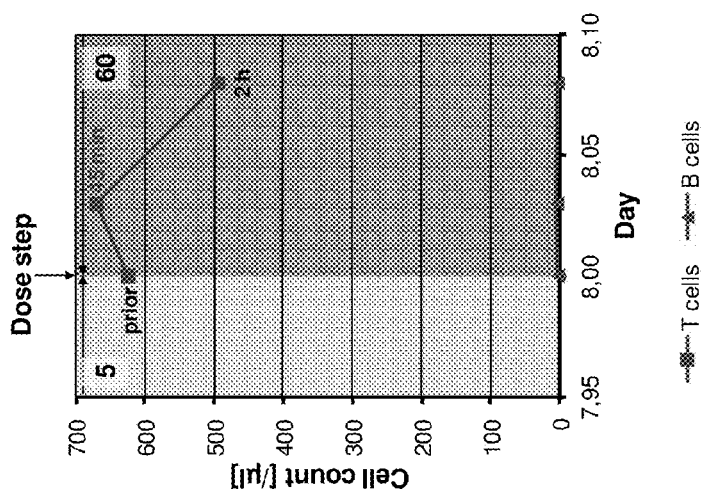
Figure 3:
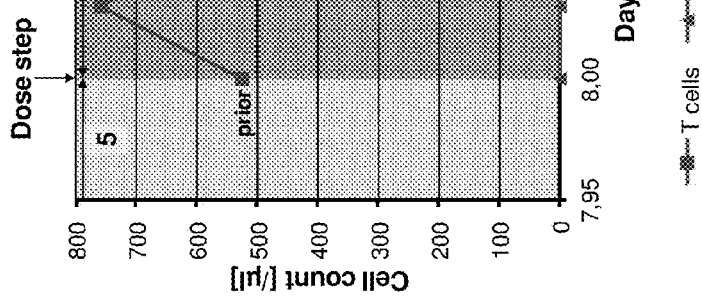

FIG. 3. Delayed T cell-redistribution kinetics in three patients who received PPS co-medication for the prophylaxis or amelioration of CNS AEs and the prevention of treatment discontinuations due to said CNS AEs (D, E, and F) compared to patients who did not receive PPS co-medication (A, B, and C).

T and B cell-counts are shown as absolute numbers per µl of peripheral blood. The time axis gives the period within the respective treatment cycle. Blinatumomab dose levels, e.g. 5, 15, or 60 µg/m²/day are indicated. The time points 0 h, 45 min, and 2 h after start of infusion or any dose step revealing differences in T cell-redistribution kinetics are indicated.

Figure 4:
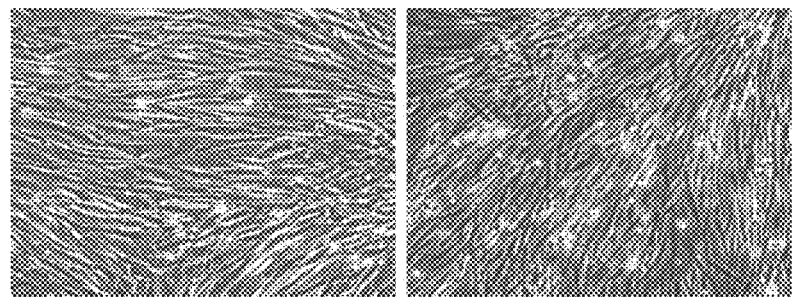
Figure 4:
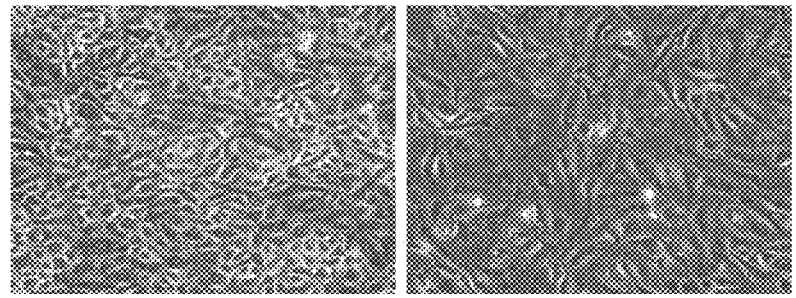

FIG. 4. Comparison of flow-cultivated versus statically cultivated endothelial cells.

A. HBMEC were cultivated in µ-slide Luer I$^{0.4}$ Collagen IV for 48 h under wall shear stress of 5 dyn/cm² (left) or under static conditions (right). B. HUVEC were cultivated in µ-slide Luer I$^{0.4}$ ibiTreat for 48 h under wall shear stress of 10 dyn/cm² (left) or under static conditions (right). Microscopic analysis was done with a 10× objective.

Figure 5:
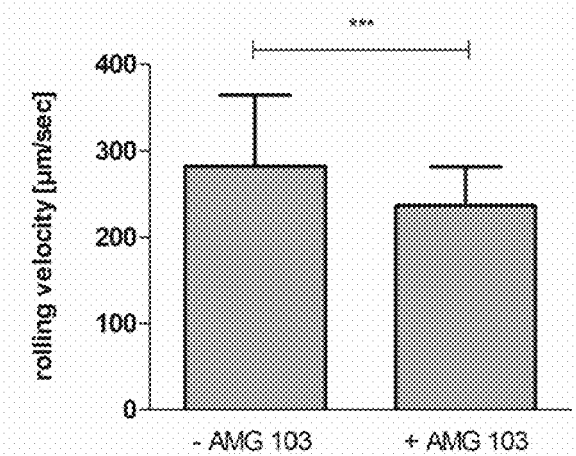
Figure 5:
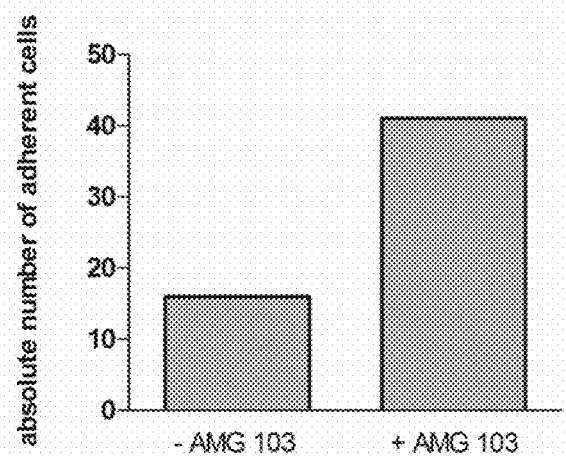
Figure 5:
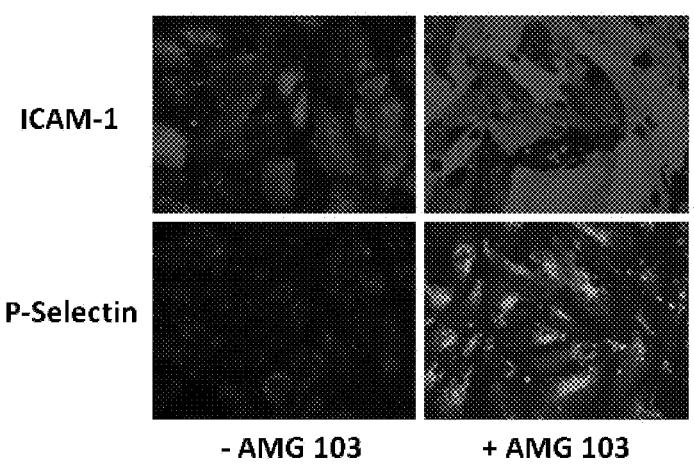

FIG. 5. Influence of AMG 103 on T cell-rolling and adhesion on HUVEC under short-term conditions.

Freshly isolated T cells were pre-incubated with or without AMG 103 (10 ng/ml) for 40 min at 37° C. prior to rolling of T cells on flow-cultivated HUVEC for 45 sec at shear stress of 1 dyn/cm². Rolling velocities and absolute numbers of adherent cells were determined microscopically by using the automated tracking module. A. Data represent the mean±SD T cell-rolling velocity. ***: P<0.001. B. Data represent absolute numbers of adherent T cells. C. Immunofluorescence staining of PFA-fixed HUVEC after rolling of T cells pre-incubated with (+AMG 103) or without (−AMG 103) AMG 103 at shear stress of 1 dyn/cm² for 45 sec. Microscopic analysis was done with a 20× objective and UV-light. ICAM-1 and P-selectin staining is shown in red and green, respectively.

Figure 6:
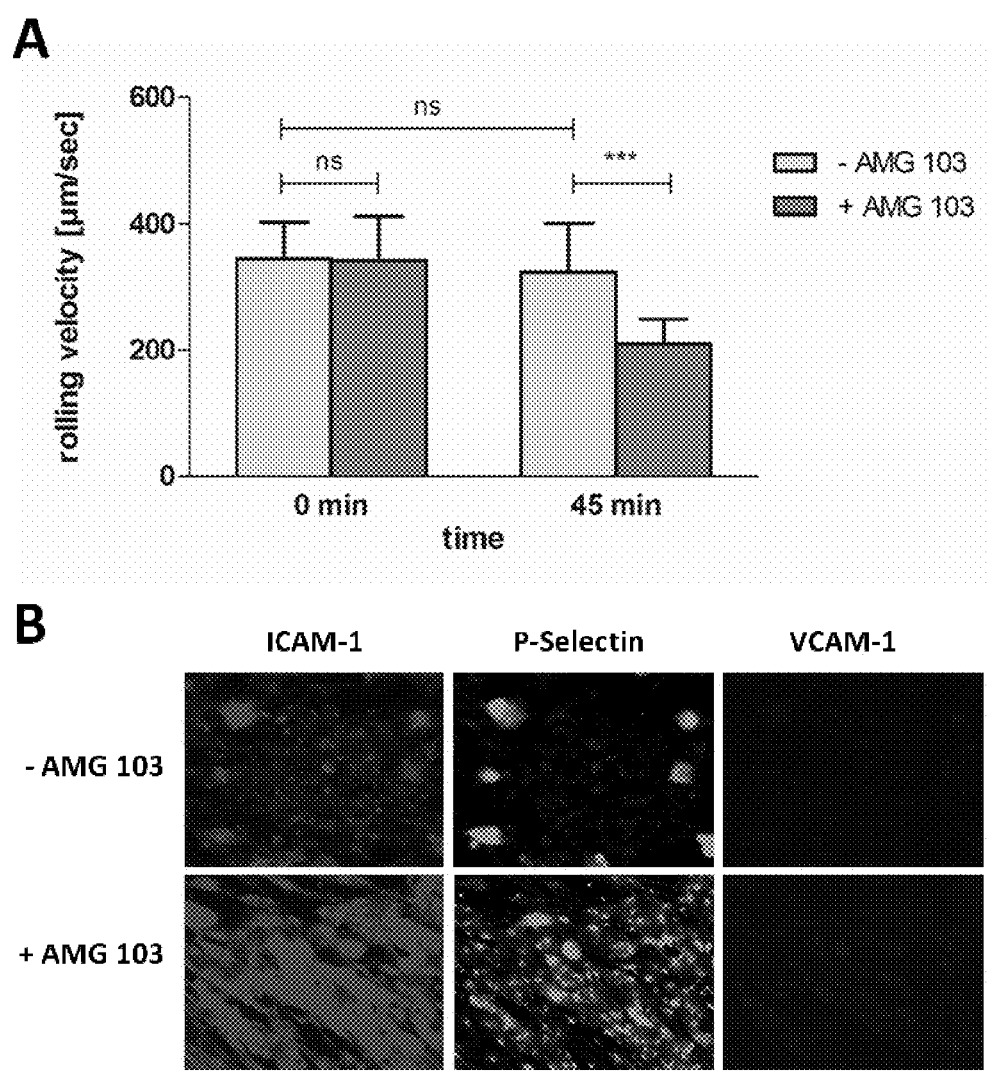

FIG. 6. Influence of AMG 103 on T cell-rolling on HBMEC under long-term conditions.

A. Freshly isolated T cells were used with or without addition of AMG 103 (10 ng/ml) for rolling on flow-cultivated HBMEC for 120 min at shear stress of 1 dyn/cm². Image acquisitions were performed immediately after start of rolling (0 min) and after 45 min of continuous rolling on HBMEC. Rolling velocities were determined microscopically by using the automated tracking module. Data represent the mean±SD T cell-rolling velocity. ***: P<0.001; ns: P>0.05 (not significant). B. Immunofluorescence staining of PFA-fixed HBMEC after T cell-rolling in the presence (+AMG 103) or absence (−AMG 103) of AMG 103 for 120 min at shear stress of 1 dyn/cm². Microscopic analysis was done with a 20× objective and UV-light. ICAM-1, P-selectin, and VCAM-1 staining is shown in red, green, and blue, respectively.

Figure 7:
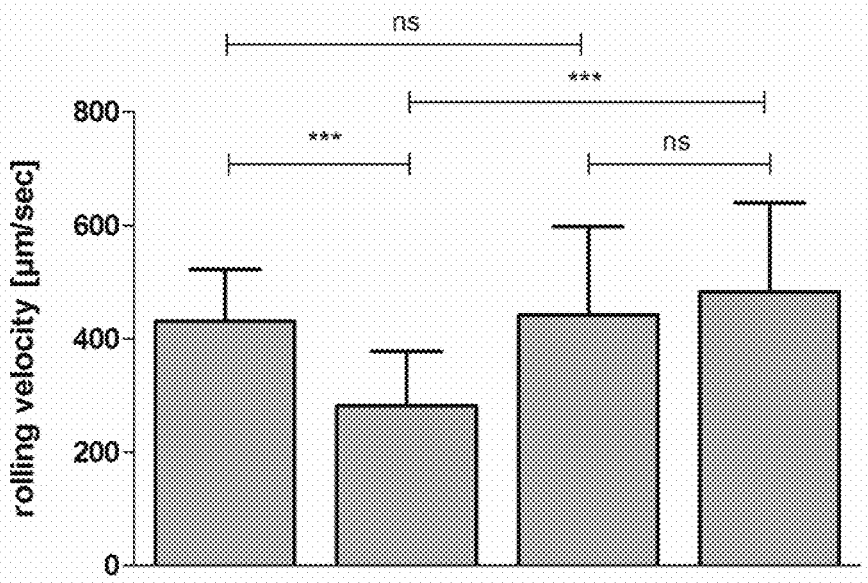
Figure 7:
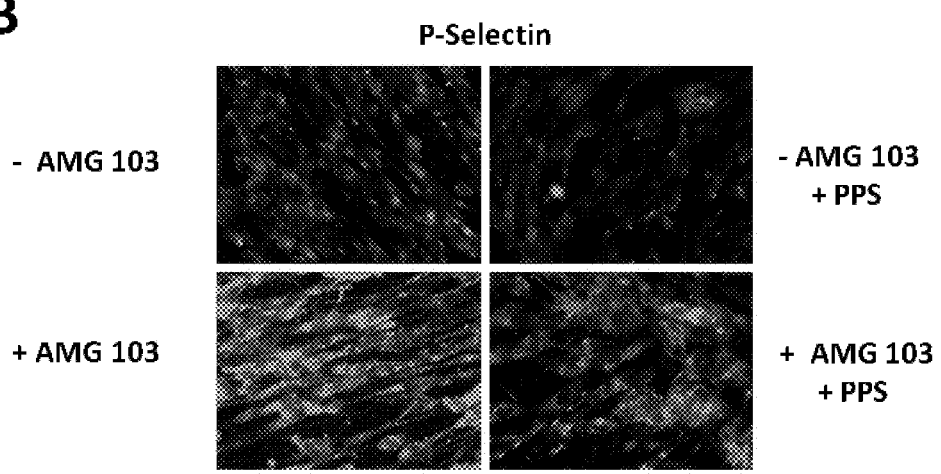

FIG. 7. Influence of PPS on T cell-rolling on histamine-stimulated HBMEC under long-term conditions.

A. Rolling of freshly isolated T cells on histamine-stimulated, untreated or PPS pre-incubated (200 µg/ml), flow-cultivated HBMEC was performed with or without AMG 103 (10 ng/ml) for 60 min of continuous rolling at shear stress of 1 dyn/cm². Rolling velocities were determined microscopically by manually tracking 30 T cells for each condition. Data represent the mean±SD T cell-rolling velocity at time point 45 min. ***: P<0.001; ns: P>0.05 (not significant). B. Immunofluorescence staining of PFA-fixed histamine-stimulated, untreated (—PPS) or PPS pre-incubated (+PPS) HBMEC after T cell-rolling in the presence (+AMG 103) or absence (−AMG 103) of AMG 103 for 60 min at shear stress of 1 dyn/cm². Microscopic analysis was done with a 20× objective and UV-light. P-selectin staining is shown in green.

Figure 8:
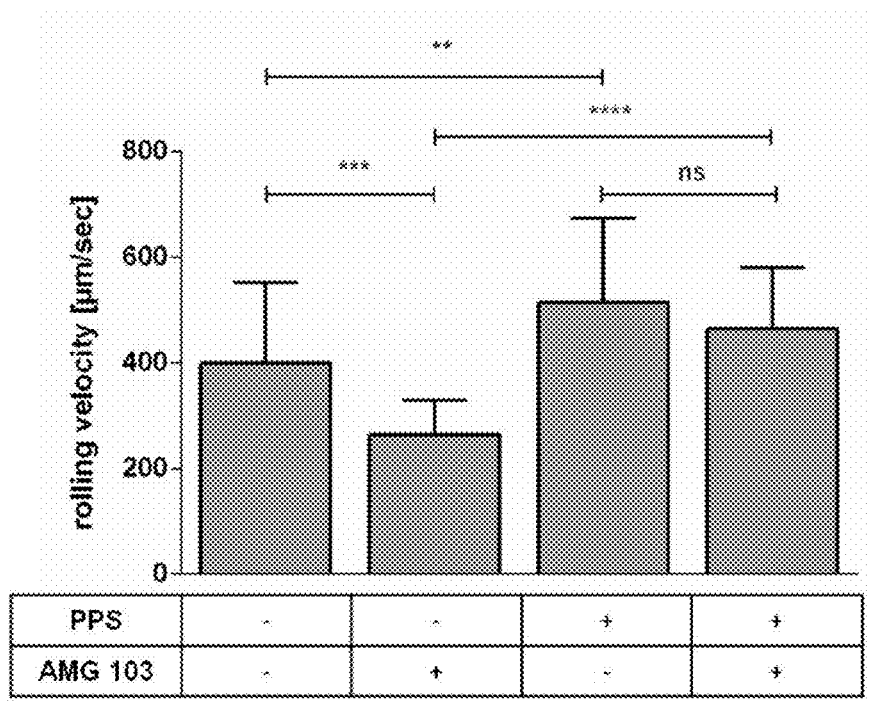

FIG. 8. Influence of PPS on T cell-rolling on non-stimulated HBMEC under long-term conditions.

Continuous rolling of freshly isolated T cells on non-stimulated, untreated or PPS pre-incubated (200 µg/ml), flow-cultivated HBMEC was performed with or without AMG 103 (10 ng/ml) for 60 min at shear stress of 1 dyn/cm². Rolling velocities were determined microscopically by manual tracking of 30 T cells for each condition. Data represent the mean±SD T cell-rolling velocity at time point 40 min. **: P<0.0001; *: P<0.001; **: P<0.01; ns: P≥0.05 (not significant).

Figure 9:
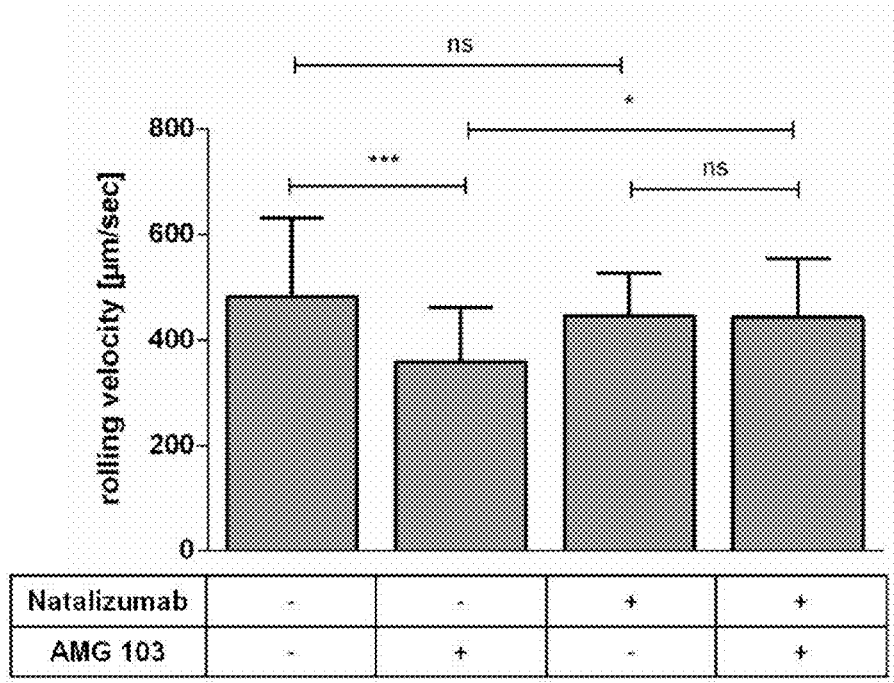

FIG. 9. Influence of natalizumab on T cell-rolling on non-stimulated HBMEC under long-term conditions.

Continuous rolling of freshly isolated T cells pre-incubated with or without natalizumab (1 µg/ml) for 10 min at 37° C. on non-stimulated, flow-cultivated HBMEC was performed with or without AMG 103 (10 ng/ml) for 60 min at shear stress of 1 dyn/cm². Rolling velocities were determined microscopically by manual tracking of 30 T cells for each condition. Data represent the mean±SD T cell-rolling velocity at time point 40 min. ***: P<0.001; *: P<0.05; ns: P≥0.05 (not significant).

Figure 10:
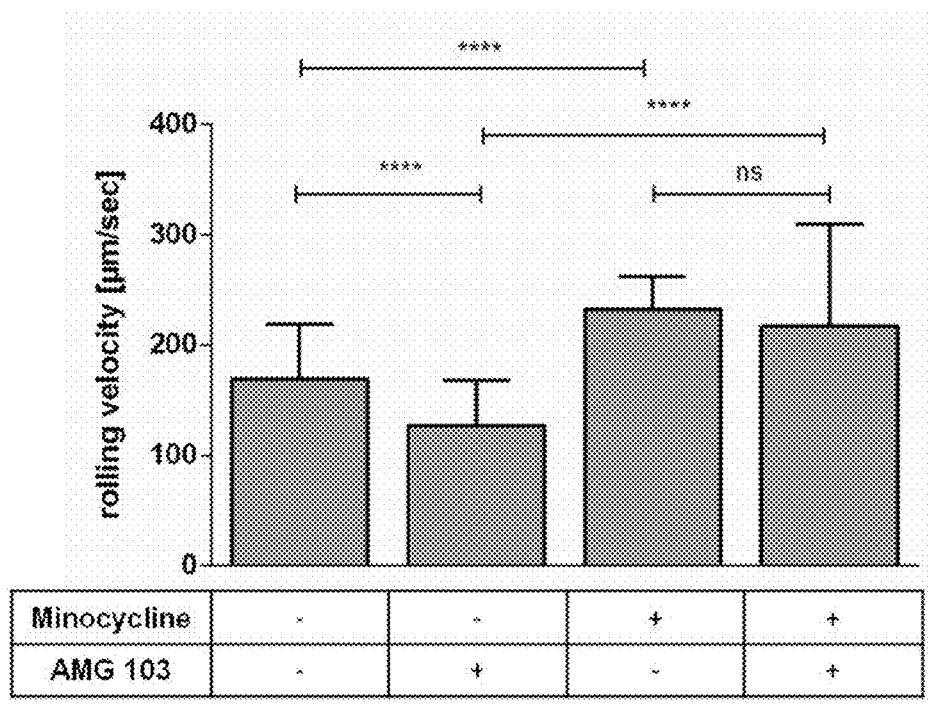

FIG. 10. Influence of minocycline on T cell-rolling on non-stimulated HUVEC under long-term conditions.

Continuous rolling of freshly isolated T cells pre-incubated with or without minocycline (50 µg/ml) for 2 h at 37° C. on non-stimulated, flow-cultivated HUVEC was performed with or without AMG 103 (10 ng/ml) for 45 min at shear stress of 1 dyn/cm². Rolling velocities were determined microscopically by using the automated tracking module. Data represent the mean±SD T cell-rolling velocity at time point 40 min. ****: P<0.0001; ns: P≥0.05 (not significant).

Figure 11:
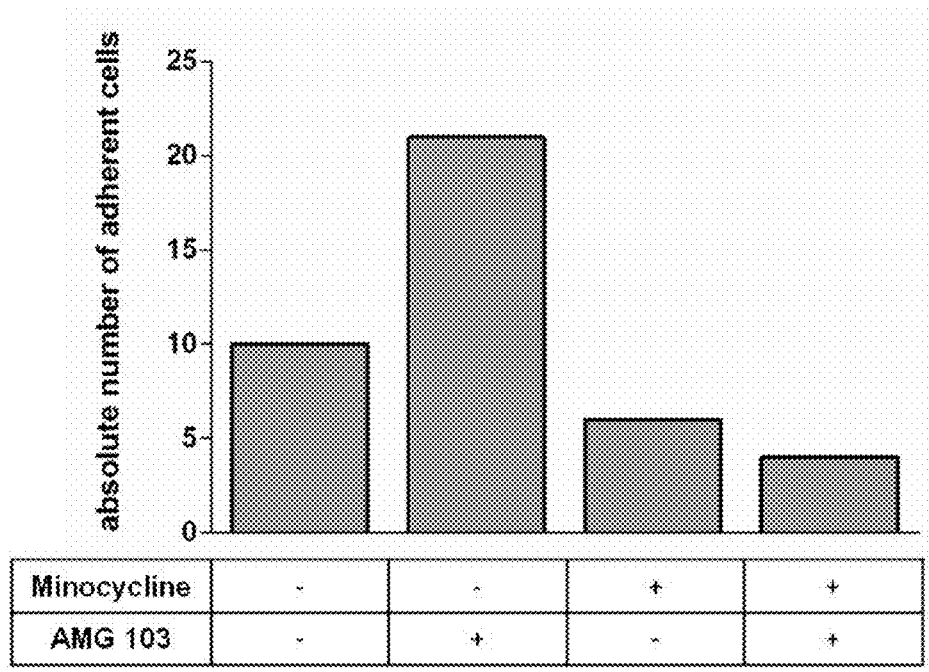

FIG. 11. Influence of minocycline on T cell-adhesion to non-stimulated HUVEC under long-term conditions.

Continuous rolling of freshly isolated T cells pre-incubated with or without minocycline (50 µg/ml) for 2 h at 37° C. on non-stimulated, flow-cultivated HUVEC was performed with or without AMG 103 (10 ng/ml) for 45 min at shear stress of 1 dyn/cm². Absolute numbers of adhering T cells were determined microscopically by manual cell counting. Data represent the absolute number of adhering T cells per image section at time point 40 min.

Figure 12:
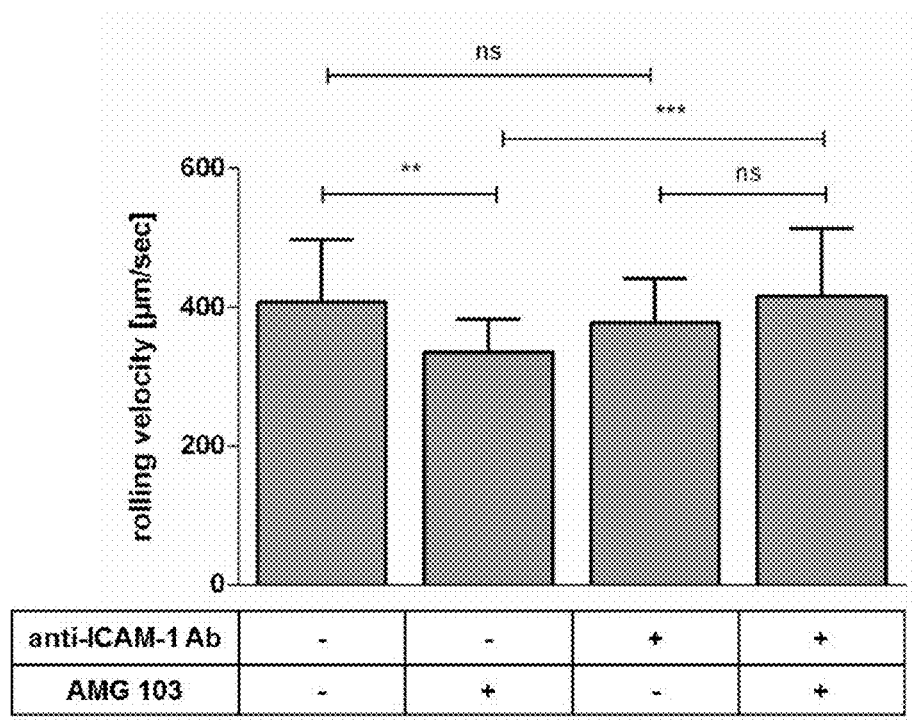

FIG. 12. Influence of an anti-ICAM-1 antibody on T cell-rolling on non-stimulated HBMEC under long-term conditions.

Continuous rolling of freshly isolated T cells on non-stimulated, untreated or with mouse anti-human ICAM-1 antibody pre-incubated (10 µg/ml), flow-cultivated HBMEC was performed with or without AMG 103 (10 ng/ml) for 45 min at shear stress of 1 dyn/cm². Rolling velocities were determined microscopically by manual tracking of 30 T cells for each condition. Data represent the mean±SD T cell-rolling velocity at time point 30 min. *: P<0.001; : P<0.01; ns: P≥0.05 (not significant). Ab: antibody.

Figure 13:
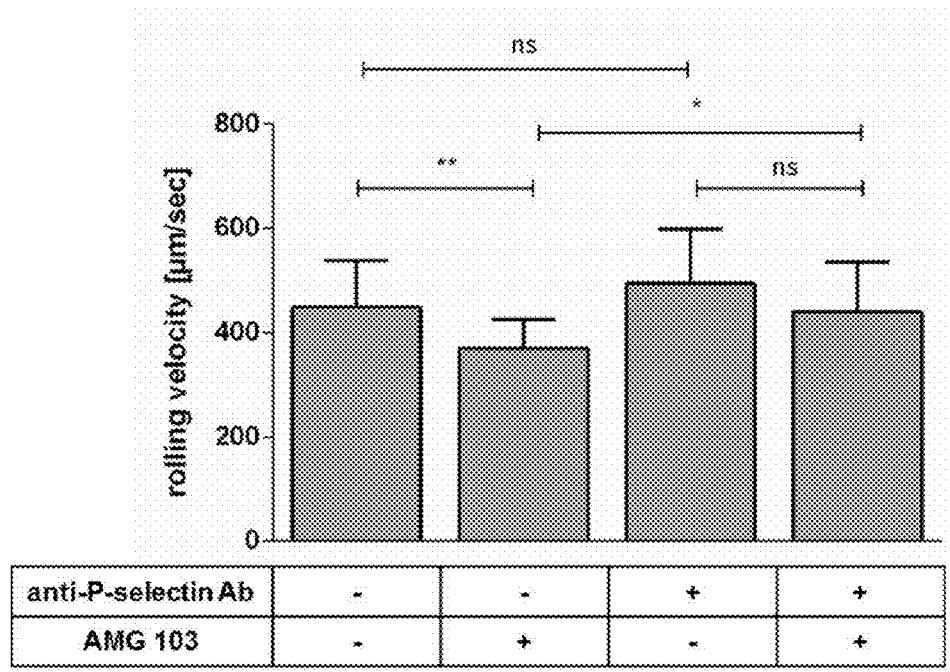

FIG. 13. Influence of an anti-P-selectin antibody on T cell-rolling on non-stimulated HBMEC under long-term conditions.

Continuous rolling of freshly isolated T cells on non-stimulated, untreated or with mouse anti-human P-selectin antibody pre-incubated (10 µg/ml), flow-cultivated HBMEC was performed with or without AMG 103 (10 ng/ml) for 45 min at shear stress of 1 dyn/cm². Rolling velocities were determined microscopically by manual tracking of 30 T cells for each condition. Data represent the mean±SD T cell-rolling velocity at time point 40 min. **: P<0.01; *: P<0.05; ns: P≥0.05 (not significant). Ab: antibody.

Figure 14:
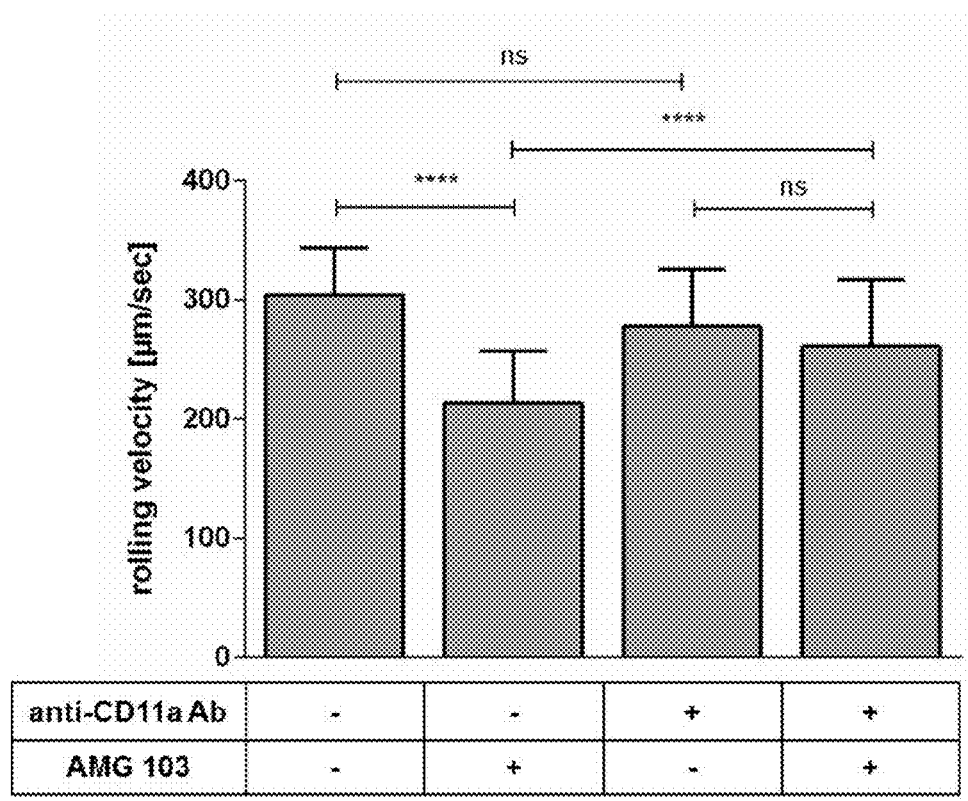

FIG. 14. Influence of an anti-CD11a antibody on T cell-rolling on non-stimulated HBMEC under long-term conditions.

Continuous rolling of freshly isolated T cells pre-incubated with or without anti-CD11a antibody (5 µg/ml) for 10 min at 37° C. on non-stimulated, flow-cultivated HBMEC was performed with or without AMG 103 (10 ng/ml) for 45 min at shear stress of 1 dyn/cm². Rolling velocities were determined microscopically by using the automated tracking module. Data represent the mean±SD T cell-rolling velocity at time point 10 min. ****: P<0.0001; ns: P≥0.05 (not significant). Ab: antibody.

Figure 15:
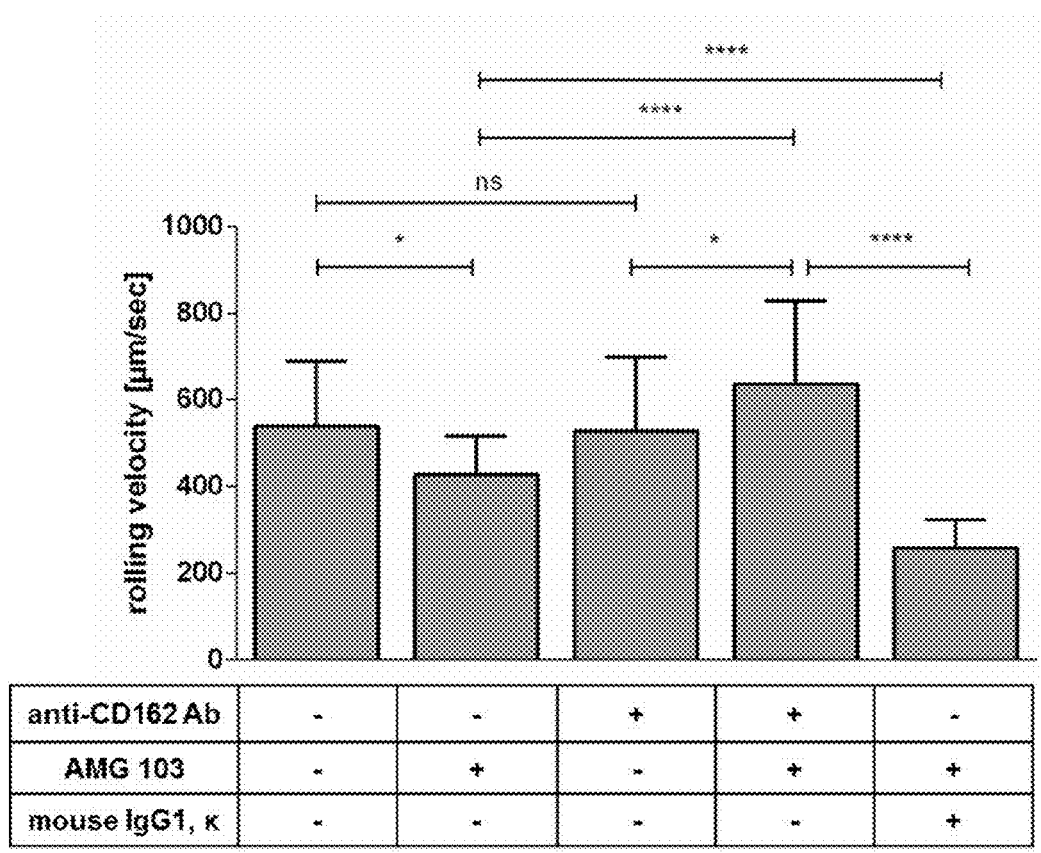

FIG. 15. Influence of an anti-CD 162 antibody on T cell-rolling on non-stimulated HBMEC under long-term conditions.

Continuous rolling of freshly isolated T cells pre-incubated either with or without anti-CD162 antibody (10 µg/ml) or with mouse isotype control antibody (10 µg/ml) for 10 min at 37° C. on non-stimulated, flow-cultivated HBMEC was performed with or without AMG 103 (10 ng/ml) for 45 min at shear stress of 1 dyn/cm². Rolling velocities were determined microscopically by manual tracking of 30 T cells for each condition. Data represent the mean±SD T cell-rolling velocity at time point 45 min. ****: P<0.0001; *: P<0.05; ns: P≥0.05 (not significant). Ab: antibody.

Figure 16:
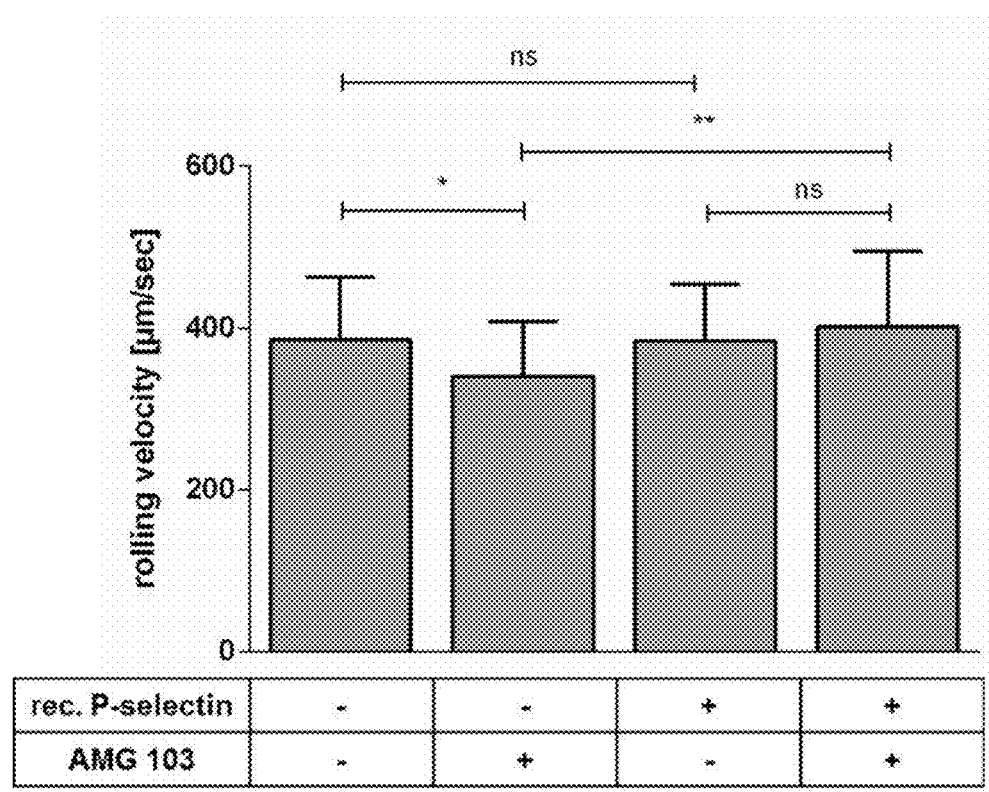

FIG. 16. Influence of recombinant P-selectin on T cell-rolling on non-stimulated HBMEC under long-term conditions.

Continuous rolling of freshly isolated T cells pre-incubated with or without recombinant P-selectin (5 µg/ml) for 15 min at 37° C. on non-stimulated, flow-cultivated HBMEC was performed with or without AMG 103 (10 ng/ml) for 45 min at shear stress of 1 dyn/cm². Rolling velocities were determined microscopically by manual tracking of 40 T cells for each condition. Data represent the mean±SD T cell-rolling velocity at time point 45 min. **: P<0.01; *: P<0.05; ns: P≥0.05 (not significant). rec.: recombinant.

Figure 17:
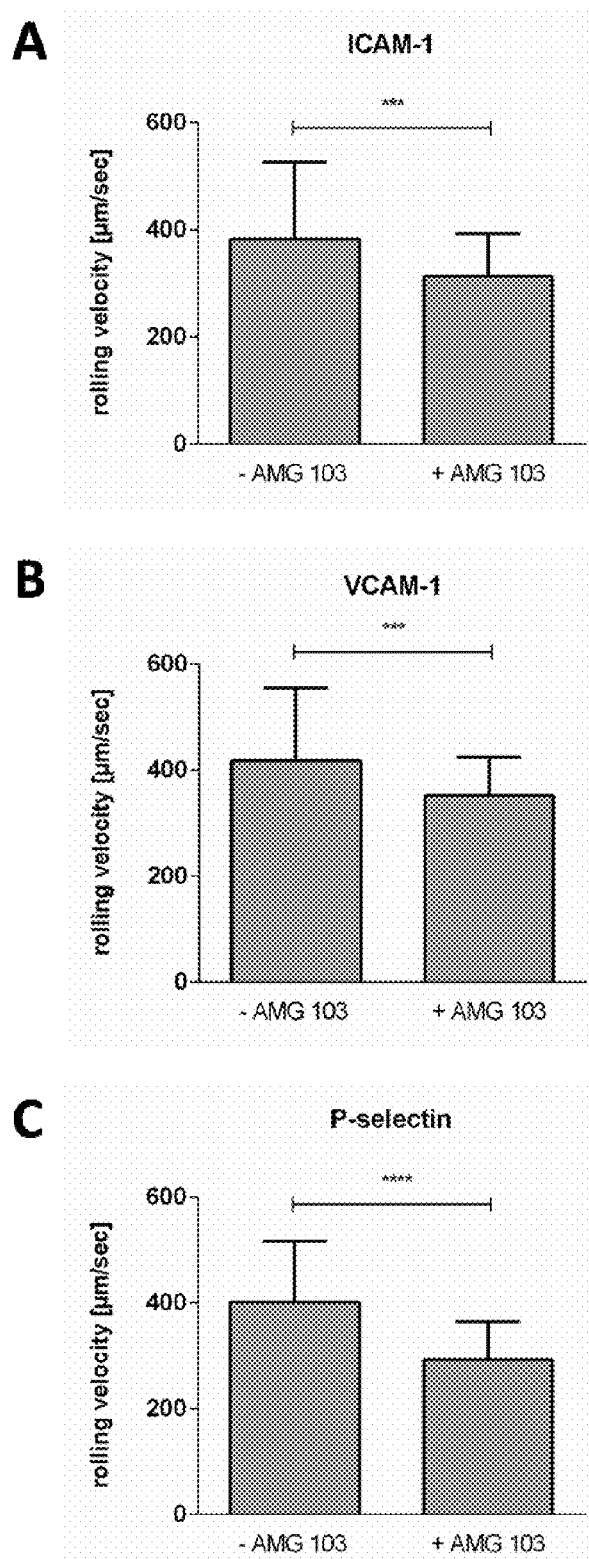
Figure 17:
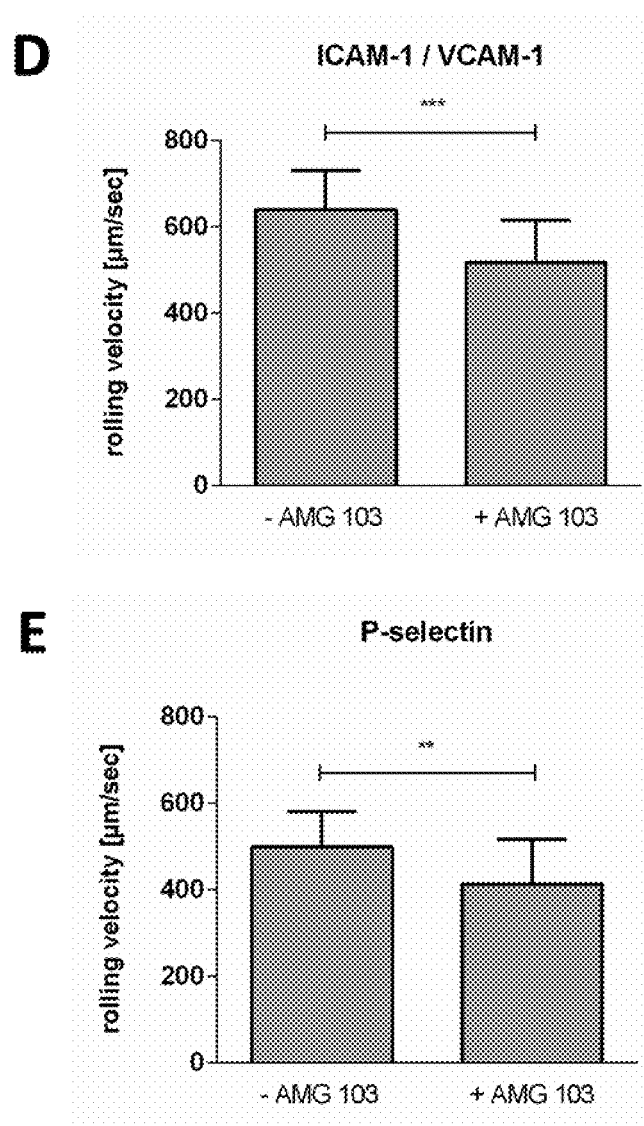

FIG. 17. Influence of Blinatumomab (AMG 103) on T cell-rolling on recombinant human adhesion molecules under semi short-term conditions.

Freshly isolated T cells were incubated with or without AMG 103 (10 ng/ml) for 35 min at 37° C. prior to continuous rolling with or without AMG 103 on recombinant proteins for 15 min at shear stress of 1.1 dyn/cm². Rolling velocities were determined microscopically by using the automated tracking module. Data represent the mean±SD T cell-rolling velocity at time point t=45 min on A. ICAM-1 (*: P<0.001), B. VCAM-1 (*: P<0.001), and at time point t=50 min on C. P-selectin (****: P<0.0001).

Furthermore, Jurkat E6.1 T cells were used as described above instead of freshly isolated T cells. Rolling velocities were determined microscopically by using the automated tracking module. Data represent the mean±SD T cell-rolling velocity at time point t=45 min on D. ICAM-1/VCAM-1 (*: P<0.001), and E. P-selectin (: P<0.01).

Figure 18:
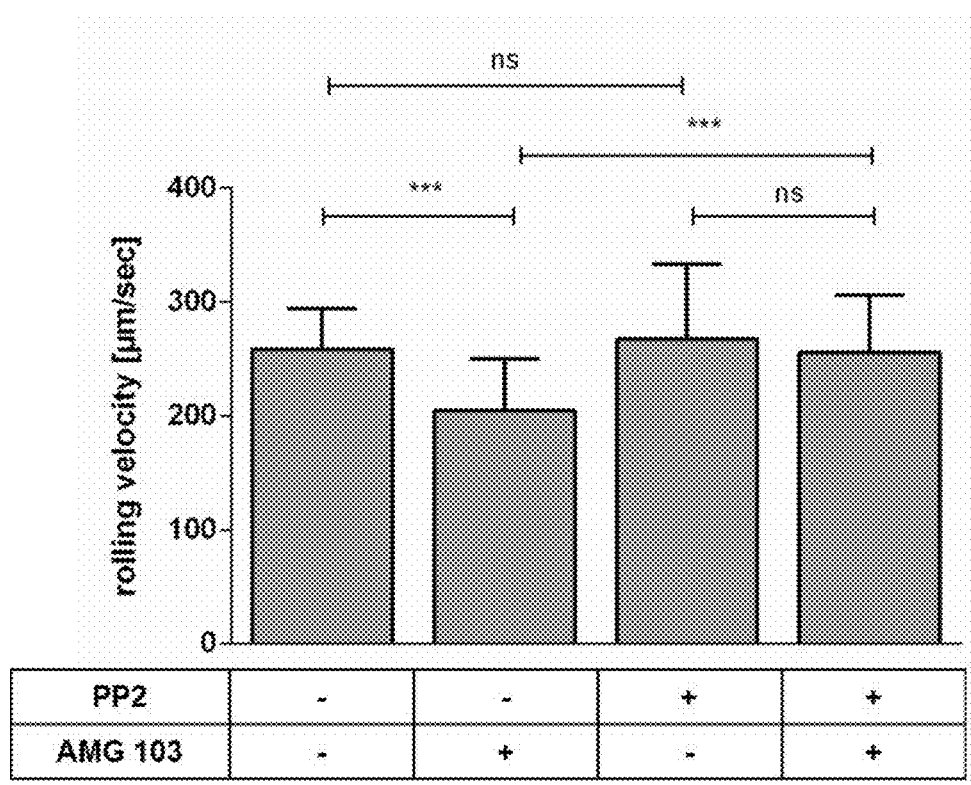

FIG. 18. Influence of Src kinase inhibitor PP2 on T cell-rolling on recombinant human adhesion molecules under semi short-term conditions.

Freshly isolated T cells pre-incubated with Src kinase inhibitor PP2 (15 µM) or vehicle control DMSO for 40 min at 37° C. were further incubated with or without AMG 103 (10 ng/ml) in the presence of PP2 or DMSO for 35 min at 37° C. prior to continuous rolling on recombinant human VCAM-1 for 15 min at shear stress of 1.1 dyn/cm². Rolling velocities were determined microscopically by manual tracking of 30 T cells for each condition. Data represent the mean±SD T cell-rolling velocity at time point t=40 min. ***: P<0.001; ns: P ≥0.05 (not significant).

DETAILED DESCRIPTION OF THE INVENTION

Figure 1:
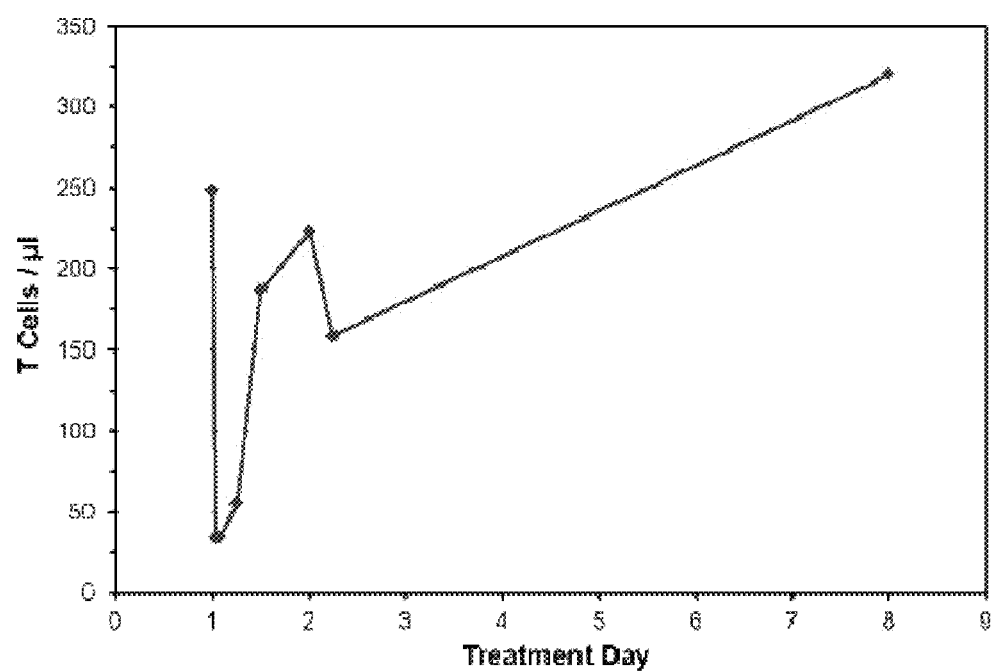
FIG. 1. Exemplary time courses of selected pharmacodynamic markers during treatment week 1 of a B-NHL patient treated at a Blinatumomab dose level of 60 µg/m²/day in a phase 1 clinical study.
Figure 1:
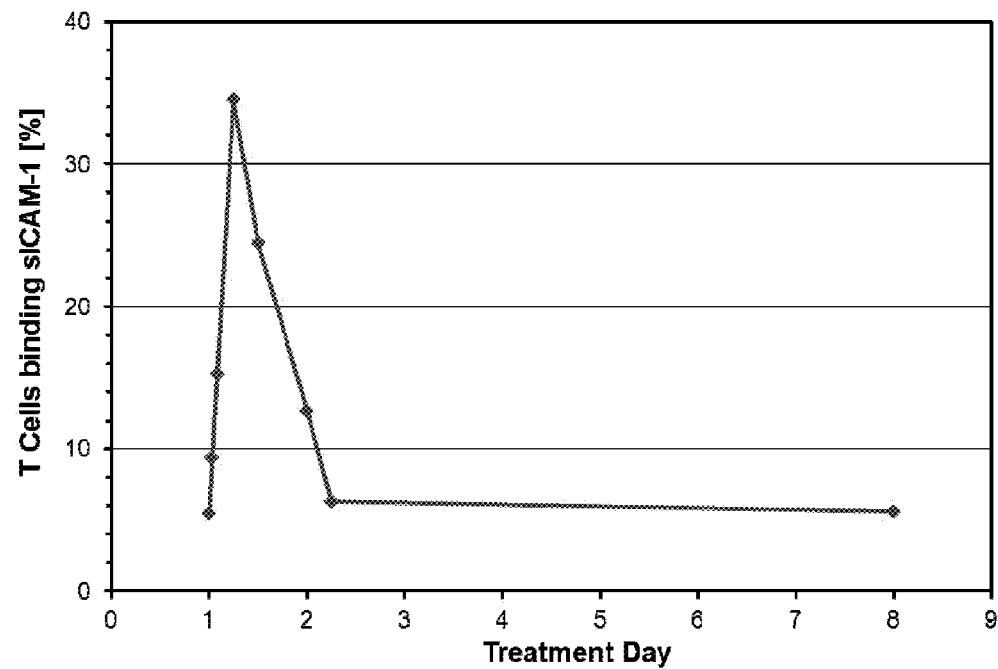
Figure 1:
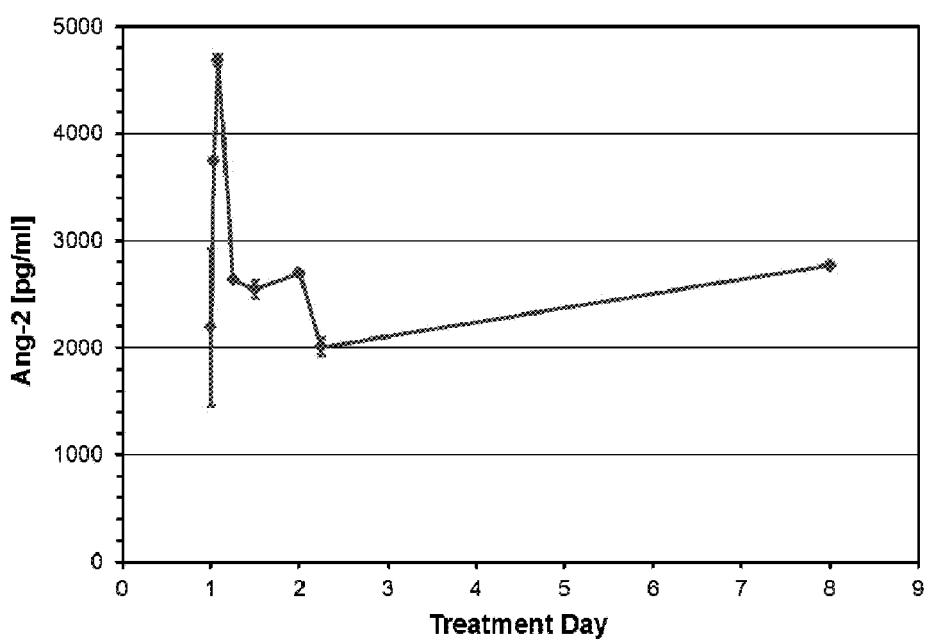
Figure 1:
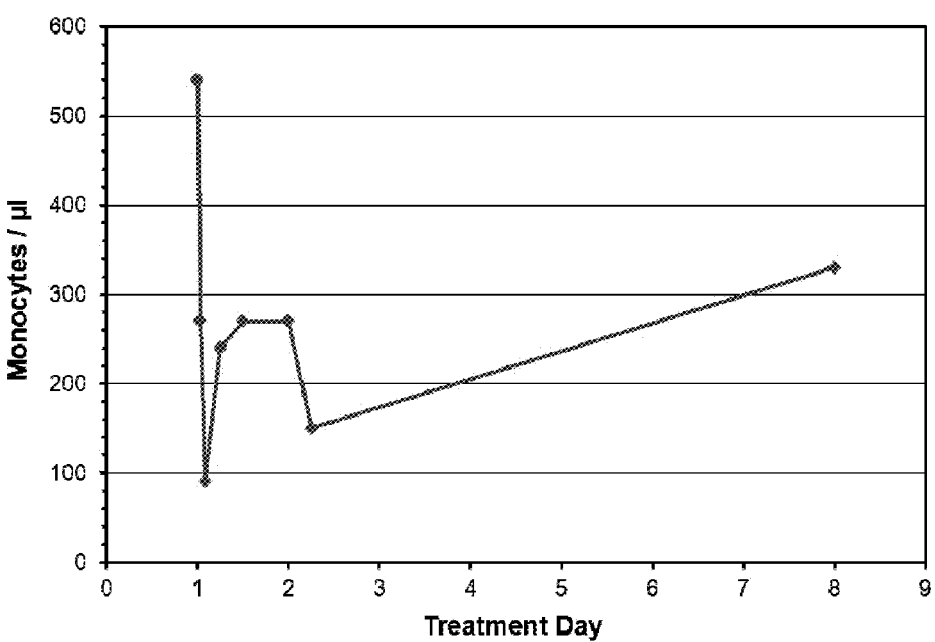

Various clinical studies evaluating the safety and efficacy of Blinatumomab have been conducted both in B-NHL (Bargou et al. Science. 2008; 321:974-7) and B-precursor ALL (Topp et al. J Clin Oncol. 2011; 29:2493-8). In B-NHL, doses as low as 0.005 mg/m²/day administered by continuous intravenous (civ) infusion over four weeks led to a complete and sustained elimination of B lymphoma cells in peripheral blood. Partial and complete responses were first observed at a dose level of 0.015 mg/m²/day and the majority of B-NHL patients treated at a dose level of 0.06 mg/m²/day experienced a substantial tumor regression. Blinatumomab also led to clearance of malignant B cells from bone marrow and liver in this indication. In B-precursor ALL, patients with both minimal residual disease and relapsed or refractory disease achieved a hematological complete response when treated with four-week civ infusions at a dose level of 0.015 mg/m²/day. These studies established clinical proof of concept for the high therapeutic potential of the bispecific single-chain antibody format in general and of Blinatumomab in special and validated its further development in B-NHL, ALL and CLL. Throughout these studies in B-NHL and B-precursor ALL several pharmacodynamic markers were assessed. Selected general characteristics shall be described hereafter: T cell-kinetics displayed a very distinguished profile irrespective of the dose level or the presence of circulating B cells. It was characterized by a swift redistribution after start of infusion and any dose step, i.e. a fast disappearance of circulating T cells within the first 6-12 hours and a subsequent reappearance during the following 2-7 days where high initial B cell-counts correlated with decelerated kinetics of T cell-reappearance (FIG. 1A). This course seemed to be triggered by any significant dose changes of Blinatumomab rather than absolute serum concentrations. In addition, T cell-adhesiveness was measured throughout treatment week 1 by analyzing binding of soluble ICAM-1-F$_c$ fusion proteins to LFA-1 on T cells. LFA-1 conformation shifted from a low affinity state before start of infusion to an intermediate affinity state after start of infusion and any dose step; the increased binding affinity to ICAM-1 peaked within 48 hours and returned to baseline within 5 days thereafter (FIG. 1B). This finding coincided with T cell-redistribution and supported the concept of Blinatumomab-induced T cell-adhesion to endothelium during redistribution.

Angiopoietin-2 (Ang-2) is a serum marker for endothelial activation (or even endothelial stress) that is stored in so-called Weibel-Palade bodies inside the cytoplasm of blood vessel-lining endothelial cells. Once endothelial cells get activated the vesicles fuse with the cell membrane and release the preformed Ang-2 into serum. Additionally, vesicle-bound adhesion molecules, e.g. P-selectin thereby appear on the cell surface thus further increasing adhesiveness of blood vessel-lining endothelial cells. Kinetics of Ang-2 serum concentrations resembled LFA-1-mediated increased T cell-adhesiveness by peaking during T cell-redistribution and declining back to baseline within treatment week 1. With maximal Ang-2 serum concentrations coinciding with sound T cell-disappearance this observation further indicated pronounced T cell-adhesion to blood vessel-lining endothelial cells (which thus got activated) as underlying mechanism of T cell-redistribution (FIG. 1C).

Although not directly engaged by Blinatumomab, monocytes displayed similar redistribution kinetics as T cells did. This finding further supported the concept of Blinatumomab-induced T cell-binding to endothelium leading to activation of endothelial cells which in turn up-regulated additional adhesion molecules and thereby allowed for broad binding of other mononuclear cells and thrombocytes (i.e. counts of circulating thrombocytes also decreased after start of infusion and any dose step). However, recovery of monocyte-counts in peripheral blood might be prolonged as activated (e.g. by adhering to activated endothelial cells) monocytes tended toward transmigration into underlying tissue before returning into circulation (FIG. 1D).

Based on the above, the present inventors conceived a hypothesis of a possible multi-step pathomechanism which might lead inter alia to central nervous system adverse events (CNS AE) caused by re-directed mammalian T-cells, (e.g. T-cells re-directed by Blinatumomab). This hypothesis is illustrated in FIG. 2.

FIG. 2A: Start of infusion or stepwise dose increase of Blinatumomab increase T cell-adhesion to blood vessel endothelium. FIG. 2B: Adherent T cells activate the endothelium and start to extravasate. Activated endothelial cells attract other peripheral blood leukocytes, e.g. monocytes which in turn cause transient neuroinflammation and perturbation of the blood CSF-barrier.

In order to prove the above hypothesis, the present inventors devised a co-medication scheme wherein Blinatumomab was administered concomitantly with the heparinoid pentosanpolysulfate (PPS), a small-molecule inhibitor of P-selectin (Höpfner et al. *J Pharm Pharmacol.* 2003; 55:697-706). Anti-leukocyte adhesion was successfully tested in a phase 1 clinical study by transiently infusing patients with PPS, prior to and after start of infusion of Blinatumomab as well as prior to and after any stepwise dose increase of Blinatumomab. P-selectin is known to mediate the first step of leukocyte adhesion to endothelial cells and seems to play a particular important role for the extravasation of circulating leukocytes via meningeal microvessels to the leptomeningeal space and the meninges (Kivisäkk et al. *Proc Natl Acad Sci USA.* 2003; 100:8389-94).

Three patients received in particular an intravenous PPS infusion during both the start-of-infusion phase at 5 μg/m²/day of Blinatumomab and the dose-step phase to 60 μg/m²/day after treatment week 1 (see also the Example section for further details). Despite having a high risk for developing CNS AEs due to their low B:T cell-ratios in the peripheral blood (see the underlying rationale as disclosed in PCT/EP2010/066207), none of these three patients had to discontinue treatment with Blinatumomab due to neurological adverse effects. Thus, much to the surprise of the present inventors it was indeed possible to mitigate the expected CNS AE in these patients by way of decreasing the adhesion of re-directed T-cells to the respective endothelial cells. Two out of the three patients achieved a complete response after 8 weeks of treatment with Blinatumomab; one patient had a stable disease after 4 weeks of treatment. Moreover, all three patients who had received intravenous PPS for the mitigation of potential CNS AEs showed delayed T cell-redistribution kinetics (in the absence of CD19-positive target cells) upon start of infusion or stepwise dose increase of Blinatumomab (FIG. 3). As described earlier, patients receiving Blinatumomab without co-medication with PPS consistently showed a rapid decline of T cell-counts in the peripheral blood already 45 minutes after start of infusion or stepwise dose increase (such as shown in FIGS. 3A, B, and C). By contrast, no decline of T cell-counts compared to the respective baseline values was observed 45 minutes after start of infusion or stepwise dose increase in all three patients who had received co-medication with PPS during both the start-of-infusion and the dose-step phase (FIGS. 3D, E and F). In two cases (D and E), there was even an increased T cell-count at 45 minutes. In one case (F), an increased T cell-count was still observed at 2 hours. The redistribution process and thus the underlying leukocyte adhesion to blood vessel endothelium was obviously slowed down by intervention with intravenous PPS as decreased T cell-counts in the peripheral blood were not detected earlier than 2 hours after start of infusion or stepwise dose increase of Blinatumomab.

Thus, a pharmacodynamic marker (i.e. delayed T cell-redistribution kinetics) for the prognosticated and intended mode of action of PPS was identified in patients. The clinical courses of the patients who received co-medication with PPS are consistent with these biomarker observations and also with the predictions of the current hypothesis on the pathomechanism of central nervous system adverse events. Accordingly, interfering with leukocyte adhesion to blood vessel endothelium (i.e. anti-leukocyte adhesion) is a mechanism-based interventional approach to prevent or ameliorate side effects such as CNS AEs caused by therapy which comprises re-directing of T-cells against target cells in a patient, such as Blinatumomab (AMG 103).

To further investigate and confirm that the initial binding of re-directed (human) T-cells to the respective (human) endothelial cells is indeed causative for the above mentioned CNS AE, the present inventors additionally established a test system which simulates rolling, tethering and adhesion of re-directed (human) T cells and other leukocytes on/to (human brain) microvascular endothelial cells under hydrodynamic flow conditions in an in vitro system ("flow system"). Further details of this test system can be derived from the appended examples which explain the experimental setup in great and sufficient detail (see the Example section). In this flow system the cellular rolling velocity as well as the number of adherent cells can be easily measured by those skilled in the art. Interference with any (molecular) step (i.e. requirement) of the multi-step rolling and adhesion process of peripheral blood cells on/to endothelial cells is expected to influence both the cellular rolling velocity as well as the number of adherent cells.

Addition of a CD3-specific binding domain, in particular Blinatumomab, to the flow system (thereby creating a re-directed T-cell), rapidly and significantly decreased T cell-rolling velocity on human brain microvascular endothelial cells (HBMEC). Simultaneously, HBMEC got activated by these re-directed T-cells as shown by up-regulation of adhesion molecules P-selectin, ICAM-1 and VCAM-1 on their cell surface (see FIG. 6B). However, the addition of T-cells without Blinatumomab (resulting in non-re-directed T-cells) did not influence the expression of the aforementioned endothelial adhesion molecules (see FIG. 6B). These observations resemble and correspond unequivocally to the T cell-redistribution as seen in patients and described in detail herein. Moreover, addition of the P-selectin blocking agent PPS to the flow system (i.e. pre-incubation of HBMEC with PPS) could efficiently block Blinatumomab-induced reduction of T cell-rolling velocity on HBMEC. As demonstrated after addition of Blinatumomab to the flow system, pre-incubation with PPS could neutralize any Blinatumomab-induced effects and revert T cell-rolling velocity back to levels comparable to those observed for T cell-rolling velocity without the addition of Blinatumomab to the flow system. Additionally, HBMEC got less activated when PPS was present in the flow system as shown by reduced cell surface expression of P-Selectin. These observations support the clinical finding that the addition of a compound which decreases or inhibits the binding of mammalian T-cells to mammalian endothelial cells (such as the P-selectin blocking agent PPS) is indeed able to decrease/delay T cell-adhesion to endothelial cells and thereby to prevent, amelioration and/or treatment clinical adverse events caused by a therapy which therapy comprises re-directing of T-cells against target cells in a patient.

Thus, the established flow system truly mimics T cell-rolling and adhesion inter alia of re-directed T-cells on/to blood vessel-lining endothelial cells under hydrodynamic flow conditions as observed during T cell-redistribution in patients treated with a medicament which comprises re-directing of T-cells against target cells, which can be achieved for example with a CD3-specific binding domain such as Blinatumomab. Especially, effects of infusing PPS to patients and adding PPS to the flow system on T cell-redistribution and T cell-rolling velocity, respectively, are very comparable in that PPS clearly interferes with T cell-adhesion to endothelial cells. According to the current hypothesis on the pathomechanism of CNS AEs, this interference (i.e. anti-leukocyte adhesion the decrease or inhibition of the binding of leucocytes, such as mammalian T-cells, and in particular the re-directed T-cells, to mammalian endothelial cells) may treat, prevent or ameliorate any adverse side effect, such as CNS AEs, caused by the administration of a medicament which comprises re-directing of T-cells against target cells to a patient (which can be achieved for example by CD3-specific binding domain or the CARs which are explained herein elsewhere). Moreover, the established flow system exemplified herein is capable of and can be used by those skilled in the art in a method of identifying a compound for use in a method of prophylaxis and/or amelioration and/or treatment of clinical adverse events caused by therapy which comprises re-directing of T-cells against target cells in a patient. The exemplified flow system is thus suitable for identifying/defining compounds with anti-adhesive properties (in particular compounds that decreases or inhibits the binding of mammalian T-cells to mammalian endothelial cells) that may be administered prior to, concurrently with and/or subsequently to the treatment of a patient with for example a CD3-specific binding domain for the prophylaxis or amelioration of CNS AEs caused by said CD3-specific binding domain. In other words, compounds demonstrating any anti-adhesive effects on leukocytes, in particular T cells, and most preferably re-directed T-cells in the flow system (i.e. for example reversion of CD3-specific binding domain-induced reduction of T cell-rolling velocity on blood vessel-lining endothelial cells comparable to the observed effects for the addition of PPS to the flow system) are expected to prevent or ameliorate any CNS AEs caused by treatment of a patient with a CD3-specific binding domain when administered prior to, concurrently with and/or subsequently to the treatment with said CD3-specific binding domain. The identification modification and/or confirmation of such compounds, is a straightforward task for the skilled person as it makes use of a well-established methodology.

The present inventors have thus paved the way to solve the technical problems identified herein.

DEFINITIONS

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The present invention relates in one embodiment to a compound which decreases or inhibits the binding of mammalian T-cells to mammalian endothelial cells for use in a method of prophylaxis and/or amelioration and/or treatment of clinical adverse events caused by therapy which comprises re-directing of T-cells against target cells in a patient.

The term "binding" of mammalian T-cells is to be understood to include any of the well-known sequential steps that typically characterize the movement of leucocytes out of the blood system, a process which is usually denoted as leucocyte extravasation. The aforementioned steps include the "rolling of the leucocytes" (the leucocytes slackly attach to the endothelial cells but are still pulled along with the blood stream, which results in a rolling motion of the leucocytes on the surface of the endothelial cells); the "tethering of the leucocytes" (sometimes also denoted as tight attachment— the leucocytes tightly attach to the endothelial cells, whereas the receptors for this interaction are different from those involved in the rolling process) and the "diapedesis step" (sometimes also denoted as transmigration—the previously mostly spherical leucocytes spread on the endothelium and actively transmigrate through the endothelial barrier). The compounds of the present invention either influence all of these steps, or just some of these steps, or just one of these steps.

The "compound" applied in the present invention (i.e. the compound which decreases or inhibits the binding of mammalian T-cells to mammalian endothelial cells) is one which, so to say, acts for example on the T cell side, i.e., on a T cell adhesion molecule, or on the endothelial cell side, i.e., on an endothelial cell adhesion molecule. However, the compound may also be one which acts on both the T cell side and the endothelial cell side. Said compound, when applied in the present invention, decreases or inhibits the binding of mammalian T cells to mammalian endothelial cells. As such a compound of the present invention is a compound that effects anti-adhesive effects, either on T cells or endothelial cells or both. For example, a compound may act on both T cell adhesion molecules and endothelial cell adhesion molecules or a mixture of two or more compounds is applied, one acts on T cell adhesion molecules and the further one(s) on endothelial cell adhesion molecules. An anti-adhesive effect preferably includes that the compound decreases or inhibits the binding of mammalian T-cells to mammalian endothelial cells. Preferred compounds of the present invention are depicted in Table 1.

It is also envisaged that the compound of the invention, i.e. a compound which decreases or inhibits the binding of mammalian T-cells to mammalian endothelial cells have, is able to increase the mean T cell-rolling velocity±SD (µm/sec) on HBMEC in the presence of +10 ng/ml AMG 103 by about 30, 40, 50, 60, 70, 80, 90, 100% or even more (see Example 2—the influence of PPS on Blinatumomab-induced reduction of mean T cell-rolling velocity as observed 45 min after addition of 10 ng/ml of Blinatumomab to the flow system was evaluated in long-term conditions. While AMG 103 significantly reduced mean T cell-rolling velocity±SD on HBMEC from 430±92 µm/sec (−AMG 103) to 281±96 µm/sec (+AMG 103), further addition of PPS to the flow system reverted this reduction to a mean T cell-rolling velocity±SD of 483±157 µm/sec as also observed in the absence of AMG 103 (i.e. −AMG 103, +PPS; 442±156 µm/sec).

It is known that T cells interact with endothelial cells via adhesion molecules, i.e. T cell adhesion molecules and endothelial cell adhesion molecules. Both T cell and endothelial cell adhesion molecules belong to the family of integrins, selectins and immunoglobulin G (IgG) superfamily. The latter are characterized by having an immunglobulin domain. CD44, as receptor of hyaluronic acid being present on the surface of endothelial cells is also regarded as T cell adhesion molecule.

Accordingly, preferred compounds that decrease or inhibit the binding of T cells to endothelial cells are integrins antagonists, selectin antagonists, Ig superfamily cell adhesion molecule antagonists or CD44 antagonists, respectively. Thus, a compound applied in the context of the present invention is preferably an integrin antagonist, a selectin antagonist, an Ig superfamily cell adhesion molecule antagonist, or a CD44 antagonist, respectively. Any of these antagonists is, in the context of the present invention, able to decrease or inhibit binding of mammalian T cells to mammalian endothelial cells.

Integrin antagonists are commonly known in the art; see e.g. Curley et al. (1999), Cellular and Molecular Life Science 56, 427-441. Selectin antagonists are known in the art; see e.g. Lefer (2010), Ann. Rev. Pharmacol Toxicol 40 283-294. CD44 antagonists are known in the art; see e.g. Hirota-Takahata (2007), J. Antiobiotics 60, 633-639. The same is true for IgG superfamily cell adhesion molecule antagonists.

A compound that decrease or inhibit the binding of T cells to endothelial cells is preferably an integrin antagonist, selectin antagonist, Ig superfamily cell adhesion molecule antagonist, or CD44 antagonist can preferably be tested and/or identified by applying such a potential antagonist to the flow chamber assay as described herein, in particular in Example 2, whereby an antagonist preferably increases the mean T cell-rolling velocity±SD (µm/sec) on HBMEC in the presence of +10 ng/ml AMG 103 by about 30, 40, 50, 60, 70, 80, 90, 100% or even more, as described above.

A compound acting on the T cell side as described above is characterized
(a) to be capable of binding to a T-cell adhesion molecule,
(b) to be capable of blocking the binding site of a T-cell adhesion molecule, and/or
(c) to inhibit or reduce the expression of a T-cell adhesion molecule.

A "T cell adhesion molecule" is a molecule that is present on the surface of a T cell and that functions or has a role in the adhesion of a T cell to other cells such as endothelial cells, the latter being preferred in the context of the present invention. Typically, a T cell adhesion molecule interacts with an adhesion molecule of an endothelial cell. The adhesion molecule of an endothelial cells may thus be regarded as ligand for the T cell adhesion molecule. An interaction between a T cell adhesion molecule and a ligand present on the surface of an endothelial cell usually takes place between a binding site of a T cell adhesion molecule (i.e., a ligand binding site) and its designated ligand, i.e., an adhesion molecule of an endothelial cell.

A T cell adhesion molecule as described herein has preferably an immunoglobulin superfamily domain. Such an adhesion molecule is preferably an integrin that has preferably an RGD-binding domain, such as alpha4-integrin, alphaL-beta2-integerin, alphaL-integrin, beta7-integrin; a selectin such as L-selectin, or CD44. T cells use integrins and/or selectins and/or CD44 to migrate in and out of vessels and/or lymph nodes to then migrate, e.g. into other tissues, the leptomeningeal or perivascular space. CD44 mainly acts as receptor of hyaluronic acid which is present on the surface of endothelial cells which line up vessels.

A compound of the present invention is in one embodiment characterized to be capable of binding to a T cell adhesion molecule. As such, a compound binds and thus preferably sheds the T cell adhesion molecule such that the T cell adhesion molecule is diminished, preferably no longer able to interact with an endothelial adhesion molecule. As a consequence of a compound binding to a T cell adhesion molecule, a T cell is at least diminished, preferably no longer able to interact with an endothelial adhesion molecule. A preferred compound that binds to a T cell adhesion molecule is a molecule that is capable of binding to another molecule, such as a lipocalin mutein, or an antibody, preferably a monoclonal antibody. Preferably, the binding molecule can be specifically targeted to the T cell adhesion molecule. Since an antibody fulfills that criterion, a preferred compound that binds to a T cell adhesion molecule is an antibody, preferably a monoclonal antibody, such as Natalizumab, Efalizumab, or Etrolizumab.

A compound of the present invention is additionally or alternatively characterized to be capable of blocking the binding site of a T-cell adhesion molecule. "Blocking" means to prevent the binding site of a T cell adhesion molecule from interacting with its ligand, preferably with the binding site of its ligand, on the endothelial cell. As a consequence of a compound blocking the binding site of a T cell adhesion molecule, a T cell is at least diminished, preferably no longer able to interact with an endothelial adhesion molecule. Non-limiting examples of binding sites of a T cell adhesion molecule are binding sites for ICAM-1, ICAM-2, ICAM-3, VCAM-1, MadCAM, GlyCAM, CD31 (PECAM-1), CD62P (P-selectin), CD62E (E-selectin), CD62L, fibrinogen, and chondroitin.

Preferred compounds that block the binding site of a T-cell adhesion molecule are soluble fragments of cell adhesion molecules of endothelial cells, said soluble fragments are preferably modified so as to bind to the binding site of a T cell adhesion molecule without causing a physiological effect such as the transduction of a signal to the T cell.

A preferred compound that blocks the binding site of a T cell adhesion molecule is an antibody, preferably a monoclonal antibody that blocks an ICAM-1, ICAM-2, ICAM-3, VCAM-1, MadCAM, GlyCAM, CD31, CD62P, CD62E, CD62L. fibrinogen, and/or chondroitin binding site on a T cell adhesion molecule, e.g. on VLA-4 and/or LPAM-1, respectively. Such an antibody is Natalizumab which is thus a preferred compound applied in the present invention.

Also preferred as a compound that is applied in the present invention is an antibody, preferably monoclonal antibody that blocks an ICAM-1 binding site on a T cell adhesion molecule. Such an antibody is Efalizumab which is thus a preferred compound applied in the present invention.

Further preferred as a compound that is applied in the present invention is an antibody, preferably monoclonal antibody that blocks a VCAM-1 and/or MadCAM binding site on a T cell adhesion molecule. Such an antibody is Etrolizumab which is thus a preferred compound applied in the present invention.

Another preferred compound is AJM300, a small molecule that blocks binding sites of T cell adhesion molecules. Another preferred compound is SAR 1118, a small molecule that blocks the ICAM-1, ICAM-2 and/or ICAM-3 binding site on a T cell adhesion molecule.

Another further preferred compound is BOL-303225-A, a small molecule that acts an antagonist of the integrins alphaLbeta2 and/or alphaMbeta2.

Another preferred compound is a chelator, preferably a chelator for bivalent cations, such as calcium. A preferred chelator is Ethylenediaminetetraacetic acid (EDTA).

Hyaluronic acid (HA) or chondroitin sulfate are further preferred compounds, since both are known to block the HA and E-selectin binding site on CD44, thereby blocking the interaction between CD44 on T cells and endothelial cells.

A compound of the present invention is additionally or alternatively characterized by inhibiting or reducing the expression of a T-cell adhesion molecule. Such a compound may act on the expression including transcription and/or translation of genes encoding T cell adhesion molecules, such as suppressing gene expression, interfering with transcription, splicing, or translation. This could, for example, be achieved by RNA interference by means and methods known in the art. However, other compounds are known which reduce the expression of a T cell adhesion molecule, such as Minocycline which reduces LFA-1 expression, (acetyl-)salicyclic acid which reduces L-selectin expression, Astilbin or Flavonoids which reduce CD44 expression (see also Table 1 herein). These compounds are preferred compounds that are applied in the context of the present invention, with Minocycline being more preferred The compound acting on the endothelial cell side is characterized
(a) to be capable of binding to an endothelial adhesion molecule,
(b) to be capable of blocking the binding site of an endothelial adhesion molecule, and/or
(c) to inhibit or reduce the expression of an endothelial adhesion molecule, An "endothelial cell adhesion molecule" is a molecule that is present on the surface of an endothelial cell and that functions or has a role in the adhesion of endothelial cells to other cells such as leukocytes, in particular T cells or monocytes. Typically, an adhesion molecule of an endothelial cell interacts with a T cell adhesion molecule. The adhesion molecule of a T cell may thus be regarded as ligand for the endothelial cell adhesion molecule. An interaction between an endothelial cell adhesion molecule and a ligand present on the surface of a T cell usually takes place between a binding site of an endothelial cell adhesion molecule (i.e., a ligand binding site) and its designated ligand, i.e., an adhesion molecule of an T cell.

An endothelial cell adhesion molecule as described herein has preferably an immunoglobulin superfamily domain. Such an adhesion molecule is preferably an integrin that has preferably an RGD-binding domain, such as ICAM-1, ICAM-2, ICAM-3, VCAM-1, GlycAM-1, or MadCAM. Via integrins and/or selectins endothelial cells communicate and interact with, e.g. T cells such that T cells can finally extravasate and migrate as described above.

A compound of the present invention is in one embodiment characterized to be capable of binding to an endothelial adhesion molecule. As such, a compound binds and thus preferably sheds the endothelial adhesion molecule such that adhesion of T cells in particular is diminished, preferably endothelial cells are no longer able to interact with a T cell adhesion molecule. As a consequence of a compound binding to an endothelial cell adhesion molecule, an endothelial cell is at least diminished, preferably no longer able to interact with a T cell adhesion molecule. A preferred compound that binds to an endothelial adhesion molecule is a molecule that is capable of binding to another molecule, such as a lipocalin mutein, or an antibody, preferably a monoclonal antibody. Preferably, the binding molecule can be specifically targeted to the endothelial adhesion molecule. Since an antibody fulfills that criterion, a preferred compound that binds to an endothelial adhesion molecule is an antibody, preferably a monoclonal antibody, such as PF-00547659.

A compound of the present invention is additionally or alternatively characterized to be capable of blocking the binding site of an endothelial adhesion molecule. "Blocking" means to prevent the binding site of an endothelial adhesion molecule from interacting with its ligand, preferably with the binding site of its ligand, on the T cell. As a consequence of a compound blocking the binding site of an endothelial adhesion molecule, an endothelial cell is at least diminished, preferably no longer able to interact with a T cell adhesion molecule. Non-limiting examples of binding sites of an endothelial cell adhesion molecule are binding sites for alpha4-integrins, alphaL-beta2-integrins, alphaL-integrins, beta7-integrins.

Preferred compounds that block the binding site of an endothelial cell adhesion molecule are soluble fragments of cell adhesion molecules of T cells, said soluble fragments are preferably modified so as to bind to the binding site of an endothelial cell adhesion molecule without causing a physiological effect such as the transduction of a signal to the T cell.

A preferred compound that blocks the binding site of an endothelial cell adhesion molecule is an antibody, preferably a monoclonal antibody that blocks an alpha4-integrins, alphaL-beta2-integrins, alphaL-integrins, beta7-integrins binding site on an endothelial cell adhesion molecule.

Also preferred as a compound that is applied in the present invention is an antibody, preferably monoclonal antibody that binds an endothelial cell adhesion molecule, such as ICAM-1, ICAM-2, ICAM-3, VCAM-1, GlycAM-1, MadCAM, or PECAM-1.

Further preferred as a compound that is applied in the present invention is an antibody, preferably monoclonal antibody that binds P-selection (CD62P). Such an antibody is Inclacumab.

Another preferred compound is thrombin, preferably at low pM concentrations, that blocks binding sites of endothelial cell adhesion molecules.

A further preferred compound is pentosanpolysulfate (PPS) that blocks the PSGL-1 binding site on an endothelial cell adhesion molecule.

A compound of the present invention is additionally or alternatively characterized by inhibiting or reducing the expression of an endothelial cell adhesion molecule. Such a compound may act on the expression including transcription and/or translation of genes encoding endothelial cell adhesion molecules, such as suppressing gene expression, interfering with transcription, splicing, or translation. This could, for example, be achieved by RNA interference by means and methods known in the art. However, other compounds are known which reduce the expression of an endothelial cell adhesion molecule, such as rosuvastatin, a small molecule, that reduces expression of VCAM-1.

The present invention also relates to a method of identifying a compound for use in a method of prophylaxis and/or amelioration and/or treatment of clinical adverse events caused by therapy which comprises re-directing of T-cells against target cells in a patient, comprising:
(a) contacting said compound with a mammalian T-cell, a mammalian endothelial cell, a T-cell adhesion molecule and/or an endothelial adhesion molecule; and
(b) evaluating whether said compound:
(i) decreases or inhibits the binding of mammalian T-cells to mammalian endothelial cells;
(ii) is capable of binding to a T-cell adhesion molecule,
(iii) is capable of blocking the binding site of a T-cell adhesion molecule, (iv) inhibits or reduces the expression of a T-cell adhesion molecule,
(v) is capable of binding to an endothelial adhesion molecule,
(vi) is capable of blocking the binding site of an endothelial adhesion molecule, and/or
(vii) inhibits or reduces the expression of an endothelial adhesion molecule.

It is intended to use for example the flow system disclosed herein for that purpose. A non-exclusive list of possible other in vitro assays which may be used for identifying a compound for use in a method of prophylaxis and/or amelioration and/or treatment of clinical adverse events caused by therapy which comprises re-directing of T-cells against target cells in a patient, are depicted below:

Transmigration assays (Rohnelt, Hoch et al. 1997, Ding, Xiong et al. 2000)

Adhesion assays with immobilized adhesion molecules (Gerli, Gresele et al. 2001, Valignat, Theodoly et al. 2013)

Adhesion assays with endothelial cells and T cells under static conditions (Mobley and Shimizu 2001)

Interference of such compounds with adhesion molecules on T cells in flow cytometric assays (Bucolo, Maltese et al. 2008)

Bucolo, C., A. Maltese, F. Maugeri, K. W. Ward, M. Baiula, A. Sparta and S. Spampinato (2008). "New coumarin-based anti-inflammatory drug: putative antagonist of the integrins alphaLbeta2 and alphaMbeta2." *J Pharm Pharmacol* 60(11): 1473-1479.

Ding, Z., K. Xiong and T. B. Issekutz (2000). "Regulation of chemokine-induced transendothelial migration of T lymphocytes by endothelial activation: differential effects on naive and memory T cells." *J Leukoc Biol* 67(6): 825-833.

Gerli, R., P. Gresele, O. Bistoni, C. Paolucci, L. Lanfrancone, S. Fiorucci, C. Muscat and V. Costantini (2001). "Salicylates inhibit T cell adhesion on endothelium under nonstatic conditions: induction of L-selectin shedding by a tyrosine kinase-dependent mechanism." *J Immunol* 166(2): 832-840.

Mobley, J. L. and Y. Shimizu (2001). "Measurement of cellular adhesion under static conditions." *Curr Protoc Immunol* Chapter 7: Unit 7 28.

Rohnelt, R. K., G. Hoch, Y. Reiss and B. Engelhardt (1997). "Immunosurveillance modelled in vitro: naive and memory T cells spontaneously migrate across unstimulated microvascular endothelium." *Int Immunol* 9(3): 435-450.

Valignat, M. P., O. Theodoly, A. Gucciardi, N. Hogg and A. C. Lellouch (2013). "T lymphocytes orient against the direction of fluid flow during LFA-1-mediated migration." *Biophys J* 104(2): 322-331.

As exemplified in Table 1 herein, many target molecules both on leukocytes and endothelial cells as well as corresponding interfering compounds have been identified, are currently developed or have already been approved for use in humans. Therefore, it is envisaged to encompass in the present invention any existing or future compound regardless of its mode of action that demonstrates anti-adhesive effects on leukocytes, and more preferably T cells in the flow system as defined herein for the administration prior to, concurrently with and/or subsequently to the treatment of a patient with a therapy comprising re-directing of T cells against target cells e.g. through T cell transduction with a CAR or T cell recruitment via a compound comprising a CD3-specific binding domain, preferably Blinatumomab, for the prophylaxis or amelioration of CNS AEs caused by said (respective) therapy comprising re-directing of T cells against target cells.

Thus, in another embodiment the present invention relates to any compound that demonstrates anti-adhesive effects on leukocyte rolling and adhesion in the described flow system. Addition of said compound or any combination of such compounds to the flow system is expected to neutralize leukocyte adhesion induced by re-directing of T cells against target cells e.g. through T cell transduction with a CAR or T cell recruitment via a compound comprising a CD3-specific binding domain, preferably Blinatumomab-induced T cell-adhesion to blood vessel-lining endothelial cells, e.g. T cell-rolling velocity is reverted to levels comparable to those without Blinatumomab addition to the flow system. The present invention further relates to a combination of one or more of said compounds with the treatment of a patient with a therapy comprising re-directing of T cells against target cells e.g. through T cell transduction with a CAR or T cell recruitment via a compound comprising a CD3-specific binding domain prior to, concurrently with and/or subsequently to said treatment for the prophylaxis or amelioration of CNS AEs caused by said (respective) therapy comprising re-directing of T cells against target cells. In other words, any combinational treatment of (a) compound(s) with anti-adhesive properties and a therapy comprising re-directing of T cells against target cells e.g. through T cell transduction with a CAR or T cell recruitment via a compound comprising a CD3-specific binding domain is envisaged to be encompassed by the present invention. Yet in other words, it is envisaged as a requirement to administer any of said compounds or any combination thereof prior to, concurrently with and/or subsequently to the treatment of a patient with a therapy comprising re-directing of T cells against target cells e.g. through T cell transduction with a CAR or T cell recruitment via a compound comprising a CD3-specific binding domain for the prophylaxis or amelioration of CNS AEs caused by said (respective) therapy comprising re-directing of T cells against target cells.

In the context of the present invention, "anti-leukocyte adhesion" is defined as any prophylactic and/or interventional measure, method and/or procedure to prevent, minimize, reduce, influence, mitigate or modify leukocyte rolling on, binding to, adhesion to, transmigration through or interaction with endothelial cells, preferably blood vessel-lining endothelial cells. Additionally, compounds included in such measures, methods and/or procedures, or exerting any of the above listed effects on leukocytes are hereby defined as "compounds with anti-leukocyte adhesion effects" or "compounds with anti-adhesive properties" or "compounds of the invention" or "compound which decreases or inhibits the binding of mammalian T-cells to mammalian endothelial cells".

According to the current hypothesis leukocyte adhesion to blood vessel endothelium is a necessary prerequisite for the induction of severe adverse effects such as CNS AEs requiring treatment discontinuation. Thus, a possible mitigation approach for AEs, such as CNS AEs, is, in the context of the present invention, anti-leukocyte adhesion aiming at reducing endothelial adherence of re-directed T cells and optionally also other leukocytes (i.e. T lymphocytes, natural killer (NK) cells, neutrophil granulocytes and monocytes, which are the most prominent types of extravasating mammalian cells) following start of infusion and stepwise dose increases of the respective medicament, i.e. the therapy which comprises re-directing of T-cells against target cells in a patient, for example Blinatumomab, which therapy is the cause for endothelial cell-activation and leukocyte extravasation into the CNS (see the discussion herein and the results derived from the appended examples). The term "mammalian T-cells" comprises or consists of "re-directed T-cells", as these re-directed T-cells are causative for the AEs as explained herein. Thus, in a preferred embodiment of the present invention, said "mammalian T-cell" is a "re-directed mammalian T-cell". Re-directing of T cells comprises that T cells are equipped with an antigen receptor specificity recognizing a target cells which typically differs from the T cells' clonotypic natural antigen receptor specificity. This can e.g. be achieved by T cell engaging bi- or multi-functional antibodies or antibody derivatives which comprise a specific binding domain that is capable of specifically binding to a T-cell receptor, preferably to CD3. It is also possible (and explicitly envisaged within the context of the present invention) that such re-directed T-cells are produced by transduction of T cells with chimeric antigen receptors (CARs), for example CARs recognizing CD19 (see exemplarily Knochenderfer et al., Nature Reviews 2013; Clinical Oncology; "Treating B-cell cancer with T cells expressing anti-CD19 chimeric antigen receptors"). A "re-directed T-cell" thus includes T-cells that have been contacted with bi- or multi-functional antibodies or antibody derivatives which comprise a specific binding domain that is capable of specifically binding to a T-cell receptor (preferably to CD3) or a T-cell that has been genetically engineered to express a chimeric antigen receptor (i.e. a T-cell CAR—see WO2007/131092 which is included herein by reference).

In a particularly preferred embodiment said re-directed T-cell is a human T-cell that has been contacted with (is bound by) Blinatumomab (AMG103).

A "therapy which comprises re-directing of T-cells against target cells" is to be understood as a therapy, such as a medicament, which is characterized by the appearance and/or existence of "re-directed T-cells", i.e. the therapy either comprises or consists of re-directed T-cells as such, for example genetically engineered T-cell having a chimeric antigen receptor CAR (optionally formulated as a pharmaceutical composition) and/or the re-directed T-cells appear in the course of the therapy exemplified by a medicament which comprises a CD3-specific binding domain as defined herein, preferably a CD3-specific binding domain together with a binding domain which is specific for B-cells, more preferably a CD3-specific binding domain together with a binding domain which is specific for a CD-marker that can be found on B-cell lymphoma such as CD19, CD22, CD20 or CD79a, CD19 being preferred. In a more preferred embodiment, said therapy which comprises re-directing of T-cells against target cells is a therapy with a bispecific CD3 X CD19 antibody and in a most preferred embodiment said therapy which comprises re-directing of T-cells against target cells is a therapy with Blinatumomab.

It is also envisaged that said therapy with Blinatumomab encompasses the administration of 5 to 10 µg/m$^2$/day or higher doses, such as 15, 45 or 60 µg/m$^2$/day. The above mentioned CD-3 specific binding domains are explained in great detail herein elsewhere.

Chimeric antigen receptors (CARs) are fusion proteins comprising antigen recognition moieties and T cell-activation domains. For the treatment of B cell-malignancies, CD19 CARs consisting of a CD19-specific binding domain linked to, e.g. CD3zeta have been described in clinical studies for B CLL (Porter et al. N Engl J. Med. 2011; 365:725-33) and B ALL (Grupp et al. N Engl J. Med. 2013). As observed with the infusion of a CD19×CD3 bispecific single-chain antibody, adoptive transfer of CD19 CAR-transduced T cells into patients led to rapid and sustained eradication of normal and malignant B cells. Common adverse events associated with CD19 CAR T cell-therapy included cytokine release syndrome and lymphopenia, but cases of CNS AEs were also reported. Thus, interference with adhesion and transmigration of CD19 CAR T cells to/through blood vessel-lining endothelium also is a useful approach for the prophylaxis and/or amelioration of CD 19 CAR T cell-induced CNS AEs. Of note, it is envisaged that treatment with CAR T cells targeting other B cell-specific antigens (e.g. CD20) would also benefit from co-medication with compounds with anti-adhesive properties for the prophylaxis and/or amelioration of CNS AEs caused by such CAR T cells.

The "chimeric antigen receptor (CAR)" as used herein comprises a binding domain which is specific for B-cells, preferably specific for a CD-marker that can be found on B-cell lymphoma such as CD19, CD22, CD20 or CD79a, CD19 being preferred. T-cells that have been genetically engineered to express a chimeric antigen receptor CAR (a T-cell CAR) are exemplified in WO2007/131092. It is meanwhile known that also a therapy comprising T-cell CARs triggers clinical adverse events, and in particular CNS AE.

The term "target cells" is not specifically limited and relates preferably to cancer target cells (in particular cancer cells that express a suitable target which makes them attackable). B-lymphoma cells are more preferred, CD19 positive B-cells (B-lymphoma cells) being most preferred.

The term "mammalian" includes but is not limited to mouse, rat, dog, horse, camel, primates, etc., primates being preferred and human beings being most preferred.

The mammalian "endothelial cells" can be isolated from large vessels or capillaries. The term "endothelial cells" thereby includes freshly isolated endothelial cells (for example HUVECs), commercially available endothelial cells from different manufacturers (e.g. PromoCell) and endothelial cell lines, although endothelial cell lines are less preferred. Human endothelial cells are preferred. Human Umbilical Vein Endothelial Cells (HUVEC) and Human Brain Microvascular Endothelial Cells (HBMEC) are particularly preferred, HBMECs being most preferred.

Adverse events can be classified in five grades in accordance with the Common Terminology Criteria for Adverse Events (CTCAE). Grade 1 relates to mild AEs, Grade 2 to moderate AEs, Grade 3 to severe AEs, Grade 4 to life-threatening or disabling AEs, while Grade 5 means death related to AEs. All these AEs are contemplated within the framework of the present invention and included by the term "clinical adverse events" or "adverse effects" or related terms used herein.

The term "clinical adverse events" used herein caused by therapy which comprises re-directing of T-cells against target cells in a patient comprises in particular neurological adverse events. Said neurological adverse event, which sometimes is also denoted as "neurological symptom" or "neurological adverse effect" or "central nervous system adverse event (CNS AE)", includes but is not limited to conditions of a human patient such as all forms of pain, headache, muscle weakness/incoordination, balance disorder, speech disorder/impairment, sensual disturbance/abnormalities, dizziness, ataxia, apraxia, tremor, aphasia, dysphasia, confusion, disorientation, hallucination, cerebellar symptoms, encephalopathy, seizure, (grand mal) convulsion. Specifically, neurological symptoms observed during treatment with a therapy comprising re-directing of T cells against target cells e.g. through T cell transduction with a CAR or T cell recruitment via a compound comprising a CD3-specific binding domain include for example confusion and disorientation. "Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological symptoms also suffer from loss of memory. Frequently, confusion leads to loss of the ability to recognize people and/or places, or to tell time and date. Feelings of disorientation are common in confusion, and the decision-making ability is impaired. Neurological symptoms further comprise blurred speech and/or word-finding difficulties. This disorder may impair the expression and understanding of language as well as reading and writing. Additionally, vertigo and dizziness may accompany neurological symptoms in some patients.

The term "clinical adverse events" is preferably characterized by (but not limited to) one or more of (i) cognitive disorder comprising disorientation/confusion and/or word finding problems/aphasia, (ii) seizure, (iii) cerebellar symptoms partly observed as an optional prodromal phase of (i) or (ii) comprising kinetic tremor, ataxia, dysarthria and handwriting problems. Further neurological adverse event are apraxia and hallucination. Word finding problems are preferred in the context of the present invention. Of particular clinical significance are clinical adverse effects which cause discontinuation of treatment with therapy which comprises re-directing of T-cells against target cells in a patient (preferably therapy with Blinatumomab or other CD3-binding drugs or CARs), because the treated patient thus cannot fully benefit from the treatment.

The "patient" is a mammalian patient, preferably a primate, most preferably a human being.

In a preferred embodiment the patient is suspected/assumed to comprise or already comprises malignant CD19-positive B cells. In the latter case said patient has already been diagnosed to comprise such cells. The malignant CD19-positive B cells are present in a patient developing and/or suffering from lymphoma and/or leukemia.

The present invention also relates to a nucleic acid which encodes a chimeric antigen receptor (CAR) for use in a method of re-directing of T-cells against target cells in a patient, wherein said patient is subject to therapy comprising the "compound which decreases or inhibits the binding of mammalian T-cells to mammalian endothelial cells". A nucleic acid sequence thereby includes, although not being limited thereto, vectors etc., which will allow the expression of the desired CARs in T-cells (see for example WO2007/131092 which is included herein by reference).

For the avoidance of any doubt, it is hereby stressed that the disclosure of the present invention including all definitions etc. is fully applicable to all embodiments that form part of the present invention (i.e. are linked with the gist of the invention and therefore fall into the context of the present invention), irrespective of whether these embodiments are drafted as compounds for use embodiments or method of treatment embodiments or compound embodiments, kit embodiments, composition embodiments, use embodiments, method embodiments etc. Thus, all definitions and embodiments can be used and apply to all embodiments disclosed herein. The present invention thus also relates to a method for prophylaxis, amelioration and/or treatment of clinical adverse events caused by therapy which comprises re-directing of T-cells against target cells in a patient, said method comprising administering a therapeutically effective amount of a compound which decreases or inhibits the binding of mammalian T-cells to mammalian endothelial cells. The term "therapeutically effective amount" is meant to refer to an amount of the compound which decreases or inhibits the binding of mammalian T-cells to mammalian endothelial cells that provides a treatment, amelioration or prophylaxis of clinical adverse events caused by therapy which comprises re-directing of T-cells against target cells in a patient (i.e. that provides "therapeutic efficacy").

In the following it is intended to further illustrate the etiology of central nervous system adverse events (CNS AEs) caused by a CD3-specific binding domain and the rationale for employing anti-leukocyte adhesion as prophylaxis and amelioration of such CNS AEs.

CNS AEs requiring treatment discontinuation are currently best explained by the hypothesis of a multi-step pathomechanism initiating transient meningeal or perivascular neuroinflammation.

Start of infusion with Blinatumomab and any stepwise dose increase induce rapid adhesion of peripheral blood T cells, along with other peripheral blood leukocytes such as NK cells and monocytes, to blood vessel-lining endothelial cells. This process occurs irrespective of the presence of circulating (i.e. peripheral blood) target cells, i.e. normal and/or malignant CD19-positive B cells. Moreover, T cell-redistribution as a result of T cell-adhesion to blood vessel endothelium seems to be at least partially independent of the Blinatumomab dose as it was observed even at the lowest dose level of 0.5 μg/m²/day tested. Accordingly, T cell-redistribution as a result of a transient increase in T cell-adhesiveness appears to be triggered by the exposure change per se at start of Blinatumomab administration and during dose increases rather than by the higher absolute exposure at a higher dose. The endothelial adhesion of peripheral blood leukocytes is very likely to also take place at blood vessels of the CNS where especially meningeal microvessels have been suggested as initial entry site for inflammatory cells from peripheral blood and as a potential starting point for neuroinflammatory phenomena.

As described in more detail in herein, three key findings support this assumption: (1) the redistribution of circulating T cells and other leukocytes after start of infusion or stepwise dose increase in any patient involving a rapid decrease of blood cell-counts already within 45 minutes followed by a recovery of blood cell-counts within a few days; (2) the transient increase of adhesiveness of circulating T cells to blood vessel-lining endothelial cells as measured by increased binding of soluble ICAM-1-$F_c$ fusion proteins to LFA-1 on T cells; and (3) the transient increase of angiopoietin-2 (Ang-2) in peripheral blood, which represents a specific marker for the activation of endothelial cells (Fiedler and Augustin. *Trends Immunol.* 2006; 27:552-8).

Following adhesion of leukocytes to meningeal microvessels and postcapillary brain venules, part of these cells are thought to extravasate into leptomeningeal and perivascular spaces, respectively (FIGS. 2A and B). Even in the absence of profound T cell-extravasation, leukocyte adhesion to blood vessel-lining endothelial cells per se may induce leakage of CNS blood vessels and neurological symptoms such as seizures (Fabene et al. *Nat. Med.* 2008; 14:1377-83).

Pentosanpolysulfate (PPS; $C_{14}H_{26}O_{21}S_4$), also known as Pentosan Polysulphate, Xylan Hydrogen Sulfate, Xylan Polysulfate, is a semi-synthetically produced heparin-like macromolecular carbohydrate derivative, which chemically and structurally resembles glucosaminoglycans. It is a white odorless powder, slightly hygroscopic and soluble in water to 50% at pH 6. It has a molecular weight of 4000 to 6000 Dalton.

PPS is, for example, sold under the name Elmiron® by Ortho-McNeil Pharmaceutical, Inc. and is thus far the only oral medication approved by the U.S. FDA for the treatment of interstitial cystitis, also known as painful bladder syndrome. For treatment of this condition, PPS is administered orally, however, it can alternatively be administered intravenously.

The term "pentosanpolysulfate (or PPS)" encompasses semi-synthetically produced heparin-like macromolecular carbohydrate derivatives.

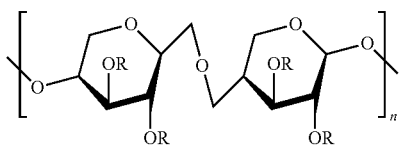

In the sense of the present invention, pentosanpolysulfate is a mixture of linear polymers of β1→4-linked xylose, usually sulfated at the 2- and 3-positions and occasionally substituted at the 2-position with 4-O-methyl-α-D-glucuronic acid-2,3-O-sulfate. Accordingly, PPS may also be designated as β1→4-D-Xylan-2,3-bis(hydrogen sulfate).

By way of example, a semi-synthetically produced heparin-like macromolecular carbohydrate derivative such as in particular PPS is, for example, producible (obtainable) as follows: its polysaccharide backbone, xylan is, for example, extracted from the bark of the beech tree or other plant sources and is then treated with sulfating agents such as chlorosulfonic acid or sulfuryl chloride and acid. After sulfation, PPS is usually treated with sodium hydroxide to yield the sodium salt which is a preferred salt of the present invention. Processes for the production of a semi-synthetically produced heparin-like macromolecular carbohydrate derivative such as in particular PPS are, for example, disclosed in U.S. Pat. No. 2,689,848 or US 2010/0105889.

In the context of the present invention PPS is preferably administered orally to a patient, even more preferably intravenously. Typical doses are 100, 150, 200 or 300 mg, administered 1-3 times per day, with a maximum amount of 600 mg/day. Typically, the daily dose is between 100 and 600 mg such as 100, 150, 200, 250, 300, 350, 400, 450, 500, 550 or 600 mg or even more. For example, 100 mg PPS may be administered 3-6 times. Similarly, 200 mg PPS may be administered 2-3 times. Alternatively, 300 mg PPS may be administered 2 times. Alternatively, PPS in an amount, for example, between 100 and 600 mg such as 100, 150, 200, 250, 300, 350, 400, 450, 500, 550 or 600 mg may be administered over 24 hours via infusion, for example, by using a perfusor. In the latter case, a bolus injection of PPS in an amount, for example, of 100, 200 or 300 mg may precede a therapy comprising re-directing of T cells against target cells in a patient, followed by administration of PPS of 100, 200 or 300 mg/day over 24, 48 or 72 hours.

PPS may be administered prior to (e.g. prophylactically as a bolus injection), concurrently with or subsequently to the administration of a therapy comprising re-directing of T cells against target cells in a patient as described herein. Advantageously, PPS may be administered to a patient when the therapy comprising re-directing of T cells against target cells in a patient will be repeated or increased (e.g. at start of infusion or any dose steps). A particular preferred PPS that was administered to a patient mentioned in the present invention is pentosanpolysulfate SP54® commonly known and available in the market (e.g. from bene Arzneimittel GmbH).

Apart from PPS, other clinically available compounds with known anti-adhesive properties are Minocycline and Natalizumab as described herein. While P-selectin mediates the first step (i.e. rolling) of leukocyte adhesion to endothelial cells, the subsequent steps are integrin-mediated. Particularly, the interactions of LFA-1 and VLA-4 on T cells with ICAM-1 and VCAM-1 on endothelial cells, respectively, play a prominent role during this second phase of leukocyte adhesion to endothelial cells. As such, since LFA-1, VLA-4 and ICAM-1 belong to the family of integrins and IgG superfamily, integrin antagonists and IgG superfamily antagonists are preferred compounds of the present invention.

As small-molecule inhibitors of LFA-1, tetracyclines are available for clinical use in humans. Within the tetracycline family, Minocycline is the best-characterized inhibitor of LFA-1 (Nikodemova et al. *J Neuroimmunol.* 2010; 219:33-7). Minocycline is the most lipophilic among all tetracyclines and has an almost 100% bioavailability after oral administration. It also has the longest in vivo half-life of approximately 24 hours which is the prerequisite for an uninterrupted serum exposure over a prolonged period of time. Moreover, Minocycline penetrates best into the CNS which makes it particularly suitable for the treatment of CNS disorders. In clinical trials, Minocycline was shown to counteract neuroinflammation in multiple sclerosis (Zhang et al. *Can J Neurol Sci.* 2008; 35:185-91) and to improve the neurological outcome in patients with acute ischemic stroke (Lampl et al. *Neurology.* 2007; 69:1404-10). In a recent dose-finding study on Minocycline as neuroprotective agent in stroke patients, daily doses of up to 10 mg/kg iv equivalent to 700 mg per os for several days were found to be safe and well-tolerated (Fagan et al. *Stroke.* 2010; 41:2283-7). Mechanistically, Minocycline both down-regulates expression of LFA-1 on T cells and acts as a chelator for cations such as $Ca^{2+}$ and $Mg^{2+}$ which are required for firm binding of LFA-1 to ICAM-1. Thus, as said above, Minocyclin is a preferred compound of the present invention.

Natalizumab is an antibody approved for the treatment of multiple sclerosis. It binds to VLA-4 on T cells thereby blocking its interaction with VCAM-1 on endothelial cells. In consequence, T cell-adhesion and extravasation, especially into the brain, are diminished. Hence, Natalizumab is another preferred compound of the present invention.

A non-exclusive list of other compounds with proposed anti-adhesive properties that are or might become available for clinical use in humans is provided in Table 1. Each of these compounds is a preferred compound of the present invention, with Minocyclin and Natalizumab being more preferred.

In connection with the present invention a "CD3-specific binding domain" sometimes also denoted herein as "CD3 binding domain" characterizes a binding domain which comprises a framework/framework region and an "antigen-binding site" or an "antigen-interaction site" which is able to specifically interact with a CD3 antigen. Said binding/interaction is also understood to define a "specific recognition". The term "specifically interact/interacting" means in accordance with this invention that the binding domain is capable of binding to an epitope of the CD3 antigen, preferably the CD3epsilon antigen, and more preferably the human CD3epsilon antigen.

As used herein, "CD3" denotes a molecule expressed as part of the T cell-receptor complex and has the meaning as typically ascribed to it in the prior art. In humans, it encompasses in individual or independently combined form all known CD3 subunits, for example CD3epsilon, CD3delta, CD3gamma and CD3zeta. The human CD3epsilon antigen is indicated in GenBank Accession No. NM_000733.

The term "framework (region)" includes a scaffold for antigen-binding sites. For example, such a scaffold could be provided by protein A, in particular the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain or thioredoxin (Skerra. *Curr Opin Biotechnol.* 2007; 18:295-304; Hosse et al. *Protein Sci.* 2006; 15:14-27; Nicaise et al. *Protein Sci.* 2004; 13:1882-91; Nygren and Uhlén. *Curr Opin Struct Biol.* 1997; 7:463-9).

In the context of the present invention a preferred framework is the art-recognized portions of an antibody variable region that exist between the more divergent (i.e. hypervariable) complementarity determining regions (CDRs) within the variable region of an antibody. Such framework regions are typically referred to as frameworks 1 through 4 (FR1, FR2, FR3, and FR4) and provide scaffolds for the presentation of the six CDRs (three from the heavy chain and three from the light chain) in three dimensional space, to form an antigen-binding surface.

A preferred example of a CD3-specific binding domain in line with the present invention is an antibody. The CD3-specific binding domain may be a monoclonal or polyclonal antibody or derived from a monoclonal or polyclonal antibody. The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual", Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2, etc.). The definition of the term "antibody" also includes embodiments such as chimeric, single-chain, de-immunized and humanized antibodies, as well as antibody fragments, like, inter alia, Fab fragments. Antibody fragments or derivatives further comprise F(ab')$_2$, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

Bispecific antibody formats are preferred; however, other multispecific antibody formats (trispecific, tetrabodies, etc.) are not excluded. It is preferred that said CD3 binding domain is contained in or is comprised by a bispecific single chain antibody. Said bispecific single chain antibody further comprises in another preferred embodiment of the present invention a binding domain which is specific for B-cells, preferably specific for a CD-marker that can be found on B-cell lymphoma such as CD19, CD22, CD20 or CD79a, CD19 being preferred. In a particularly preferred embodiment, said bispecific single chain antibody is a CD19×CD3 or CD20×CD3 bispecific single chain antibody. In an even more preferred embodiment, said CD19×CD3 bispecific single chain antibody is Blinatumomab (MT103/AMG103). In a further preferred embodiment of the present invention said CD19×CD3 bispecific single-chain antibodies comprise a first binding domain capable of binding to an epitope of human CD3epsilon and a second binding domain capable of binding to human CD 19. The human CD-Antigens are easily derivable from publicly available databases. The human CD19 antigen is for example indicated in GenBank Accession No. AAA69966.

All the specific CD19×CD3 bispecific single-chain antibodies disclosed therein, including their variants, fragments, equivalents, etc. are particularly preferred CD19×CD3 bispecific single-chain antibodies of the present invention.

As used herein, a "CD19×CD3 bispecific single-chain antibody" denotes a single polypeptide chain comprising two binding domains. Such bispecific single-chain antibodies are preferred in the context of the methods/dosage regimen of the present invention. Each binding domain comprises at least one variable region from an antibody heavy chain ("VH or H region"), wherein the VH region of the first binding domain specifically binds to CD3epsilon and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B 1, but in any case long enough to allow the VH region and VL region of the first binding domain and the VH region and VL region of the second binding domain to pair with one another such that, together, they are able to specifically bind to the respective first and second binding domain. Such CD19×CD3 bispecific single-chain antibodies are described in great detail in WO 99/54440 and WO 2004/106381.

Preferably, the bispecific single-chain antibody applied in the methods/dosage regimen of the present invention has the domain arrangement (a) VL(CD19)-VH(CD19)-VH (CD3)-VL(CD3). However, it is also envisaged that the methods of the invention can be carried out with CD19×CD3 bispecific single-chain antibodies of other domain arrangements, such as (b) VH(CD19)-VL(CD19)-VH(CD3)-VL(CD3),
(c) VL(CD19)-VH(CD19)-VL(CD3)-VH(CD3),
(d) VH(CD19)-VL(CD19)-VL(CD3)-VH(CD3),
(e) VL(CD3)-VH(CD3)-VH(CD19)-VL(CD19),
(f) VH(CD3)-VL(CD3)-VH(CD19)-VL(CD19),
(g) VL(CD3)-VH(CD3)-VL(CD19)-VH(CD19), or
(h) VH(CD3)-VL(CD3)-VL(CD19)-VH(CD19).

A preferred CD19×CD3 bispecific single-chain antibody applied in the methods of the present invention comprises the (a) anti-CD3 CDRs of the heavy chain shown as CD3 CDR-H1 in SEQ ID NO: 11 (RYTMH), more preferably in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or (b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
(c) anti-CD19 CDRs of the heavy chain shown as CD19 CDR-H1 in SEQ ID NO: 17 (SYWMN), more preferably in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTT-VGRYYYAMDY); and/or
(d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19×CD3 bispecific single-chain antibody applied in the methods of the present invention comprises the CD3 CDRs of the heavy and light chain. Even more preferably, the CD19×CD3 bispecific single-chain antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues of an antibody in a consistent manner (Kabat et al., Sequences of Proteins of Immunological Interest, 1991).

Alternatively, it is preferred that the CD19×CD3 bispecific single-chain antibody applied in the methods of the present invention comprises the
(a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19×CD3 bispecific single-chain antibody applied in the methods of the present invention comprises the CD19 variable heavy and light chain and/or the CD3 variable heavy and light chain. Even more preferably, the CD19×CD3 bispecific single-chain antibody applied in the methods of the present invention comprises the CD19 variable heavy and light chain as well as the CD3 variable heavy and light chain.

In another alternative, it is also preferred that the CD19×CD3 bispecific single-chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD 19; and
(d) an amino acid sequence encoded by a nucleic acid sequence which is degenerate as a result of the genetic code to a nucleotide sequence of (b), wherein said amino acid sequence is capable of specifically binding to CD3 and CD 19.

It is to be understood that the sequence identity is determined over the entire amino acid sequence. For sequence alignments, for example, the programs Gap or BestFit can be used (Needleman and Wunsch. *J Mol Biol.* 1970; 48:443-53; Smith and Waterman. *Adv Appl Math.* 1981; 2:482-9), which are contained in the GCG software package (Genetics Computer Group, 575 Science Drive, Madison, Wis., USA 53711). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific single-chain antibodies described herein (preferably Blinatumomab). For example, according to Crick's Wobble hypothesis, the 5' base on the anti-codon is not as spatially confined as the other two bases, and could thus have non-standard base pairing. In other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick. *J Mol. Biol.* 1966; 19:548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19×CD3 bispecific single-chain antibodies described herein. Cytotoxic activity of the CD19×CD3 bispecific single-chain antibody or an antibody construct having e.g. 70%, 80%, 90%, 95%, 96%, 97%, 98% or 99% sequence identity to the amino acid sequences of the CD19×CD3 bispecific single-chain antibodies described herein can be determined by methods as illustrated, e.g. in WO 99/54440.

It is particularly preferred, that said CD19×CD3 bispecific single-chain antibody has the amino acid sequence shown in SEQ ID NO: 1. Also particularly preferred is the CD19×CD3 bispecific single-chain antibody as described in WO 99/54440 as well as those CD19×CD3 bispecific single-chain antibodies described in WO 2004/106381. Blinatumomab (or AMG 103 or MT103) is most preferred.

The present invention further relates to a CD19×CD3 bispecific single-chain antibody and/or a method for
(a) treating malignant CD19-positive cells, preferably lymphocytes, even more preferably B cells, in a human patient, and/or
(b) administering a CD19×CD3 bispecific single-chain antibody to a human patient;
wherein a compound with anti-adhesive properties is to be administered prior to, concurrently with or subsequently to the treatment of a human patient with said CD19×CD3 bispecific single-chain antibody for the prophylaxis or amelioration of CNS AEs caused by said CD19×CD3 bispecific single-chain antibody.

a compound which decreases or inhibits the binding of mammalian T-cells to mammalian endothelial cells for use in a method of prophylaxis and/or amelioration and/or treatment of clinical adverse events caused by therapy which comprises re-directing of T-cells against target cells in a patient The administration of the therapy which comprises re-directing of T-cells against target cells in a patient (preferably the CD3-specific binding domain, more preferably Blinatumomab), of (a) compound(s) with anti-adhesive properties (compound which decreases or inhibits the binding of mammalian T-cells to mammalian endothelial cells) and/or of (a) pharmaceutical composition(s) comprising either or a combination of the aforementioned components, is preferably an intravenous administration. It may be administered as a bolus injection or by continuous (continual) intravenous (civ) infusion, with continuously being preferred. A continuous administration refers to an administration which essentially is without interruption. "Essentially without interruption" includes a continuous administration which usually is without interrupted flow or spatial extension. By way of example, WO 2007/068354 discloses a treatment regimen which is specifically included herein by way of reference thereto. Other treatment regimens which are envisaged in the context of the present invention are disclosed in PCT/EP2010/066207.

It is also envisaged that the patient is characterized by a B/T-cell ratio of less than 1:5 (see PCT/EP2010/066207) and/or a B-cell number of less than about 50 B-cells per µl peripheral blood. As disclosed in great detail in PCT/EP2010/066207, the administration of a CD3-specific binding domain, in particular of a CD19×CD3 bispecific single-chain antibody to a patient is frequently accompanied by neurological symptoms if said patient is characterized by a B:T cell-ratio of less than 1:5. However, the herein disclosed prophylaxis or amelioration of these neurological adverse effects caused by a CD3-specific binding domain by way of co-medication with (a) compound(s) having anti-adhesive properties (as defined in the present invention) is also applicable to patients who are characterized by a B:T cell-ratio equal to or of more than 1:5 (see PCT/EP2010/066207).

The present invention also relates to a (pharmaceutical) kit or package comprising a "compound" (i.e. a compound which decreases or inhibits the binding of mammalian T-cells to mammalian endothelial cells as defined herein) and/or a "therapy which comprises re-directing of T-cells against target cells" (also defined herein, preferably a CD3-specific binding domain and most preferred Blinatumomab), and instructions, a label and/or an imprint indicating that said compound is to be employed for use in a method of prophylaxis and/or amelioration and/or treatment of clinical adverse events caused by therapy which comprises re-directing of T-cells against target cells in a patient. Additionally or alternatively, said instructions, label and/or imprint indicate that a therapy which comprises re-directing of T-cells against target cells, may cause AEs, in particular CNS AEs and that it is therefore recommended, envisaged or necessary to mitigate these effects with a compound which decreases or inhibits the binding of mammalian T-cells to mammalian endothelial cells. The compounds and/or the therapy which comprises re-directing of T-cells against target cells, is/are preferably packaged in one sealed kit or package. It is also envisaged that this kit or package further comprises means to administer the content(s) to a patient, and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person to prepare the respective doses and infusions of the invention, etc.

The above mentioned (pharmaceutical) kit or package may also comprise a nucleic acid which encodes a chimeric antigen receptor (CAR).

Tables

TABLE 1

Compounds with known or proposed anti-adhesive properties that are or might become available for clinical use in humans.

| Target | Compound | Mode of Action | Reference |
| --- | --- | --- | --- |
| Endothelial cell adhesion molecules (also denoted as targets on endothelial cells) | | | |
| P-selectin | PPS, small molecule | Blockage of PSGL-1 binding site | Höpfner et al. *J Pharm Pharmacol.* 2003; 55: 697-706 |
| | Inclacumab, mAb | Blockage of PSGL-1 binding site | Kling et al. *Thromb Res.* 2013 |
| ICAM-1 | Alicaforsen enema (ISIS2303), siRNA | Inhibition of ICAM-1 expression | Van Deventer et al. *Aliment Pharmacol Ther.* 2006; 23: 1415-25 |
| MAdCAM | PF-00547659, mAb | Blockage of β7-integrins binding site | Pullen et al. *Br J Pharmacol.* 2009; 157: 281-93 |
| VCAM-1 | Rosuvastatin, small molecule | Reduction of VCAM-1 expression | Osaka et al. *Biomed Res Int.* 2013 |
| PAR-1, fibrinogen | Thrombin (at low pM concentrations) | Anti-leukocyte adhesive effect, maintenance of vascular barrier integrity | Ku and Bae. *Inflamm Res.* 2013 |
| T-cell adhesion molecules (also denoted as targets on T cells) | | | |
| $\alpha_4$-integrins (e.g. VLA-4, LPAM-1) | Natalizumab, mAb | Blockage of VCAM-1, MAdCAM, fibrinogen, chondroitin binding site | Haanstra et al. *J Immunol.* 2013 |
| | AJM300, small molecule | Blockage of ligand binding site | Thomas and Baumgart. *Inflammopharmacology.* 2012; 20: 1-18 |

TABLE 1-continued

Compounds with known or proposed anti-adhesive properties that are or might become available for clinical use in humans.

| Target | Compound | Mode of Action | Reference |
|---|---|---|---|
| $\alpha_L\beta_2$-integrin (LFA-1) | Minocycline | Reduction of LFA-1 expression, ion chelator | Nikodemova et al. *J Neuroimmunol.* 2010; 219: 33-7 |
| | SAR 1118, small molecule | Blockage of ICAM-1, -2, -3 binding site | Rao et al. *Invest Ophthalmol Vis Sci.* 2010; 51: 5198-204 |
| | BOL-303225-A, small molecule | Antagonist | Bucolo et al. *J Pharm Pharmacol.* 2008; 60: 1473-9 |
| $\alpha_L$-integrins (e.g. LFA-1) | Efalizumab, mAb | Blockage of ICAM-1 binding site | Koszik et al. *J Dermatol Sci.* 2010; 60: 159-66 |
| $\beta_7$-integrins | Etrolizumab, mAb | Blockage of VCAM-1 and MAdCAM binding site | Stefanich et al. *Br J Pharmacol.* 2011; 162: 1855-70 |
| $\alpha_5\beta_1$-integrin (VLA-5) | Natramune (PDS-2865), PureWay-C, ascorbic acid; small molecule | Interference with $\alpha_5\beta_1$-integrin-mediated adhesion | Weeks et al. *Med Sci Monit.* 2008; 14: BR279-85; Eylar et al. *P R Health Sci J.* 1996; 15: 21-6 |
| L-selectin | (Acetyl-) salicylic acid | Reduction of L-selectin expression | Gerli et al. *J Immunol.* 2001; 166: 832-40 |
| Integrins (e.g. LFA-1, VLA-4) | Ethylenediaminetetra-acetic acid (EDTA) | Ion chelator | Welzenbach et al. *J Biol Chem.* 2002; 277: 10590-8 |
| CD44 | Hyaluronic acid (HA), chondroitin Sulfate, anti-CD44 mAb | Blockage of HA and E-selectin binding site | Murai et al. *Immunol Lett.* 2004; 93: 163-70; Baaten et al. *Front Immunol.* 2012; 3: 23 |
| | Astilbin, flavonoid | Reduction of CD44 expression | Yi et al. *Int Immunopharmacol.* 2008; 8: 1467-74 |
| CD162 (PSGL-1) | mAb | Blockage of P-selectin binding site | Moore. *Leuk Lymphoma.* 1998; 29: 1-15 |
| Src-family kinases (e.g. Lck, Fyn) | PP2 (4-Amino-5-(4-chlorophenyl)-7-(t-butyl)pyrazolo[3,4-d]pyrimidine) | Selective inhibitor of Src-family kinases | Feigelson et al. *J Biol Chem.* 2001; 276: 13891-901 |
| Targets on T cells and/or endothelial cells | | | |
| Sialidase | Sialidase inhibitors, e.g. castanospermine; small molecule | Blockage of desialylation of, e.g. LFA-1, ICAM-1 | Feng et al. *J Leukoc Biol.* 2011; 90: 313-21 |
| Adhesion molecules | Recombinant ligands of respective adhesion molecules | Competitive blockage of natural ligand binding | |
| | siRNA, shRNA | Reduction or inhibition of expression of respective adhesion molecules | | mAb: monoclonal antibody

TABLE 2

Characteristics of freshly isolated human T cells.

| Marker | CD3 | CD4 | CD8 | CD11a | CD49d | CD162 | CD69 | CD25 | HLA-DR |
|---|---|---|---|---|---|---|---|---|---|
| % positive cells ± SD | 93.37 ± 9.41 | 68.87 ± 4.02 | 25.10 ± 4.50 | 99.93 ± 0.06 | 32.90 ± 2.04 | 99.87 ± 0.23 | 1.10 ± 0.52 | 49.60 ± 13.85 | 5.03 ± 2.15 |

The expression of CD3, CD4, CD8, CD11a, CD49d, CD162 (PSGL-1), CD69, CD25, and HLA-DR on the surface of freshly isolated human T cells was determined by flow cytometry. CD3-positive cells are expressed as mean percentage±SD of all events of 3 independent measurements. CD4, CD8, CD11a, CD49d, CD162, CD69, CD25, and HLA-DR-positive cells are expressed as mean percentages±SD of CD3-positive cells of 3 independent measurements.

The compound of the present invention is preferably a non-glucocorticoidal compound, i.e. glucocorticoids are preferably excluded. The term "glucocorticoid" means compounds that bind, preferably specifically, to the glucocorticoid receptor. Said term includes compound(s) selected from the group consisting of cortisone, cortisol (hydrocortisone), cloprednol, prednisone, prednisolone, methylprednisolone, deflazacort, fluocortolone, triamcinolone, dexamethasone, beatamethasone, cortivazol, paramethasone, and/or fluticasone, including pharmaceutically acceptable derivatives thereof.

EXAMPLES

The following examples illustrate the invention. These examples should not be construed as to limit the scope of this invention. The examples are included for purposes of illustration.

Example 1

Successful Mitigation of CNS AEs by Anti-leukocyte Adhesion with PPS in Patients at High Risk of Discontinuation of Blinatumomab Treatment Due to CNS AEs Dosing Regimen of Blinatumomab and PPS Co-medication.

In a phase 1 clinical study three patients were treated with Blinatumomab at an initial dose of 5 μg/m$^2$/day for 1 week followed by a dose escalation to 60 μg/m$^2$/day for additional 3 to 7 weeks. Concomitant PPS was administered as 100 mg bolus iv infusion at 3 h±30 min prior to start of infusion and dose escalation of Blinatumomab followed by perfusion of 300 mg/day for 48 h after start of infusion and dose escalation of Blinatumomab.

Patient 109-036 (See Also FIG. 3E).

Patient 109-036, a male Caucasian, age 62, weight 96.8 kg, height 178 cm, presented with Follicular Lymphoma grade I/II. Previous therapies included CHOP (02/12-03/04), Dexa BEAM (03/05), Cyclophosphamid (03/08), and radio therapy followed by autologous stem cell transplantation (03/08). The patient achieved a complete response (CR) after 57 days of civ infusion of Blinatumomab. Although this patient had a high risk of developing CNS AEs due to his low B:T cell-ratio (see PCT/EP2010/066207), no treatment discontinuation due to CNS AEs was required.

Patient 109-040 (See Also FIG. 3F).

Patient 109-040, a male Caucasian, age 51, weight 94.0 kg, height 180 cm, presented with Lymphoplasmocytic Lymphoma (Morbus Waldenström). Previous therapies included CVP (04/12-05/03), Leukeran (05/10-05/12), Rituximab (06/05-06/07), R-CHOP (06/07-06/10), Dexa BEAM (06/10), BEAM (06/12), and radio therapy followed by autologous stem cell transplantation (06/12). Additional prior therapies comprised Rituximab+Bendamustine (09/04-09/12) and Rituximab (09/04-09/12). The patient achieved a stable disease (SD) after 30 days of civ infusion of Blinatumomab. Although this patient had a high risk of developing CNS AEs due to his low B:T cell-ratio (see PCT/EP2010/066207), no treatment discontinuation due to CNS AEs was required.

Patient 109-042 (See Also FIG. 3D).

Patient 109-042, a female Caucasian, age 49, weight 92.0 kg, height 169 cm, presented with Follicular Lymphoma grade I/II. Previous therapies included R-CHOP (09/11-10/02) and Rituximab (10/03-10/04). The patient achieved a complete response (CR) after 56 days of civ infusion of Blinatumomab. Although this patient had a high risk of developing CNS AEs due to her low B:T cell-ratio (see PCT/EP2010/066207), no treatment discontinuation due to CNS AEs was required.

Example 2

In Vitro Flow Chamber System Mimicking T Cell/endothelial Cell-Interaction Triggered by Blinatumomab or Other CD3-Specific Binding Drugs Cultivation of Endothelial Cells.

Human brain microvascular endothelial cells (HBMEC) (#1000, Sciencell Research Laboratories) or human umbilical vein endothelial cells (HUVEC) (#C-12200, Promocell) were used as endothelial cell-model. Cryopreserved HBMEC at passage 1 (>5×10$^5$ cells/ml) were first cultivated in fibronectin-coated Nunclon-treated 75 cm$^2$ cell culture flasks (#156499, Nunc) at 37° C. and 5% CO$_2$ in a Heraeus Cytoperm 2 (Thermo Scientific) according to the manufacturer's instructions. Sub-cultivation of HBMEC was done with the Detach Kit (#C-41200, Promocell) consisting of HEPES-buffered balanced salt solution (#C-40000, Promocell), trypsin-EDTA solution (0.04%/0.03%) (#C-41000, Promocell) and trypsin neutralization solution (TNS, #C-41100, Promocell). Briefly, the medium was aspirated from the HBMEC-layer and cells were washed with 2 ml of HEPES-buffered balanced salt solution. Addition of 2 ml of trypsin-EDTA solution for 1-5 min at room temperature led to detachment of HBMEC from the flask bottom. Inactivation of trypsin-EDTA solution was performed by addition of 2 ml of trypsin neutralization solution to the cell suspension. Cells were centrifuged at 300 g for 4 min in a Heraeus Megafuge 40 (Thermo Scientific) and seeded at a cell density of 5×10$^5$ cells per gelatin-coated 75 cm$^2$ cell culture flask (#L7230, Biochrom). HBMEC for rolling and adhesion experiments were cultivated in RPMI 1640 medium (#FG1215, Biochrom) supplemented with Nu-Serum IV (10%) (#355505, BD Biosciences), dialyzed FBS (10%) (#SZ0115, Biochrom), MEM-vitamins (1%) (#K0373, Biochrom), L-glutamine (1%) (#K0283, Biochrom), sodium-pyruvate (1%) (#L0473, Biochrom), heparin (10 U/ml) (#L6510, Biochrom), and epidermal cell growth factor ECGS (30 μg/ml) (#02-102, Millipore). Cultivation of HUVEC was done in endothelial cell growth medium (#C-22010, Promocell) supplemented with dialyzed FBS (10%) (#SZ0115, Biochrom) using gelatin-coated 75 cm$^2$ cell culture flasks. Sub-cultivation of HUVEC was performed with the Detach Kit (#C-40000, Promocell) and cells were seeded at a cell density of 4.0-7.5×10$^5$ cells per 75 cm$^2$ cell culture flask.

Isolation of Human Peripheral Blood Mononuclear Cells (PBMC) and T Cells from Blood.

Isolation of human PBMC from blood was performed by modified density gradient centrifugation as described elsewhere. Briefly, 15-20 ml of freshly drawn heparinized blood was transferred in Biocoll (#L6115, Biochrom)-containing Leukosep tubes (#227290, Greiner bio-one) and centrifuged in a Hettich Rotanta 460 RS Type 5606 (Hettich Laborapparate) at 1066 g for 15 min. After removal of the plasma fraction the PBMC containing phase was transferred in a new tube and washed twice with FACS-buffer (D-PBS #L1820, 5% FBS #SO115, Biochrom). Erythrocyte lysis was performed with lysis buffer (8.29 g/l $NH_4Cl$, 1.00 g/l $KHCO_3$, 0.037 g/l EDTA) for 5 min at room temperature. For subsequent purification of untouched T cells the human Pan T cell-isolation Kit II (#130-091-156, Miltenyi Biotec) was used according to the manufacturer's instructions.

Characterization of Isolated Human T Cells by Flow Cytometry.

Isolated T cells were characterized by flow cytometry for surface expression of adhesion molecules and activation markers. FACS staining and washing procedures were performed at 4° C. in cold FACS-buffer (D-PBS with 5% FBS). To analyze surface-exposed adhesion molecules, $3 \times 10^5$ T cells were stained in 100 µl of FACS-buffer with anti-CD11a-APC (1:10) (#550852, BD Biosciences), anti-CD49d-PE (1:10) (#560972, BD Biosciences), and anti-CD162-PerCP-eFluor710 (1:20) (#46-1629, eBioscience). Possible activation of T cells was monitored by staining $3 \times 10^5$ T cells with anti-CD69-PE (1:40) (#555531, BD Biosciences), anti-CD25-APC (1:40) (#340907, BD Biosciences), and anti-HLA-DR-FITC (1:40) (#555811, BD Biosciences). Furthermore, anti-CD3-V450 (1:40) (#560365, BD Biosciences), anti-CD4-APC-Cy7 (1:40) (#341115, BD Biosciences), and anti-CD8-V500 (1:40) (#560774, BD Biosciences) were included in both staining to characterize T cell-subpopulations. Separate staining of $3 \times 10^5$ T cells with DAPI (1 µg/ml) (#A1001.0010, Applichem) allowed for monitoring of cell viability. Staining for 30 min was followed by washing of cells twice with FACS-buffer. Stained samples were subjected to FACS analysis on a FACSCanto II instrument (BD Biosciences) and statistical analysis was performed using the FACSDiva software (BD Biosciences). 10,000 events were recorded and CD4-, CD8-, CD11a-, CD49d-, CD162-, CD69-, CD25-, and HLA-DR-positive cells were expressed as percentage of CD3-positive cells.

Cultivation of Endothelial Cells Under Flow Conditions with the Ibidi Pump System.

The ibidi Pump System (#10902, ibidi) was used for cultivation of endothelial cells under flow conditions as well as for performing adhesion and rolling assays of human T cells on endothelial cells. The system consists of the ibidi Pump (#10905, ibidi) and the ibidi Fluidic Unit (#10903, ibidi) which work together to generate a unidirectional flow of medium in an attached slide with a defined channel height. The system is controlled by the ibidi Pump Control software (#10908, notebook+software, ibidi). For cultivation of HBMEC or HUVEC under flow conditions, HBMEC or HUVEC were seeded at a cell density of $2.5 \times 10^6$ cells/ml into µ-slide $I^{0.4}$ Luer Collagen IV (#80172, ibidi) or µ-slide $I^{0.4}$ Luer ibiTreat (#80176, ibidi), respectively according to the manufacturer's instructions and cultivated with a perfusion set "yellow/green" (#10964, ibidi) for 48 h under wall shear stress of 5 or 10 dyn/cm$^2$, respectively. For the cultivation of more than one µ-slide $I^{0.4}$ Luer with a single fluidic unit, up to four µ-slides were connected to each other with the Serial Connectors for µ-slides (#10830, ibidi).

For the additional pre-incubation of HBMEC with pentosanpolysulfate SP54® (100 mg/ml injection solution, bene Arzneimittel GmbH), PPS was added to HBMEC cell culture medium (200 µg/ml) 24 h prior to any experiments. Histamine pre-stimulation of HBMEC was done prior to rolling and adhesion experiments with $10^{-5}$ M histamine (#H7125-1G, Sigma-Aldrich) in HBMEC cell culture medium for 30 min at 37° C.

Incubation of Human T Cells with Compounds Mediating Anti-Leukocyte Adhesion.

For further interference with AMG 103-mediated adhesion effects, T cells were pre-incubated with compounds potentially mediating anti-leukocyte adhesion prior to rolling and adhesion experiments. Therefore, Tysabri (Natalizumab, 20 mg/ml solution, Elan Pharma International Ltd.) or Minocin (Minocycline, 100 mg/vial, Triax Pharmaceuticals) were added to the T cell-suspension and incubated at 37° C.

Interaction of Human T Cells with HBMEC or HUVEC Under Flow Conditions: Assay Setup for Rolling and Adhesion Experiments.

Experiments under defined hydrodynamic flow conditions were performed by using freshly isolated human T cells and flow-cultivated HBMEC or HUVEC as described above, and were analyzed with a microscopic system consisting of the inverse microscope Ti-E (#MEA53100, Nikon), the digital camera Orca Flash 2.8 (#C-11440-10C, Hamamatsu), the NIS-Elements AR software versions 3.22.00 and 4.10.03 (#MQS31200 and #MQS31100, Nikon), the ibidi Pump System (#10902, ibidi), the cell culture incubator Galaxy 14S (#C014S-120-0000, Eppendorf), the Heating System 8 (#10925, ibidi), and the $CO_2$ gas incubation unit I (#10920, ibidi). The microscope Ti-E was equipped with a TI-ND6-PFS Perfect Focus System (#MEP59390, Nikon) allowing for the correction of parfocal variances. Rolling and adhesion events were monitored with a 10x objective (CFI PlanFluor DL-10 X phase, #MRH20101, Nikon). The Heating System 8 and the $CO_2$ gas incubation unit I were started at least 3 h before starting any experiment, pre-warming the stage top incubator to 37° C. and 5% $CO_2$. RPMI 1640 medium (#FG1215, Biochrom) was also pre-warmed at 37° C. and 5% $CO_2$. For rolling and adhesion experiments the µ-slide $I^{0.4}$ Collagen IV with flow-cultivated HBMEC or the µ-slide $I^{0.4}$ ibiTreat with flow-cultivated HUVEC was disconnected from the perfusion set, rinsed with pre-warmed RPMI 1640 medium with PPS (200 µg/ml) or without PPS and placed in the µ-slide inlet of the stage top incubator under the microscope. $6 \times 10^6$ freshly isolated human T cells were centrifuged in PC V-tubes (#347759, Nunc) at 300 g for 4 min. T cells were resuspended in RPMI 1640 medium with PPS (200 µg/ml) or without PPS to a final T cell-density of $1 \times 10^6$ cells/ml. These cells were either used directly for rolling experiments with or without addition of AMG 103 (10 ng/ml) to the cell suspension, or further pre-incubated in PC V-tubes at 37° C. for 45 min in the presence or absence of AMG 103. Such prepared T cell-suspension was filled in a perfusion set "white" (#10963, ibidi) which was connected to both a fluidic unit and the µ-slide. Two different setup for rolling and adhesion experiments of T cells on HBMEC or HUVEC at a shear stress of 1 dyn/cm$^2$ were applied:

1. Rolling of T cells on endothelial cells for 45 sec (short-term condition)
2. Rolling of T cells on endothelial cells for 45-120 min (long-term condition, with fluidic unit being placed in the cell culture incubator)

Interaction of Human T Cells with HBMEC or HUVEC Under Flow Conditions: Data Acquisition and Analysis.

T cell-interactions with endothelial cells were monitored by image acquisition with digital camera Orca Flash 2.8 which in turn was controlled by NIS-Elements software 3.22.00. Time-lapse 45 sec acquisition (without delay) was performed for individual time points resulting in up to 45 frames/sec at a resolution of 1920×1440. Such recorded image sequences of 45 sec duration were subjected to the automated tracking module of NIS-Elements AR 4.10.03 or subjected to manual tracking with NIS-Elements AR 3.22.00. Generated tracking data were exported to Microsoft Excel and further analyzed by applying filters on parameters such as average heading, average speed and path length for each tracked object. Subsequently, mean rolling velocity±standard deviation of all filtered cells was calculated. When using manual tracking, 10-40 T cells were selected, tracked manually and the mean rolling velocity±standard deviation was determined.

Immunofluorescence Staining of HBMEC or HUVEC.

After rolling and adhesion of T cells on HBMEC or HUVEC under flow conditions, endothelial cells were fixed using 150 µl of 4% paraformaldehyde solution (#P-6148, Sigma-Aldrich) for 30 min at 4° C. µ-slides were rinsed with 150 µl of D-PBS and subjected to immunofluorescence staining. HBMEC were first blocked with 150 µl of avidin blocking reagent (#PHA-70871, reagent 1, Dianova) for 10 min at room temperature, washed with 150 µl of D-PBS followed by incubation with 150 µl of biotin blocking reagent (#PHA-70871, reagent 2, Dianova). All following staining procedures were performed in 150 µl of D-PBS with 5% FBS at room temperature in the dark, and washing steps were done in 150 µl of D-PBS. µ-slides were incubated with 5 µg/ml polyclonal rabbit anti-human VCAM-1 (#106777, abcam) for 1 h. After washing, 20 µg/ml goat anti-rabbit IgG-DyLight350 was added for 1 h followed by washing and incubation with 15 µg/ml mouse anti-human P-selectin IgG1 (#BBA30, R&D Systems) for 2 h. After washing, goat anti-mouse IgG-Alexa488 (1:100) (#A10680, Invitrogen) was added for 1 h. ICAM-1 staining was done with 10 µg/ml polyclonal rabbit anti-human ICAM-1 biotin (#AB7815, abcam) for 1 h, followed by washing and incubation with streptavidin-Cy3 (1:100) (#016-160-084, Dianova) for 1 h. Cell surface staining of ICAM-1 and P-selectin on PFA-fixed HUVEC was performed as described for HBMEC. Finally, HBMEC or HUVEC were subjected to microscopic analysis using UV-light and a CFI Plan Apochromat DM 20 x Lambda objective (#MRD30205, Nikon) with a PH-2 phase module (#MEH41200, Nikon). VCAM-1 staining was monitored with a CFL EPI-FL Filter Block UV-2A (#MBE41200, Nikon), P-selectin staining with a CFL EPI-FL Filter Block GFP-B (#MBE44740, Nikon), and ICAM-1 staining with an EPI-FL Filter Block Cy3 (#MXU96213, Nikon). Image acquisition was performed with the NIS-Elements software.

Statistical Data Analysis.

Depending on how many groups of data were compared, an unpaired t-test or a one-way ANOVA combined with a Tukey post-test were used to analyze statistical significance in Prism (GraphPad Software). A P-value<0.05 was regarded as statistically significant.

T cells pre-incubated with 10 ng/ml of Blinatumomab (+AMG 103) for 45 min showed a significantly reduced mean rolling velocity±SD of 237±45 µm/sec on HUVEC in short-term conditions when compared to the negative control (−AMG 103; 283±82 µm/sec). Simultaneously, pre-incubation with 10 ng/ml of Blinatumomab increased the number of T cells firmly adhering to HUVEC by 2.6-fold. Additionally, HUVEC-activation was observed as shown by increased surface expression of adhesion molecules ICAM-1 and P-selectin when corresponding T cells were pre-incubated with 10 ng/ml of Blinatumomab compared to basal expression levels on HUVEC that only had contact to untouched T cells. These findings demonstrated increased interaction and firm adhesion of Blinatumomab-incubated T cells with/to HUVEC thereby in turn activating and increasing adhesiveness of these cells (FIG. 5).

When using HBMEC, mean T cell-rolling velocity±SD was significantly reduced to 209±40 µm/sec in the presence of 10 ng/ml of Blinatumomab (+AMG 103) in long-term conditions compared to the negative control (−AMG 103; 323±78 µm/sec). This reduction was observed 45 min after addition of Blinatumomab to the flow system, while no decrease of T cell-rolling velocity was detectable immediately after addition of Blinatumomab (0 min). HBMEC having interacted with Blinatumomab-stimulated T cells showed increased surface expression of adhesion molecules ICAM-1, P-selectin and VCAM-1 after T cell-rolling compared to basal expression levels on HUVEC that only had contact to untouched T cells. These observations demonstrated Blinatumomab-induced increased T cell-interaction with HBMEC and simultaneous increased HBMEC-adhesiveness which timely (i.e. after 45 min) correlated with time courses of T cell-redistribution in clinical studies (FIG. 6).

The influence of PPS on Blinatumomab-induced reduction of mean T cell-rolling velocity as observed 45 min after addition of 10 ng/ml of Blinatumomab to the flow system was evaluated in long-term conditions. While AMG 103 significantly reduced mean T cell-rolling velocity±SD on HBMEC from 430±92 µm/sec (−AMG 103) to 281±96 µm/sec (+AMG 103), further addition of PPS to the flow system reverted this reduction to a mean T cell-rolling velocity±SD of 483±157 µm/sec as also observed in the absence of AMG 103 (i.e. −AMG 103, +PPS; 442±156 µm/sec). Cell surface expression of P-selectin on HBMEC was increased when Blinatumomab was added to the flow system, whereas further addition of (i.e. pre-incubation of HBMEC with) PPS led to a lesser increase. Thus, prevention of T cell-interaction with HBMEC by PPS also diminished T cell-mediated increase of HBMEC-activation and adhesiveness (FIG. 7).

As described in detail above for PPS in combination with histamine pre-stimulated HBMEC, the flow system was also used to analyze the interference of PPS with AMG 103-induced T cell-interactions with non-stimulated HBMEC.

The influence of PPS on Blinatumomab-induced reduction of mean T cell-rolling velocity was evaluated under long-term conditions. While AMG 103 significantly reduced mean T cell-rolling velocity±SD on HBMEC from 399±153 µm/sec (−AMG 103) to 263±66 µm/sec (+AMG 103) at 40 min after addition of 10 ng/ml Blinatumomab to the flow system, further addition of PPS to the experiment reverted this reduction to a mean T cell-rolling velocity±SD of 465±116 µm/sec as also observed in the absence of AMG 103 (i.e., −AMG 103, +PPS; 514±159 µm/sec). Thus, PPS prevented the Blinatumomab-induced increase of T cell-interactions with endothelial cells (FIG. 8).

As described in detail above for PPS in combination with histamine pre-stimulated HBMEC, the flow system was also used to analyze the interference of natalizumab with AMG 103-induced T cell-interactions with non-stimulated HBMEC. To this end, freshly isolated T cells were incubated with 1 µg/ml natalizumab in RPMI 1640 medium for 10 min at 37° C. prior to rolling and adhesion experiments.

The influence of natalizumab on Blinatumomab-induced reduction of mean T cell-rolling velocity was evaluated under long-term conditions. While AMG 103 significantly reduced mean T cell-rolling velocity±SD on HBMEC from 482±149 µm/sec (−AMG 103) to 359±102 µm/sec (+AMG 103) at 40 min after addition of 10 ng/ml Blinatumomab to the flow system, further addition of natalizumab to the experiment reverted this reduction to a mean T cell-rolling velocity±SD of 444±110 μm/sec as also observed in the absence of AMG 103 (i.e., −AMG 103, +natalizumab; 445±81 μm/sec). Thus, natalizumab prevented the Blinatumomab-induced increase of T cell-interactions with endothelial cells (FIG. 9).

As described in detail above for PPS in combination with histamine pre-stimulated HBMEC, the flow system was also used to analyze the interference of minocycline with AMG 103-induced T cell-interactions with non-stimulated HUVEC. To this end, freshly isolated T cells were incubated with 50 μg/ml minocycline in Dulbecco's PBS for 2 h at 37° C. prior to rolling and adhesion experiments.

The influence of minocycline on Blinatumomab-induced reduction of mean T cell-rolling velocity was evaluated under long-term conditions. While AMG 103 significantly reduced mean T cell-rolling velocity±SD on HUVEC from 169±μm/sec (−AMG 103) to 127±41 μm/sec (+AMG 103) at 40 min after addition of 10 ng/ml Blinatumomab to the flow system, further addition of minocycline to the experiment reverted this reduction to a mean T cell-rolling velocity±SD of 217±92 μm/sec as also observed in the absence of AMG 103 (i.e., −AMG 103, +minocycline; 233±29 μm/sec) (FIG. 10).

In yet another experiment, the influence of minocycline on Blinatumomab-induced increase of absolute numbers of T cells firmly adhering to HUVEC was evaluated under long-term conditions. The number of adhering T cells at 40 min after addition of 10 ng/ml Blinatumomab to the flow system was significantly increased (2.1-fold) in the presence of Blinatumomab (+AMG 103) compared to T cells alone (−AMG 103). Further addition of minocycline to the experiment (+AMG 103, +minocycline) reverted the increased number of adhering T cells to a comparable or even lower level as observed in the absence of Blinatumomab (−AMG 103; ±minocycline) (FIG. 11).

Thus, minocycline prevented the Blinatumomab-induced increase of T cell-interactions with endothelial cells.

As described in detail above for PPS in combination with histamine pre-stimulated HBMEC, the flow system was also used to analyze the interference of an anti-ICAM-1 antibody with AMG 103-induced T cell-interactions with non-stimulated HBMEC. To this end, HBMEC were incubated with 10 μg/ml mouse anti-human ICAM-1 antibody (#MAB2146Z, Millipore) for 30 min at 37° C. prior to rolling and adhesion experiments.

The influence of the anti-ICAM-1 antibody on Blinatumomab-induced reduction of mean T cell-rolling velocity was evaluated under long-term conditions. While AMG 103 significantly reduced mean T cell-rolling velocity±SD on HBMEC from 407±90 μm/sec (−AMG 103) to 335±μm/sec (+AMG 103) at 30 min after addition of 10 ng/ml Blinatumomab to the flow system, further addition of the anti-ICAM-1 antibody to the experiment reverted this reduction to a mean T cell-rolling velocity±SD of 416±97 μm/sec as also observed in the absence of AMG 103 (i.e., −AMG 103, +anti-ICAM-1 Ab; 378±64 μm/sec). Thus, the anti-ICAM-1 antibody prevented the Blinatumomab-induced increase of T cell-interactions with endothelial cells (FIG. 12).

As described in detail above for PPS in combination with histamine pre-stimulated HBMEC, the flow system was also used to analyze the interference of an anti-P-selectin antibody with AMG 103-induced T cell-interactions with non-stimulated HBMEC. To this end, HBMEC were incubated with 10 μg/ml mouse anti-human P-selectin antibody (#MAB2154, Millipore) for 30 min at 37° C. prior to rolling and adhesion experiments.

The influence of the anti-P-selectin antibody on Blinatumomab-induced reduction of mean T cell-rolling velocity was evaluated under long-term conditions. While AMG 103 significantly reduced mean T cell-rolling velocity±SD on HBMEC from 449±90 μm/sec (−AMG 103) to 370±55 μm/sec (+AMG 103) at 40 min after addition of 10 ng/ml Blinatumomab to the flow system, further addition of the anti-P-selectin antibody to the experiment reverted this reduction to a mean T cell-rolling velocity±SD of 440±95 μm/sec as also observed in the absence of AMG 103 (i.e., −AMG 103, +anti-P-selectin Ab; 494±105 μm/sec). Thus, the anti-P-selectin antibody prevented the Blinatumomab-induced increase of T cell-interactions with endothelial cells (FIG. 13).

As described in detail above for PPS in combination with histamine pre-stimulated HBMEC, the flow system was also used to analyze the interference of an anti-CD11a antibody with AMG 103-induced T cell-interactions with non-stimulated HBMEC. To this end, freshly isolated T cells were incubated with 5 μg/ml mouse anti-human CD11a antibody (#217640, Calbiochem) in RPMI 1640 medium for 10 min at 37° C. prior to rolling and adhesion experiments.

The influence of the anti-CD11a antibody on Blinatumomab-induced reduction of mean T cell-rolling velocity was evaluated under long-term conditions. While AMG 103 significantly reduced mean T cell-rolling velocity±SD on HBMEC from 304±40 μm/sec (−AMG 103) to 214±μm/sec (+AMG 103) at 10 min after addition of 10 ng/ml Blinatumomab to the flow system, further addition of the anti-CD11a antibody to the experiment reverted this reduction to a mean T cell-rolling velocity±SD of 261±56 μm/sec as also observed in the absence of AMG 103 (i.e., −AMG 103, +anti-CD11a Ab; 278±48 μm/sec). Thus, the anti-CD11a antibody prevented the Blinatumomab-induced increase of T cell-interactions with endothelial cells (FIG. 14).

As described in detail above for PPS in combination with histamine pre-stimulated HBMEC, the flow system was also used to analyze the interference of an anti-CD162 antibody with AMG 103-induced T cell-interactions with non-stimulated HBMEC. To this end, freshly isolated T cells were incubated with 10 μg/ml mouse anti-human CD 162 antibody (#ab78188, abcam) in RPMI 1640 medium for 10 min at 37° C. prior to rolling and adhesion experiments. Alternatively, instead of incubating T cells with the anti-CD162 antibody, T cells were incubated with 10 μg/ml mouse isotype control antibody (IgG1,κ; MOPC-21; #M5284, Sigma-Aldrich) in RPMI 1640 medium for 10 min at 37° C. prior to rolling and adhesion experiments.

The influence of the anti-CD162 antibody on Blinatumomab-induced reduction of mean T cell-rolling velocity was evaluated under long-term conditions. While AMG 103 significantly reduced mean T cell-rolling velocity±SD on HBMEC from 539±149 μm/sec (−AMG 103) to 428±89 μm/sec (+AMG 103) at 45 min after addition of 10 ng/ml Blinatumomab to the flow system, further addition of the anti-CD162 antibody to the experiment reverted this reduction to a mean T cell-rolling velocity±SD of 637±191 μm/sec as also observed in the absence of AMG 103 (i.e., −AMG 103, +anti-CD162 Ab; 528±170 μm/sec). In contrast, addition of the isotype control antibody in the presence of AMG 103 resulted in a mean T cell-rolling velocity±SD of 258±65 μm/sec (+AMG 103, +mouse IgG1,κ) and did not revert the AMG 103-induced reduction of mean T cell-rolling velocity as observed for the anti-CD162 antibody. Thus, the anti-CD162 antibody specifically prevented the Blinatumomab-induced increase of T cell-interactions with endothelial cells by selectively interfering with the binding of CD162 to P-selectin. This prevention could not be induced by the unspecific mouse isotype control antibody (FIG. 15).

As described in detail above for PPS in combination with histamine pre-stimulated HBMEC, the flow system was also used to analyze the interference of recombinant P-selectin with AMG 103-induced T cell-interactions with non-stimulated HBMEC. To this end, freshly isolated T cells were incubated with 5 µg/ml recombinant human P-selectin (#ADP3-050, R&D Systems) in RPMI 1640 medium for 15 min at 37° C. prior to rolling and adhesion experiments.

The influence of recombinant P-selectin on Blinatumomab-induced reduction of mean T cell-rolling velocity was evaluated under long-term conditions. While AMG 103 significantly reduced mean T cell-rolling velocity±SD on HBMEC from 386±77 µm/sec (−AMG 103) to 340±68 µm/sec (+AMG 103) at 45 min after addition of 10 ng/ml Blinatumomab to the flow system, further addition of recombinant P-selectin to the experiment reverted this reduction to a mean T cell-rolling velocity±SD of 402±93 µm/sec as also observed in the absence of AMG 103 (i.e., −AMG 103, +rec. P-selectin; 384±70 µm/sec). Thus, recombinant P-selectin prevented the Blinatumomab-induced increase of T cell-interactions with endothelial cells (FIG. 16).

Example 3

Doses and Schedules of Co-medications Following the Principle of Anti-leukocyte Adhesion for Mitigating CNS AEs Administration Schedule for Intravenous PPS Co-Medication with Blinatumomab Treatment for Use in Humans.

Patients receive a 100 mg bolus injection of PPS 3 h±30 min prior to start of infusion and any dose step of Blinatumomab. Immediately after the bolus injection, intravenous administration of PPS is continued by perfusor at 300 mg/day for 72 h.

Administration Schedule for Oral PPS Co-Medication with Blinatumomab Treatment For Use in Humans.

Patients receive 900 mg PPS daily given orally as 300 mg (e.g. 3×100 mg) three times per day starting 7 days before start of infusion and any dose step of Blinatumomab. Oral administration of 900 mg PPS daily is continued for 72 h after start of infusion and any dose step of Blinatumomab.

Administration Schedule for Intravenous Minocycline Co-Medication with Blinatumomab Treatment for Use in Humans.

Patients receive 10 mg/kg Minocycline by short-term intravenous infusion 48 h, 24 h and 3 h±30 min prior to and 24 h, 48 h and 72 h after start of infusion and any dose step of Blinatumomab.

Administration Schedule for Oral Minocycline Co-Medication with Blinatumomab Treatment for Use in Humans.

Patients receive 700 mg Minocycline orally once daily 48 h, 24 h and 3 h±30 min prior to and 24 h, 48 h and 72 h after start of infusion and any dose step of Blinatumomab.

Administration Schedule for Intravenous Natalizumab Co-Medication with Blinatumomab Treatment for Use in Humans.

Patients receive 300 mg Natalizumab by short-term intravenous infusion 24 h prior to start of infusion and any dose step of Blinatumomab.

Example 4

In Vitro Flow Chamber System Using Recombinant Adhesion Molecules

Coating of Recombinant Proteins.

Recombinant proteins (rhICAM-1 #ADP4-050, rhV-CAM-1 #ADP5-050 or rhP-selectin #ADP3-050, R&D Systems) were dissolved in $ddH_2O$ according to the manufacturer's instructions. Prior to rolling experiments recombinant proteins were diluted in Dulbecco's PBS with $Ca^{2+}$ and $Mg^{2+}$ (#L1815, Biochrom) and coated onto a µ-slide $VI^{0.4}$ Luer ibiTreat (#80606, ibidi) over night at 4° C. Before usage slides were washed three times with Dulbecco's PBS and blocked where indicated with 20% FBS (#10270, Gibco) in PBS for 2 h at room temperature. Blocking solution was replaced by RPMI 1640 medium (#FG1215, Biochrom) without supplements.

Isolation and Cultivation of Human T Cells.

Isolation and characterization of human peripheral blood mononuclear cells (PBMC) and T cells from blood were performed as described in Example 2 (p. 48, 1-31).

Jurkat E6.1 T cells (#88042803, European Collection of Cell Cultures) were grown at 37° C. and 5% $CO_2$ in RPMI 1640 medium (#FG1215, Biochrom) containing 10% FBS (#10270, Gibco) and penicillin/streptomycin (#A2213, Biochrom).

For rolling experiments using freshly isolated T cells, these cells were resuspended in RPMI 1640 medium (#FG1215, Biochrom) without supplements to a final concentration of $1×10^6$ cells/ml at the start of the experiment (t=0 min; addition of 10 ng/ml Blinatumomab (AMG 103)) and incubated for 35 min at 37° C. and 5% $CO_2$. Cells were then filled in a perfusion set "white" (#10963, ibidi) which was connected to both a fluidic unit and the µ-slide and image sequences of 45 sec duration were recorded at t=40 min, 45 min, and 50 min as described in Example 2 (p. 50, 18-23).

For rolling experiments using Jurkat E6.1 T cells, these cells were resuspended in RPMI 1640 medium (#FG1215, Biochrom) without supplements to a final concentration of $1.5-3×10^5$ cells/ml. Jurkat E6.1 T cells were starved either over night at 0.5% FBS in RPMI 1640 medium or for 40 min in RPMI 1640 medium without supplements prior to the addition of 10 ng/ml Blinatumomab (AMG 103, t=0 min). Cells were incubated for 35 min at 37° C. and 5% $CO_2$ and then filled in a perfusion set "white" (#10963, ibidi) which was connected to both a fluidic unit and the µ-slide. Image sequences of 45 sec duration were recorded at t=40 min, 45 min, and 50 min as described in Example 2 (p. 50, 18-23).

Incubation of Human T Cells with an Inhibitor of T Cell-Signal Transduction.

For interference with AMG 103-induced adhesion effects, T cells were pre-incubated with a Src kinase inhibitor specifically blocking signal transduction from the T cell-receptor complex. To this end, the inhibitor PP2 (#529576, Merck, 15 µM) or its vehicle control DMSO (#D2650, Sigma-Aldrich) were added to the T cell-suspension ($1×10^6$ cells/ml in RPMI 1640 medium) which then was incubated for 40 min at 37° C. and 5% $CO_2$ prior to addition of 10 ng/ml Blinatumomab (AMG 103, t=0 min).

Interaction of Human T Cells with Recombinant Adhesion Molecules Under Flow Conditions: Assay Setup for Rolling Experiments, Data Acquisition and Analysis.

Experiments under defined hydrodynamic flow conditions were performed by using either freshly isolated human T cells or Jurkat E6.1 T cells and µ-slide $VI^{0.4}$ Luer ibiTreat (#80606, ibidi) coated with different recombinant proteins as described above. The assay setup was described in detail in Example 2 (p. 49, 23-37). T cell-rolling experiments were performed at a shear stress of 1.1 dyn/cm$^2$. T cell-interactions with recombinant proteins were recorded as described above and data was analyzed as described in detail in Example 2 (p. 50, 23-30).

Statistical Data Analysis.

Depending on how many groups of data were compared, an unpaired t-test or a one-way ANOVA combined with a Tukey post-test were used to analyze statistical significance in Prism (GraphPad Software). A P-value<0.05 was regarded as statistically significant. All values are indicated as mean±SD.

Freshly isolated T cells incubated with 10 ng/ml Blinatumomab (+AMG 103) showed a significantly reduced mean T cell-rolling velocity±SD at t=45 min on recombinant human ICAM-1 (coated at 12.5 µg/ml, with blocking; −AMG 103: 383±144 µm/sec vs.+AMG 103: 314±79 µm/sec), on recombinant human VCAM-1 (coated at 10 µg/ml, with blocking; −AMG 103: 418±136 µm/sec vs.+AMG 103: 353±72 µm/sec), and at t=50 min on recombinant human P-selectin (coated at 20 µg/ml, with blocking; −AMG 103: 402±115 µm/sec vs.+AMG 103: 293±73 µm/sec) in semi short-term conditions when compared to the negative control (−AMG 103) (FIG. 17A-C).

Jurkat E6.1 T cells incubated with 10 ng/ml Blinatumomab (+AMG 103) showed a significantly reduced mean T cell-rolling velocity±SD at t=45 min on recombinant human ICAM-1/VCAM-1 (coated at 12.5 and 10 µg/ml, respectively; −AMG 103: 640±91 µm/sec vs.+AMG 103: 518±98 µm/sec), and on recombinant human P-selectin (coated at 20 µg/ml; −AMG 103: 500±81 µm/sec vs.+AMG 103: 413±104 µm/sec) in semi short-term conditions when compared to the negative control (−AMG 103) (FIG. 17D, E).

Thus, Blinatumomab also increases T cell-interactions with recombinant human adhesion molecules both for freshly isolated T cells and a common T cell-line.

The influence of the Src kinase inhibitor PP2 on Blinatumomab-induced reduction of mean T cell-rolling velocity was evaluated under semi short-term conditions. While AMG 103 in the presence of the vehicle control DMSO significantly reduced mean T cell-rolling velocity±SD on VCAM-1-coated µ-slides (coated at 20 µg/ml) from 259±35 µm/sec (−AMG 103) to 205±45 µm/sec (+AMG 103) at t=40 min after addition of 10 ng/ml Blinatumomab, pre-incubation and presence of 15 µM PP2 in the experiment reverted this reduction to a mean T cell-rolling velocity±SD of 256±50 µm/sec. PP2 treatment in the absence of AMG 103 resulted in a comparable mean T cell-rolling velocity±SD of 267±66 µm/sec (−AMG 103, +PP2). Thus, Src kinase inhibitor PP2 prevented the Blinatumomab-induced increase of T cell-interactions with recombinant human VCAM-1 (FIG. 18).

The invention claimed is:

1. A method of ameliorating, treating, or preventing a clinical adverse event in a patient caused by administering blinatumomab to the patient, the method comprising administering to the patient an effective amount of pentosanpolysulfate (PPS) or a pharmaceutically acceptable salt thereof, minocycline, or natalizumab.

2. The method according to claim 1, wherein the method further comprises administering to the patient genetically engineered T-cells having a chimeric antigen receptor (CAR).

3. The method according to claim 2, wherein said chimeric antigen receptor (CAR) comprises a CD19 binding domain.

4. The method according to claim 1, wherein the pentosanpolysulfate (PPS) or the pharmaceutically acceptable salt thereof, minocycline, or natalizumab is administered prior to or concomitantly with an initial dosing, a re-exposure, or an increase in dose of blinatumomab.

5. The method according to claim 1, wherein said clinical adverse event comprises a neurological adverse event.

6. The method according to claim 5, wherein said neurological adverse event is one or more of (i) a cognitive disorder comprising disorientation, confusion or word-finding problems (aphasia), (ii) a seizure, (iii) a cerebellar symptom partly observed as an optional prodromal phase of (i) or (ii) comprising a kinetic tremor, ataxia, dysarthria and/or handwriting problems.

7. The method according to claim 1, wherein said patient is characterized by a B:T-cell ratio of less than 1:5 or a B-cell number of less than about 50 B-cells per µl peripheral blood.

8. The method according to claim 1, wherein said patient is a mammal.

9. The method according to claim 8, wherein said mammal is a primate.

10. The method according to claim 9, wherein said primate is a human.

* * * * *